(12) United States Patent
Oshita et al.

(10) Patent No.: US 7,788,038 B2
(45) Date of Patent: Aug. 31, 2010

(54) BIOLOGICAL INFORMATION AND BLOOD TREATING DEVICE INFORMATION CONTROL SYSTEM, BIOLOGICAL INFORMATION AND BLOOD TREATING DEVICE INFORMATION CONTROL DEVICE, AND BIOLOGICAL INFORMATION AND BLOOD TREATING DEVICE INFORMATION CONTROL METHOD

(75) Inventors: Shuzo Oshita, Tokushima (JP); Yasuhiro Kuroda, Himeji (JP); Toshiya Okahisa, Tokushima (JP); Yoshiaki Ohnishi, Tokushima (JP); Noriko Okumura, Takarazuka (JP)

(73) Assignee: Koninklijke Philips Electronics N.V., Eindhoven (NL)

( * ) Notice: Subject to any disclaimer, the term of this patent is extended or adjusted under 35 U.S.C. 154(b) by 925 days.

(21) Appl. No.: 10/450,648

(22) PCT Filed: Dec. 27, 2001

(86) PCT No.: PCT/JP01/11509

§ 371 (c)(1),
(2), (4) Date: Jun. 16, 2003

(87) PCT Pub. No.: WO02/053209

PCT Pub. Date: Jul. 11, 2002

(65) Prior Publication Data

US 2005/0102165 A1    May 12, 2005

(30) Foreign Application Priority Data

Dec. 27, 2000    (JP) .............................. 2000-397609

(51) Int. Cl.
*G06F 19/00* (2006.01)
*G01N 33/48* (2006.01)
*A61M 37/00* (2006.01)

(52) U.S. Cl. ............................ 702/19; 356/39; 604/4.01; 604/5.01; 604/6.09; 604/6.11; 604/7

(58) Field of Classification Search ...................... None
See application file for complete search history.

(56) References Cited

U.S. PATENT DOCUMENTS

| 6,061,590 | A  | * | 5/2000  | Krivitski ...................... 600/431 |
| 6,780,322 | B1 | * | 8/2004  | Bissler et al. ................ 210/637 |
| 6,814,864 | B1 | * | 11/2004 | Favre et al. ............. 210/321.65 |
| 7,072,769 | B2 | * | 7/2006  | Fletcher-Haynes et al. .... 702/21 |

FOREIGN PATENT DOCUMENTS

WO    WO 01/08723    *    2/2001

OTHER PUBLICATIONS

Morales et al. (2001) IEEE Transactions on Control Systems Technology, vol. 9, pp. 445-457.*

* cited by examiner

*Primary Examiner*—Lori A Clow

(57) ABSTRACT

The invention comprises a patient information server device which automatically accumulates together with time information: biological information detected by a bedside monitoring device of a patient or a biological-measuring device; biological information and device information detected by a blood purification device which treats a blood sample taken from the patient; and blood information detected by a circulating blood volume measuring device that detects blood information about a circulating blood sample taken from the patient. A client device simultaneously and chronologically displays or records the patient information stored in the patient information server device. Through this arrangement, it is possible to obtain on a real time basis the biological information of a human body such as a patient's body, and the device information, for example, of a blood treating device.

16 Claims, 25 Drawing Sheets

Display 303
- Registered time
- Interval of 5 minutes
- Interval of 15 minutes
- Interval of 30 minutes
- Interval of 1 hour
- Interval of 2 hour
- Interval of 4 hour
- Interval of 8 hour
- Interval of 12 hour
- Interval of 24 hour
- Standard character
- Magnified character
- Cancel

FIG.13

Report 304
- Flow sheet for ICU
- Flow sheet for blood purification

Chart 305
- Addition of item
- Deletion of item
- Save

FIG.15

BIOLOGICAL INFORMATION AND BLOOD TREATING DEVICE INFORMATION CONTROL SYSTEM, BIOLOGICAL INFORMATION AND BLOOD TREATING DEVICE INFORMATION CONTROL DEVICE, AND BIOLOGICAL INFORMATION AND BLOOD TREATING DEVICE INFORMATION CONTROL METHOD

TECHNICAL FIELD

The present invention relates to a management system for biological information and information about a blood-treating device, a management apparatus for biological information and information about a blood-treating device, and a management method for biological information and information about a blood-treating device for accumulating and storing biological information measured about a human body, information about at least one of biological information and device information measured by a blood-treating device that treats a blood sample taken from the human body, and blood information measured by a circulating blood volume measuring device that measures blood information about a circulating blood sample taken from the human body, and for simultaneously and chronologically displaying or recording this information. Further, the present invention relates more particularly to a management system for biological information and information about a blood-treating device, a management apparatus for biological information and information about a blood-treating device, and a management method for biological information and information about a blood-treating device capable of, for example, grasping the state of a patient being in an acute stage in real time.

BACKGROUND ART

Up to now, an apparatus for measuring and recording biological information of the human body of a patient or the like (hereinafter referred to as a first conventional example) has been put to practical use. This first conventional example enters automatically or manually enters and displays or records biological information mainly about circulatory organs and respiratory organs, blood test data measured by a test department and therapeutical information (about transfusion, injected drug, special therapy and the like) and nursing information.

And for example, a conventional hemodialyzer (hereinafter referred to as a second conventional example) performs blood purification (hemodialysis) as a chronic dialysis in a comparatively short time mainly to a chronic renal insufficiency case being stable in a general condition as an auxiliary artificial kidney.

However, the first conventional example manually enters limited information as therapeutic information, and particularly manually enters and displays on a screen only the kind and period of performance of blood treatment performed as a part of special treatment in relation to information of blood treatment.

And the second conventional example has controlled the hemodialysis in a hemodialyzer but has not monitor-controlled it in connection with another apparatus. For example, there have been problems that it has been impossible to forecast when clogging of a filter (increase in transmembrane pressure of a filter) occurs during performing hemodialysis using a blood purification apparatus provided with a filter or performing another blood purification and that frequent changes of a filter or circuit leads to the loss of blood of a patient. In order to solve these problems, it is necessary but has been impossible up to now to continuously manage and analyze hematological parameters of various kinds of monitoring devices in operation and a patient.

Up to now, it has been impossible to (automatically or manually) enter or record detailed information about blood treatment (for example the state of performance (actual measurements, predetermined values, alarm information of an apparatus and the like) or simultaneously display biological information on a display screen of the relevant apparatus. Due to this, it is necessary to prepare a progress report form at the time of performing a blood treatment and write the information of performance in the form but it has been impossible to enter a large amount of accurate information about blood treatment in real time and to display or record the information at the same time as biological information. And it has been impossible to perform a detailed analysis of biological information in consideration of the influence of blood treatment and further it has been impossible also to perform various evaluations about blood treatment (for example, safety evaluation, operation evaluation, economic evaluation and the like).

Particularly, it is necessary but has been impossible up to now to simultaneously observe biological information of a patient and information of blood treatment in real time for the patient in an acute stage.

An object of the present invention is to provide a management system for biological information and information about a blood-treating device, a management apparatus for biological information and information about a blood-treating device, and a management method for biological information and information about a blood-treating device capable of solving the problems described above, grasping in real time biological information about the human body of a patient and the like and device information about a blood-treating device and the like, estimating specific information, and controlling various kinds of devices at the time of performing a blood treatment.

DISCLOSURE OF THE INVENTION

A management system for biological information and information about a blood-treating device according to a first aspect of the present invention is characterized by comprising:

a a server device for automatically accumulating and storing, together with time information (a) biological information about a human body measured by a biological-measuring device, (b) information about at least one of biological information and device information both measured by a blood-treating device that treats a blood sample taken from the human body, and (c) blood information measured by a circulating blood volume measuring device that measures blood information about a circulating blood sample taken from the human body;

a control means for simultaneously and chronologically displaying or recording the information stored in the server device.

And a management system for biological information and information about a blood-treating device according to a second aspect of the present invention is characterized by comprising:

a biological-measuring device for measuring biological information about a human body and outputting the measured information;

a blood-treating device for treating a blood sample taken from the human body and for measuring and outputting at least one of biological information and device information;

a circulating blood volume measuring device for measuring blood information about a circulating blood sample taken from the human body and outputting the measured information;

a server device for automatically and periodically incorporating the output information at predetermined intervals and storing the output information together with time information; and a control means for downloading the stored information by accessing the server device or downloading the stored information together with time information by periodically accessing the server at predetermined additional time intervals, and simultaneously and chronologically displaying or recording the downloaded information.

The above-mentioned management system for biological information and information about a blood-treating device is characterized in that the control means preferably calculates an index value using a predetermined arithmetic expression based on at least one of the stored information or the downloaded information and then simultaneously and chronologically displays or records the calculated index value together with the information to be displayed or recorded.

And the above-mentioned management system for biological information and information about a blood-treating device is characterized in that the control means preferably changes at least one of the additional time intervals and the display scale based on a predetermined variation in at least one of the stored information or the downloaded information and the calculated index value.

Further, the above-mentioned management system for biological information and information about a blood-treating device is characterized by preferably further comprising an input means for entering additional biological information which is different from the biological information, wherein the control means simultaneously and chronologically displays or records the downloaded information and the additional biological information.

And further, the above-mentioned management system for biological information and information about a blood-treating device is characterized in that the control means preferably calculates an index value using a predetermined arithmetic expression based on at least one of the stored information or the downloaded information and the additional biological information and then simultaneously and chronologically displays or records the calculated index value together with the information to be displayed or recorded.

And the above-mentioned management system for biological information and information about a blood-treating device is characterized in that the control means preferably changes at least one of the additional time intervals and the display scale based on a predetermined variation in at least one of the downloaded information, the calculated index value, and the additional biological information.

Further, the above-mentioned management system for biological information and information about a blood-treating device is characterized in that the server device preferably further stores at least one of diagnostic information, therapeutic information and test information;

and the control means further simultaneously and chronologically displays or records at least one of the diagnostic information, the therapeutic information and the test information.

And the above-mentioned management system for biological information and information about a blood-treating device is characterized in that the blood-treating device is preferably a blood purification device for purifying blood sampled from the human body by submitting the blood to filtration, dialysis or adsorption by the use of a filter; and the control means calculates an estimate of the clogging ratio of the filter attached to the blood purification device, based on the information stored in the server device. Hereupon, the above-mentioned management system is characterized in that the control means preferably controls a predetermined value of the blood purification device based on the calculated clogging ratio of the filter. Further, the above-mentioned management system is characterized in that the control means preferably calculates an estimate of the amount of substances in blood removed by the blood purification device based on the information stored in the server device and the calculated clogging ratio of the filter.

Further, the above-mentioned management system for biological information and information about a blood-treating device is characterized in that the control means preferably calculates an estimate of the concentration of a specific substance in blood based on the information stored in the server device, the calculated clogging ratio of the filter and the calculated amount of substances in blood removed by the blood purification device. Hereupon the above-mentioned management system for biological information and information about a blood-treating device is characterized in that the control means preferably controls, based on the calculated concentration of a specific substance, a dose of the substance to be administered to the human body.

And further, the above-mentioned management system for biological information and information about a blood-treating device is characterized in that the control means preferably calculates an estimate of biological information regarding balance between the intra- and extra-cellular contents of bodily water in the human body based on the information stored in the server device. Hereupon the above-mentioned management system is characterized in that the control means preferably controls a predetermined value of the blood-treating device based on the calculated biological information regarding balance between the intra- and extra-cellular contents of bodily water in the human body.

And further the above-mentioned management system for biological information and information about a blood-treating device is characterized in that the control means preferably calculates an estimate of biological information regarding oxygen in the human body based on the information stored in the server device. Hereupon, the above-mentioned management system is characterized in that the control means preferably controls a predetermined value of at least one of the blood-treating device and an artificial respirator attached to the human body, based on the calculated biological information regarding oxygen in the human body.

A management apparatus for biological information and information about a blood-treating device according to a third aspect of the present invention is a management apparatus for biological information and information about a blood-treating device useful for a management system for biological information and information about a blood-treating device, the management system comprising:

a server device for automatically accumulating and storing, together with time information, (a) biological information about a human body measured by a biological-measuring device, (b) information about at least one of biological information and device information measured by a blood-treating device that treats a blood sample taken from the human body, and (c) blood information measured by a circulating blood volume measuring device that measures blood information about a circulating blood sample taken from the human body, characterized by comprising:

a control means for simultaneously and chronologically displaying or recording the information stored in the server device.

And a management apparatus for biological information and information about a blood-treating device according to a fourth aspect of the present invention is a management apparatus for biological information and information about a blood-treating device useful for a management system for biological information and information about a blood-treating device, the management system comprising:

a biological-measuring device for measuring biological information about a human body and outputting the measured information;

a blood-treating device for treating a blood sample taken from the human body, and measuring and outputting at least one of biological information and device information;

a circulating blood volume measuring device for measuring and outputting blood information about a circulating blood sample taken from the human body; and a server device for automatically and periodically incorporating the output information at predetermined intervals and storing the output information together with time information, characterized by comprising:

a control means for downloading the stored information by accessing the server device, or downloading the stored information together with time information by periodically accessing the server at predetermined additional time intervals, and simultaneously and chronologically displaying or recording the downloaded information.

The above-mentioned management apparatus for biological information and information about a blood-treating device is characterized in that the control means preferably calculates an index value using a predetermined arithmetic expression based on at least one of the stored information or the downloaded information and then simultaneously and chronologically displays or records the calculated index value together with the information to be displayed or recorded.

And the above-mentioned management apparatus for biological information and information about a blood-treating device is characterized in that the control means preferably changes at least one of the additional time intervals and the display scale based on a predetermined variation in at least one of the stored information or the downloaded information and the calculated index value.

Further, the above-mentioned management apparatus for biological information and information about a blood-treating device is characterized by preferably further comprising an input means for entering additional biological information which is different from the biological information, wherein the control means simultaneously and chronologically displays or records the stored information or the downloaded information, and the additional biological information.

And further, the above-mentioned management apparatus for biological information and information about a blood-treating device is characterized in that the control means preferably calculates an index value using a predetermined arithmetic expression based on at least one of the stored information or the downloaded information and the additional biological information, and then simultaneously and chronologically displays or records the calculated index value together with the information to be displayed or recorded.

And the above-mentioned management apparatus for biological information and information about a blood-treating device is characterized in that the control means preferably changes at least one of the additional time intervals and the display scale based on a predetermined variation in at least one of the downloaded information, the calculated index value, and the additional biological information.

Further, the above-mentioned management apparatus for biological information and information about a blood-treating device is characterized in that the server device preferably further stores at least one of diagnostic information, therapeutic information and test information, and the control means further simultaneously and chronologically displays or records at least one of the diagnostic information, the therapeutic information and the test information.

And the above-mentioned management apparatus for biological information and information about a blood-treating device is characterized in that the blood-treating device is a blood purification device for purifying blood sampled from the human body by submitting the blood to filtration, dialysis or adsorption by the use of a filter; and the control means calculates an estimate of the clogging ratio of the filter attached to the blood purification device, based on the information stored in the server device. Hereupon, the above-mentioned management apparatus is characterized in that the control means preferably controls a predetermined value of the blood purification device based on the calculated clogging ratio of the filter. Further, the above-mentioned management apparatus is characterized in that the control means preferably calculates an estimate of the amount of substances in blood removed by the blood purification device based on the information stored in the server device and the calculated clogging ratio of the filter.

Further, the above-mentioned management apparatus for biological information and information about a blood-treating device is characterized in that the control means preferably calculates an estimate of the concentration of a specific substance in blood based on the information stored in the server device, the calculated clogging ratio of the filter and the calculated amount of substances in blood removed by the blood purification device. Hereupon the above-mentioned management apparatus is characterized in that the control means preferably controls, based on the calculated concentration of a specific substance, a dose of the substance to be administered to the human body.

And further, the above-mentioned management apparatus for biological information and information about a blood-treating device is characterized in that the control means preferably calculates an estimate of biological information regarding balance between the intra- and extra-cellular contents of bodily water in the human body based on the information stored in the server device. Hereupon the above-mentioned management apparatus is characterized in that the control means preferably controls a predetermined value of the blood-treating device based on the calculated biological information regarding balance between the intra- and extra-cellular contents of bodily water in the human body.

And further the above-mentioned management apparatus for biological information and information about a blood-treating device is characterized in that the control means preferably calculates an estimate of biological information regarding oxygen in the human body based on the information stored in the server device. Hereupon, the above-mentioned management apparatus is characterized in that the control means preferably controls a predetermined value of at least one of the blood-treating device and an artificial respirator attached to the human body, based on the calculated biological information regarding oxygen in the human body.

A management method for biological information and information about a blood-treating device according to a fifth aspect of the present invention is characterized by comprising the steps of:

automatically accumulating (a) biological information about a human body measured by a biological-measuring device, (b) information about at least one of biological information and device information measured by a blood-treating device that treats a blood sample taken from the human body, and (c) blood information measured by a circulating blood volume measuring device that measures blood information about a circulating blood sample taken from the human body, and storing the information, together with time information, into a server device; and simultaneously and chronologically displaying or recording the information stored in the server device.

And a management method for biological information and information about a blood-treating device according to a sixth aspect of the present invention is characterized by comprising the steps of: measuring biological information about a human body and outputting the measured information by means of a biological-measuring device;

treating a blood sample taken from the human body by means of a blood-treating device and measuring at least one of biological information and device information, followed by outputting the measured information;

measuring and outputting blood information about a circulating blood sample taken from the human body using a circulating blood volume measuring device;

automatically and periodically incorporating the output information at predetermined intervals and storing the output information together with time information into a server device, and downloading the stored information by accessing the server device or downloading the stored information together with time information by periodically accessing the server at predetermined additional time intervals, and simultaneously and chronologically displaying or recording the downloaded information. The above-mentioned management method for biological information and information about a blood-treating device is characterized by further comprising the steps of:

storing diagnostic information, therapeutic information and test information into the server device; and simultaneously and chronologically displaying or recording at least one of the diagnostic information, the therapeutic information and the test information.

BRIEF DESCRIPTION OF THE DRAWINGS

FIG. 13 is a table showing items to be branched by clicking display 303 in the flow sheet for blood purification of FIG. 10 with the mouse.

FIG. 14 is a table showing items to be branched by clicking report 304 in the flow sheet for blood purification of FIG. 10 with the mouse.

FIG. 15 is a table showing items to be branched by clicking chart 305 in the flow sheet for blood purification of FIG. 10 with the mouse.

BEST MODE FOR CARRYING OUT THE INVENTION

Preferred embodiments according to the present invention are described with reference to the drawings in the following.

Figure 1:
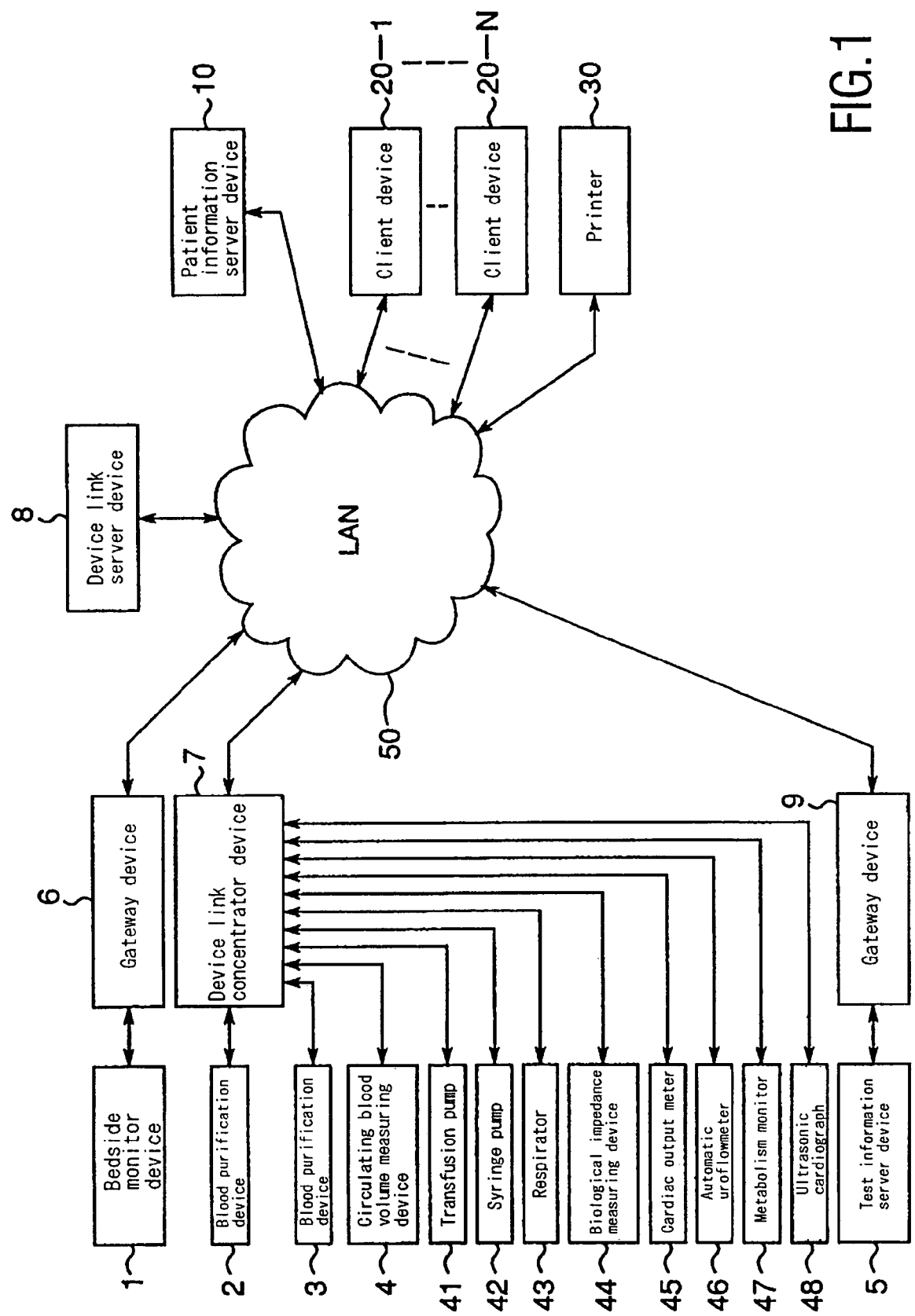
FIG. 1 is a block diagram showing the whole composition of a management system for biological information and device information being a preferred embodiment according to the present invention.

FIG. 1 is a block diagram showing the whole composition of a management system for biological information and device information being a preferred embodiment according to the present invention. A management system for biological information and device information according to this preferred embodiment is provided with a patient information server device 10 which automatically accumulates and stores, together with time information, biological information measured about a patient by a bedside monitor device 1 being a biological measurement device, biological information or device information measured in a blood purification device 2 or 3 for treating blood taken from the patient and blood information measured by a circulating blood volume measuring device 4 for measuring blood information of circulating blood taken from the patient, in which a client device 20 simultaneously and chronologically displays or records patient information including these information stored in the patient information server device 10 so as to be selectable by items. And the patient information server device 10 further stores test information such as a test time, a test result and the like inputted and stored by a test information server device 5 (including information about the time when and the part where a specimen has been taken and information of a blood test result, a urinalysis result and the like, for example), therapeutic information inputted from the client device 20 (for example, transfusion information and drug dosing information, which are important at the time of evaluating pharmacokinetics or a filter in particular) and diagnostic information inputted from the client device 20 (including consciousness level, psychical state, hemorrhagic stigma state and the like for example, which are needed for calculating scores), and simultaneously and chronologically displays or records these test information, therapeutic information and diagnostic information also in addition to the above patient information.

Hereupon, particularly the patient information server device 10 is characterized by automatically and periodically taking in these information outputted from the respective devices 1 to 5 and 41 to 48 at specific intervals, for example, at intervals of one minute or the like and storing these information together with time information, and the client device 20 is characterized by accessing the patient information server device 10 and downloading these information, or accessing the patient information server device 10 periodically at other time intervals and downloading the above-described stored information together with time information, and simultaneously and chronologically displaying or recording patient information including the downloaded information together with time information so as to be selectable by items. The device information means information measured, recorded, set or inputted by each device.

In FIG. 1, a bedside monitor device 1 is provided near the bed of a patient, measures biological information of the patient and transmits these data to the patient information server device 10 through a gateway device 6 for performing a signal processing such as a signal conversion or a protocol conversion and a local area network (hereinafter referred to as a LAN) 50. And each of blood purification devices 2 and 3 is a device for taking blood from a patient and purifying the blood through filtering, dialyzing and adsorbing the blood by means of a specific filter, and measures blood information including biological information, device information and the like measured in blood treatment including blood purification, and transmits these data to a device link server device 8 through a device link concentrator 7 for performing a signal processing such as a signal conversion, protocol conversion or the like and a LAN 50. Hereupon, the blood purification device 2 is a device mainly used for plasma exchange (PE), plasma adsorption (PP), double filtration plasma exchange (DFPP) and the like, and the blood purification device 3 is a device mainly used for continuous blood (hemoglobin) filtration dialysis (CHDF), continuous blood (hemoglobin) filtration (CHF), continuous hemo-plasma dialysis (CHD) and the like. Further, a circulating blood volume measuring device 4, which is a Crit Line Monitor (trademark) for example, measures blood information including biological information such as the circulating blood volume, its change rate, variation rate or the like with regard to blood of a patient taken when performing extracorporeal circulation and device information and the like, and transmits these data to the device link server device 8 through the device link concentrator 7 and the LAN 50. And the test information server device 5 enters and stores test information measured in various tests on a patient into a storage device 5 in the said device 5 and thereafter transmits these data to the patient information server device 10 through the gateway device 9 for performing a signal processing such as a signal conversion or a protocol conversion and the LAN 50. Hereupon, the device link server device 8 receives and once stores data sent from the respective devices 2, 3 and 4 into a storage in the said device 8 and thereafter transmits these data to the patient information server device 10. In the present invention, blood treatment including a blood purification process includes such processes as hemodialysis, blood filtration, blood filtration dialysis, blood adsorption, plasma exchange, plasma adsorption, peritoneal dialysis and the like. In this specification, patient information is a general term for the above-mentioned biological information of a patient and device information. Measurement items of the respective devices 1 to 5 and 41 to 48 are described in detail later.

Figure 5:
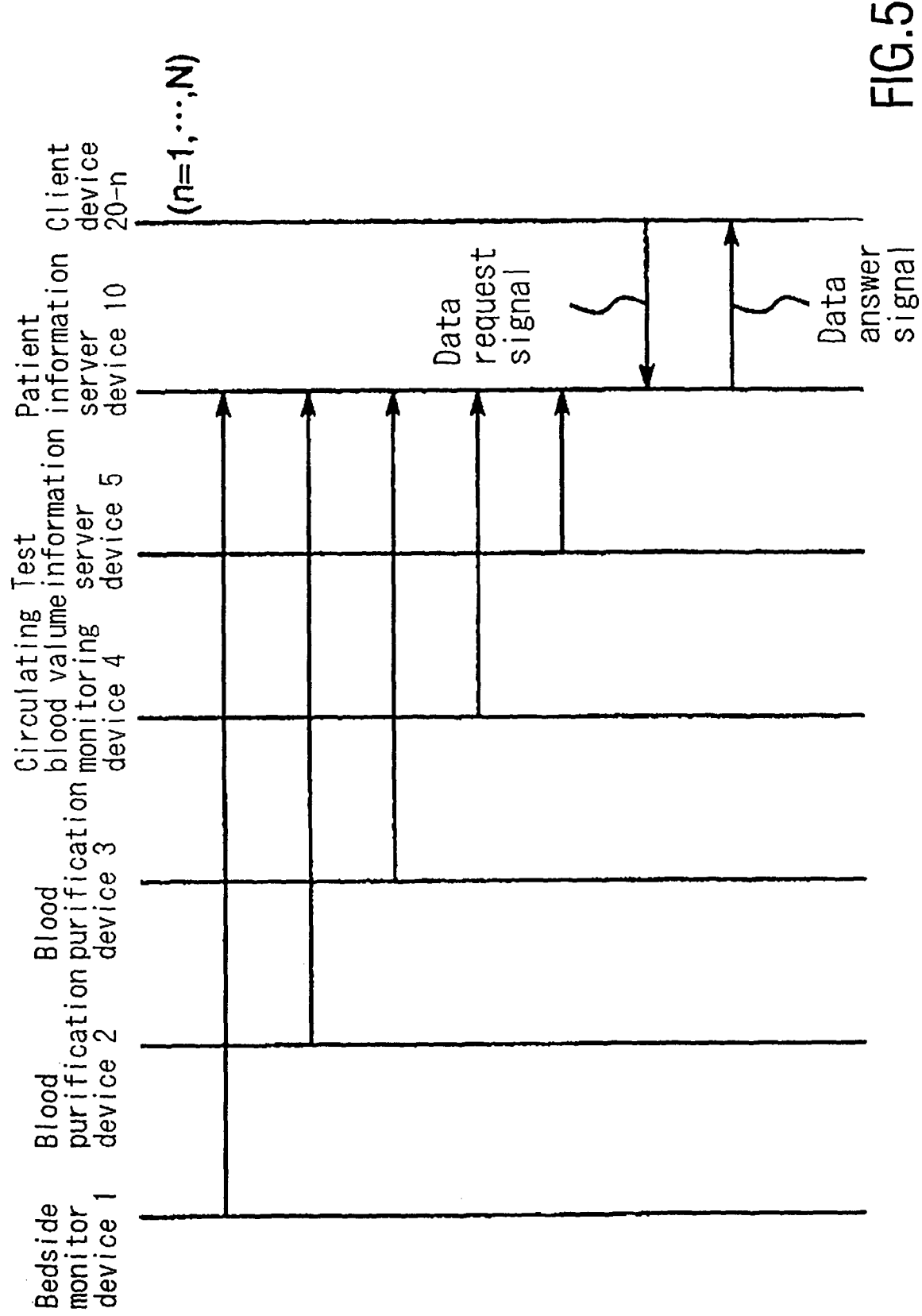
FIG. 5 is a sequence diagram showing the flow of signals between the respective devices of the management system for biological information and device information of FIG. 1.

As described above, patient information including biological information and device information from the respective devices 1 to 5 and 41 to 48 is transmitted to the patient information server device 10 as shown in FIG. 5. And the LAN 50 of FIG. 1 has further a plural number N of client devices 20-1 to 20-N (hereinafter, these are given symbol 20 in a general term) and a printer 30 shared with the client devices 20 connected to it. The patient information server device 10 receives and stores every patient information transmitted from the respective devices 1 to 5 and 41 to 48 automatically and at time intervals of one minute for example, and returns a data answer signal containing data of patient information of a patient corresponding to the relevant patient indication information to the relevant client device 20 based on a data request signal containing patient indication information from each client device 20 as shown in FIG. 5.

Further, the device link concentrator device 7 has a transfusion pump 41, a syringe pump 42, a respirator 43, a biological impedance measuring device 44, a cardiac output meter 45, an automatic uroflowmeter 46, a metabolism monitor 47 and an ultrasonograph 48 connected to it, and measurement information from the devices 41 to 48 is transmitted and stored into the patient information server device 10 through the device link concentrator device 7, the LAN 50 and the device link server device 8. For example, the transfusion pump 41 transmits the predetermined value information of transfusion quantity (per unit time) to the patient information server device 10, and the syringe pump 42 transmits the predetermined value information of the dosage (dosage at one time, or dosage per unit time) of such drug as a vasopressor, diuretic, anticoagulant, antibiotic and the like to the patient information server device 10. And the biological impedance measuring device 44 measures for example the absolute amount of water inside cells of a subject human body and the absolute amount of water outside the cells, and transmits these data to the patient information server device 10. Further the cardiac output meter 45 measures a cardiac output (l/min) through inserting a Swan-Ganz catheter into a subject human body and transmits the data to the patient information server device 10. And the automatic uroflowmeter 46 measures a urine flow per unit time and transmits the data to the patient information server device 10. Further, the metabolism monitor 47 measures a metabolic quantity per day and transmits the data to the patient information server device 10. Furthermore, the ultrasonograph 48 can perform an echocardiography or echo-abdominoscopy and transmits the data to the patient information server device 10.

On the other hand, the client device 20 transmits control signals to the transfusion pump 41, the syringe pump 42 and the respirator 43 through the LAN 50, the device link server device 8 and the device concentrator 7, and thereby controls the set value of a transfusion amount (per unit time) in the transfusion pump 41, controls the set value of a dosage (dosage at one time, or dosage per unit time) of such drug as a vasopressor, diuretic, anticoagulant, antibiotic and the like and controls a specific set value in the respirator 43.

The client device 20 transmits control signals to the blood purification devices 2 and 3 through the LAN 50, the device link server device 8 and the device concentrator 7, and thereby controls, for example, the set value of dehydration amount, the set value of flow rate and the dosage of an anticoagulant such as heparin or the like for example.

Figure 2:
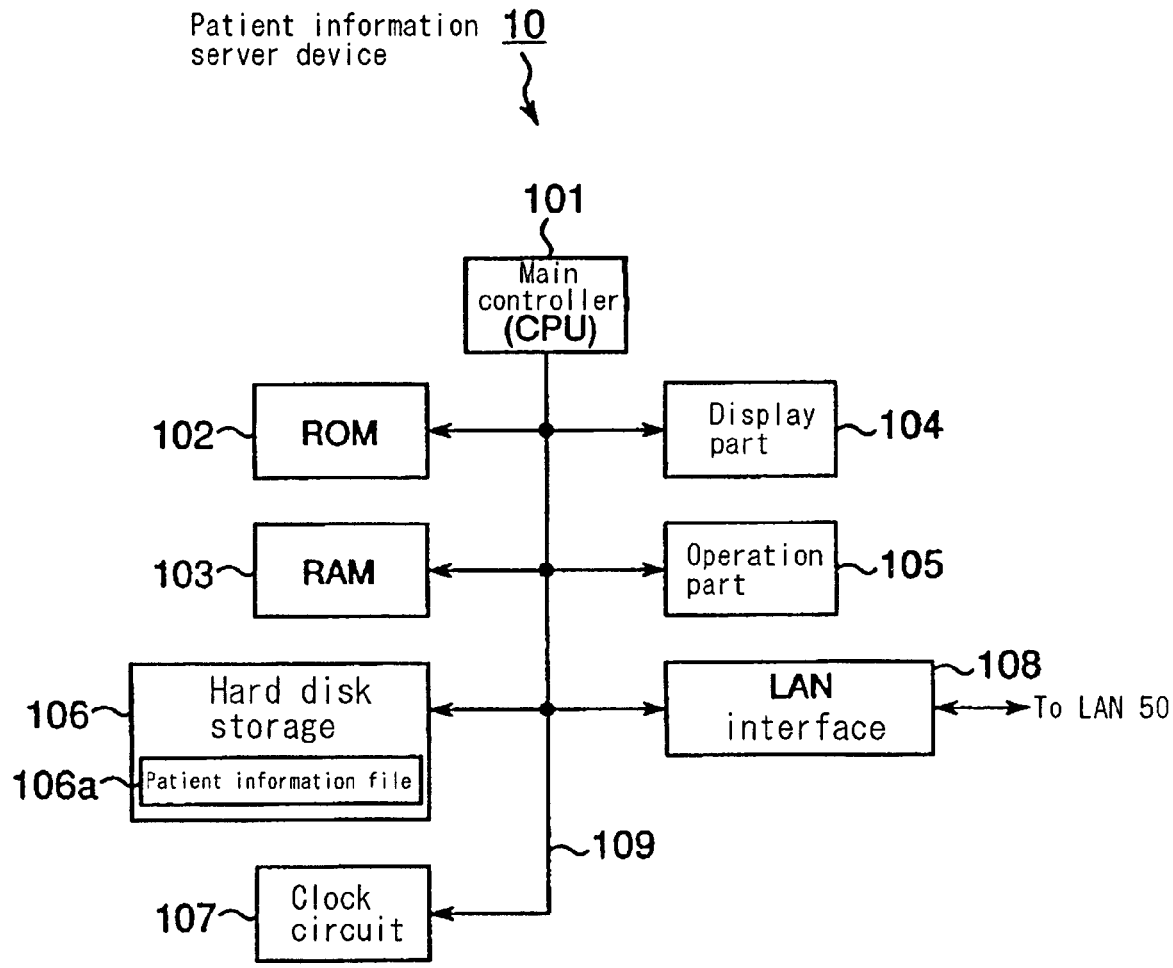
FIG. 2 is a block diagram showing a detailed composition of a patient information server device 10 of FIG. 1.

FIG. 2 is a block diagram showing a detailed composition of the patient information server device 10 of FIG. 1. In FIG. 2, the patient information server device 10 is a server device which samples, accumulates and stores automatically and periodically, at specific time intervals of one minute for example, every data of patient information transmitted from the devices 1 to 5 and 41 to 48, and returns a data answer signal including data of patient information of a patient corresponding to the relevant patient indication information to the relevant client device 20 based on a data request signal including a patient indication signal from each client device 20. A main controller 101, which is concretely composed of a CPU, is connected to the following hardware portions through a bus 109 and controls them and additionally performs various software functions described later. A ROM 102 stores various software programs in advance which are necessary for operation of the relevant patient information server device 10 and are performed by the main controller 101. And these programs may be recorded on a recording medium such as a floppy disk, MO, DVD-RAM or the like and may be loaded on a RAM 103 or a hard disk storage 106 through its driving device and then the relevant program may be executed. The RAM 103 is composed of SRAMs, is used as a working area of the main controller 101 to store temporary data generated during execution of a program.

A display part 104 is a display device such as a liquid crystal display device (LCD) or a CRT display and the like, and displays the state of operation of the relevant patient information server device 10 or displays data of patient information of a flow sheet or the like described later. The patient information server device 10 can perform also an information management system process to be performed by a client device 20 described later, and can display and print a flow sheet. And an operation part 105 includes a keyboard and a mouse, and the keyboard comprises character keys, a ten-key pad, various function keys and the like necessary for operating the relevant patient information server device 10. The above-mentioned display part 104 may be formed into a touch-sensitive screen, which may be substituted for some or all of the keys of this operation part 105. A hard disk storage 106 plays a role as a storage to store information data and a program recording medium, and includes at least a patient information file 106*a*. And a clock circuit 107 clocks the current date and hour, and outputs the current date and hour to the main controller 101 according to need. Further, a LAN interface 108 is connected to the LAN 50 and performs an interface process such as a signal conversion, a protocol conversion and the like when the main controller 101 communicates with a device connected to the LAN 50.

Figure 3:
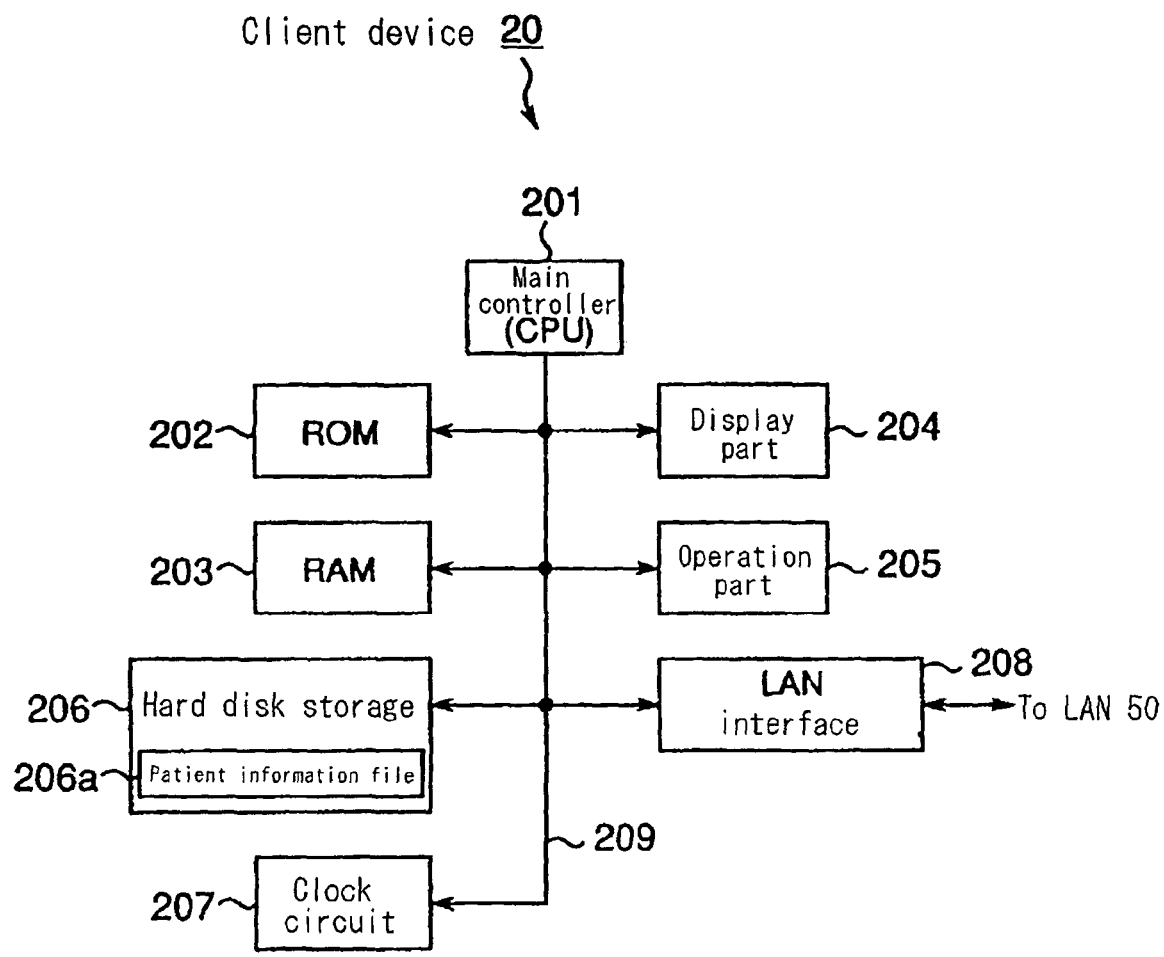
FIG. 3 is a block diagram showing a detailed composition of a client device 20 of FIG. 1.

FIG. 3 is a block diagram showing a detailed composition of a client device 20 of FIG. 1. In FIG. 3, the client device 20 accesses the patient information server device 10 by transmitting a data request signal including patient indicating information for requesting data of patient information related to a specific patient to the patient information server device 10, for example, when performing an information management system process of FIGS. 7 to 9, and receives a data answer signal including patient information data of a patient corresponding to the relevant patient indicating information returned from the patient information server device 10 based on this data request signal, and thereby downloads and stores the patient information data into a patient information file 206*a* in a hard disk storage 206 and then displays a flow sheet described in detail later on a display part 204 or outputs its data to a printer 30 through the LAN 50 to record the said flow sheet on a recording paper by printing.

In FIG. 3, a main controller 201, which is concretely composed of a CPU, is connected to the following hardware portions through a bus 209 and controls them and additionally performs various software functions described later. A ROM 202 stores various software programs in advance which are necessary for operation of the relevant client device 20 and are performed by the main controller 201. And these programs may be recorded on a recording medium such as a floppy disk, MO, DVD-RAM or the like and may be loaded on a RAM 203 or a hard disk storage 206 through its driving device and then the relevant program may be executed. The RAM 203 is composed of SRAMs, is used as a working area of the main controller 201 to store temporary data generated during execution of a program.

A display part 204 is a display device such as a liquid crystal display device (LCD) or a CRT display and the like, displays the state of operation of the relevant client device 20, or displays data of patient information of a flow sheet or the like described in detail later. Hereupon, the display part 204 may be installed not only at a patient's bedside but also in a monitor room, and may be formed out of a small-sized portable display. And an operation part 205 includes a keyboard and a mouse, and the keyboard comprises character keys, a ten-key pad, various function keys and the like necessary for operating the relevant client device 20. The above-mentioned display part 204 may be formed into a touch-sensitive screen, which may be substituted for some or all of the keys of this operation part 205. A hard disk storage 206 plays a role as a storage to store information data and a program recording medium, and includes at least a patient information file 206a for temporarily storing data of patient information included in a data answer signal received from the patient information server device 10. And a clock circuit 207 clocks the current date and hour, and outputs the current date and hour to the main controller 201 according to need. Further, a LAN interface 208 is connected to the LAN 50 and performs an interface process such as a signal conversion, a protocol conversion and the like when the main controller 201 communicates with a device connected to the LAN 50.

Figure 4:
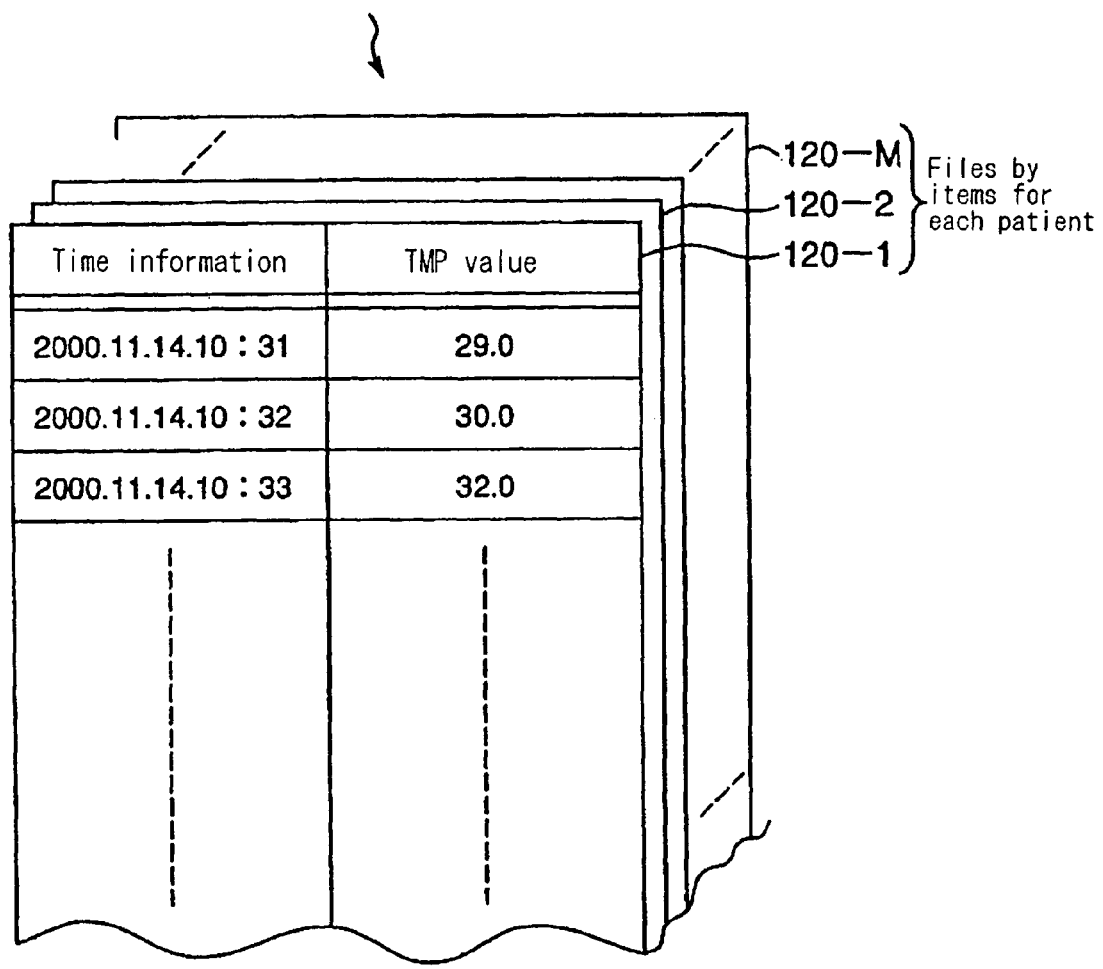
FIG. 4 is a figure showing an example of the file composition of a patient information file 106a in a hard disk storage 106 of FIG. 2.

FIG. 4 is a figure showing an example of the file structure of a patient information file 106a in the hard disk storage 106 of FIG. 2, and the patient information file 206a of FIG. 3 has also a similar file structure. As shown in FIG. 4, the patient information file 106a is partitioned for each patient and includes files 120-1 to 120-M each corresponding to a patient which are classified by items. For example, the first file 120-1 by items has data of a TMP value (a transmembrane pressure from a blood purification device 2 or 3 as described later) and the like corresponding to the time information stored in it.

Figure 6:
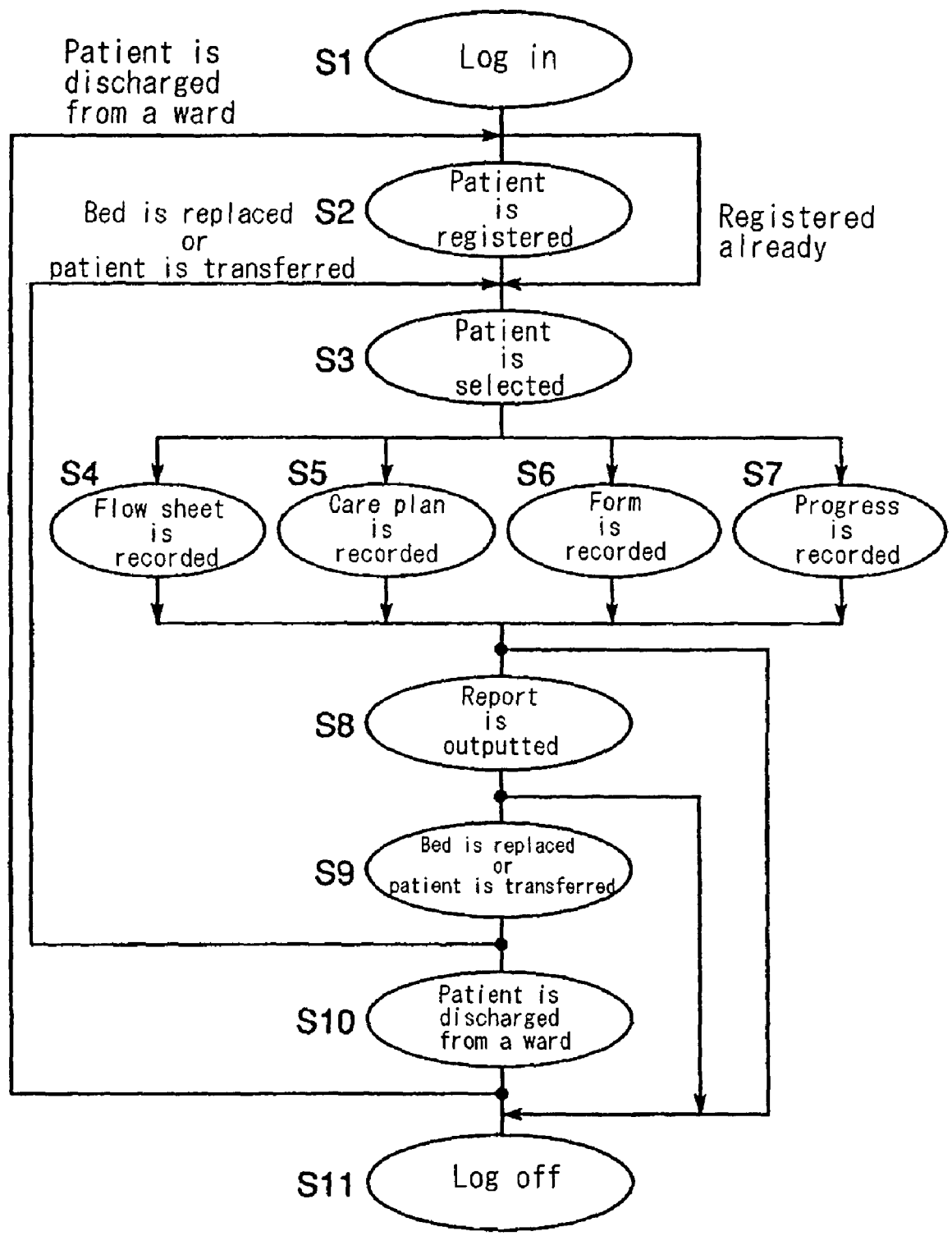
FIG. 6 is a flowchart showing roughly the flow of operation of the management system for biological information and device information.

FIG. 6 is a flowchart showing roughly the flow of operation of a management system for biological information and device information of FIG. 1. When executing an application of an information management system process, the system logs in to the patient information server device 10 (step S1) and then performs a process of registering a patient (step S2) when the patient has not yet been registered and proceeds to a patient selection process of step S3. On the other hand, if the relevant patient has been already registered, the system simply proceeds to a patient selection process in step S3. In step S3, the system selects a patient whose patient information is desired to display from a patient list and then performs at least one of the following processes.

(1) Recording a flow sheet in step S4: including processes of displaying a flow sheet, inputting and setting data on the flowchart, and the like.
(2) Recording a care plan in step S5: including processes of displaying a sheet, inputting and setting data regarding the nursing plan for a patient.
(3) Recording a form in step S6: including a process of setting a format in the relevant management system.
(4) Recording a progress record in step S7: including displaying and inputting the progress recording note of a patient.

Next the system proceeds to step S8 or logoff of step S11. In step S8, the system performs a process of print-recording a report in sheet such as a flow sheet by means of a printer 30. Next, the system proceeds to a process of step S11 or S9. In step S9, when a patient is changed in bed or is transferred, the system returns to step S3 or proceeds to step S10. In step S10, the system performs a patient discharging process and then proceeds to step S2 or logoff of step S11.

Figure 7:
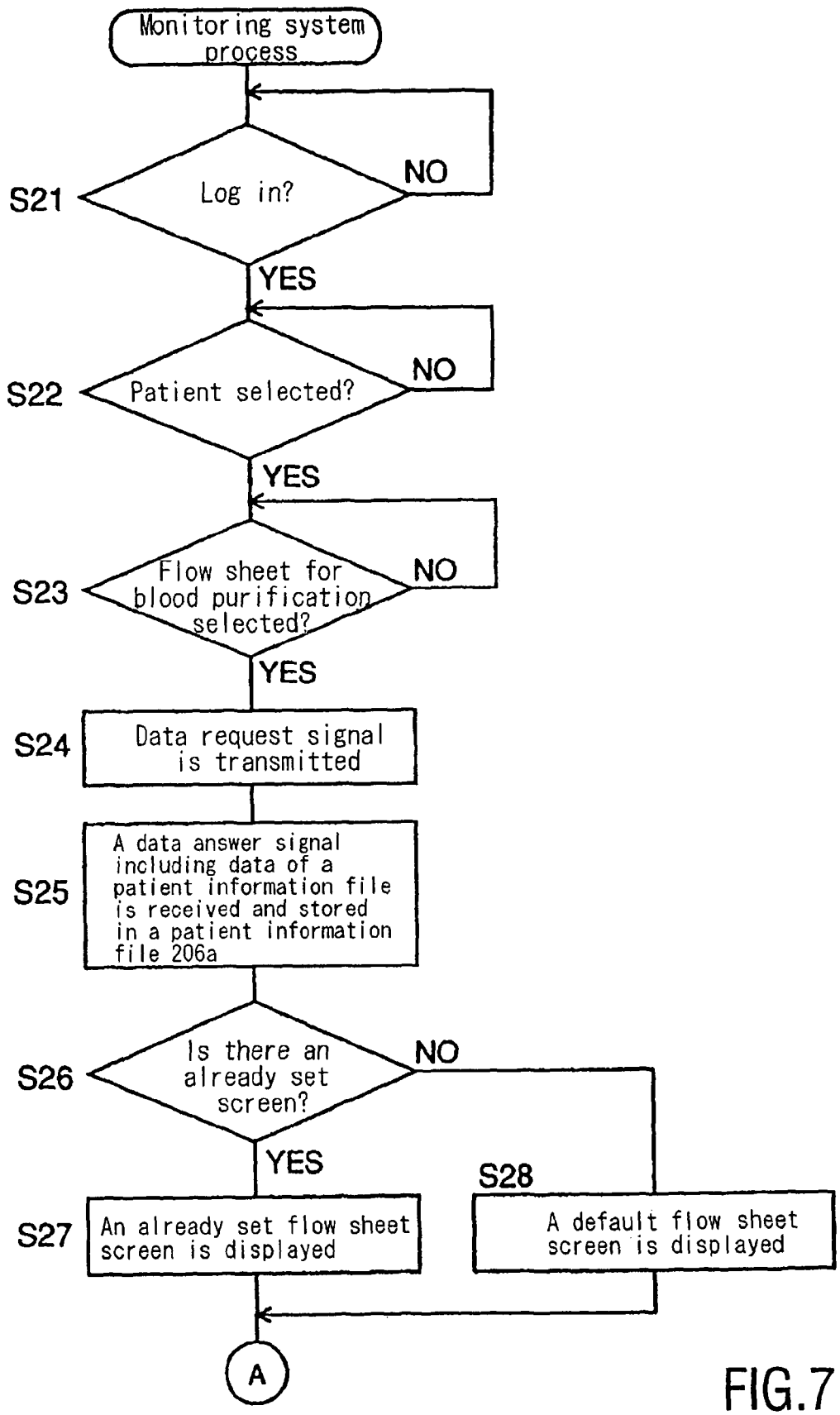
FIG. 7 is a flowchart showing a first part of an information management system process to be performed by a main controller 201 of a client device 20 of FIG. 1.
Figure 8:
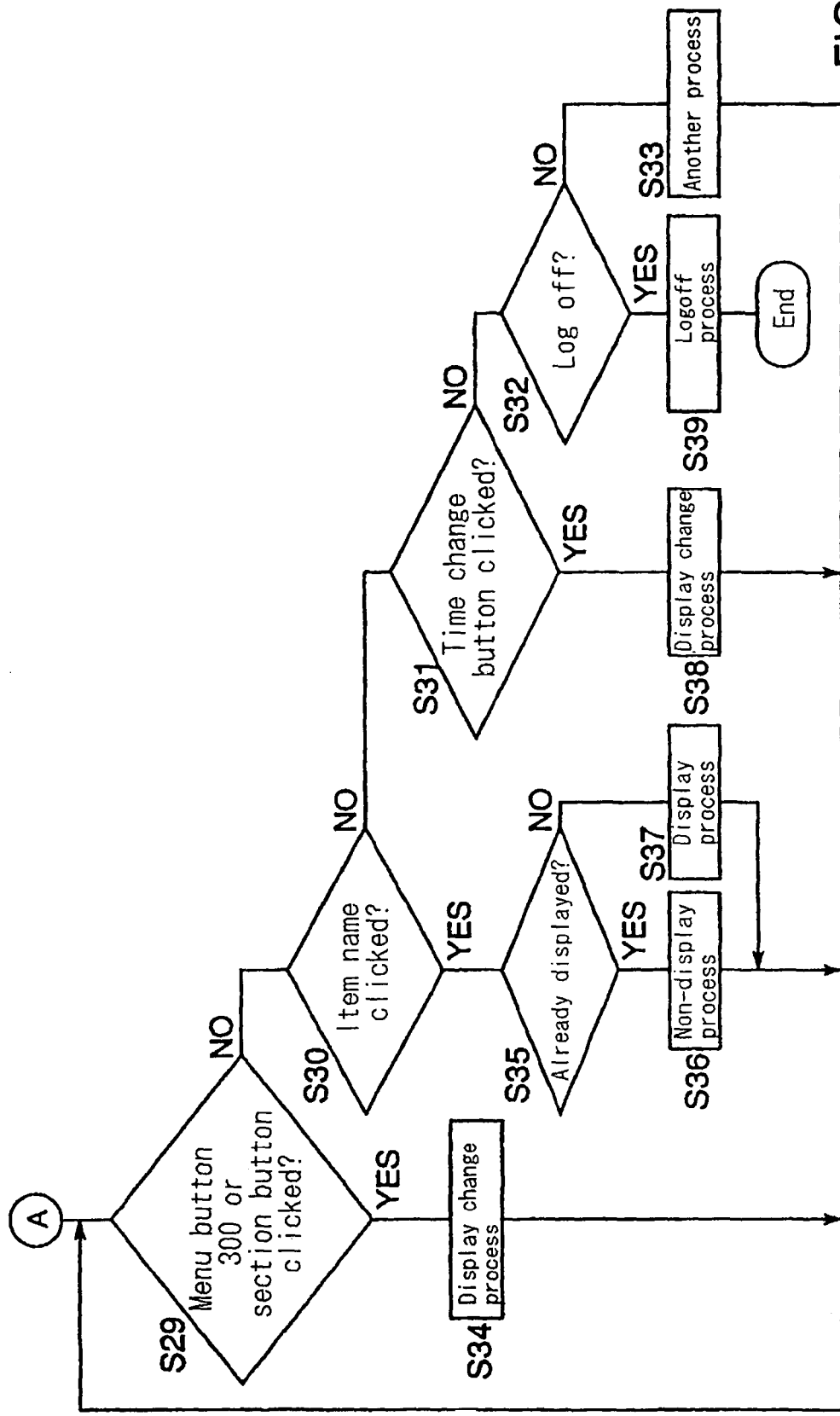
FIG. 8 is a flowchart showing a second part of the information management process to be performed by the main controller 201 of the client device 20 of FIG. 1.

FIGS. 7 and 8 are a flowchart showing an information management system process performed by the main controller 201 of the client device 20 of FIG. 1. These FIGS. 7 and 8 show a part of an outline of an information management system process. And the following description refers to a display arrangement example of a flow sheet for blood purification of FIG. 10. Therefore, FIG. 10 is explained prior to explaining FIGS. 7 and 8.

Figure 10:
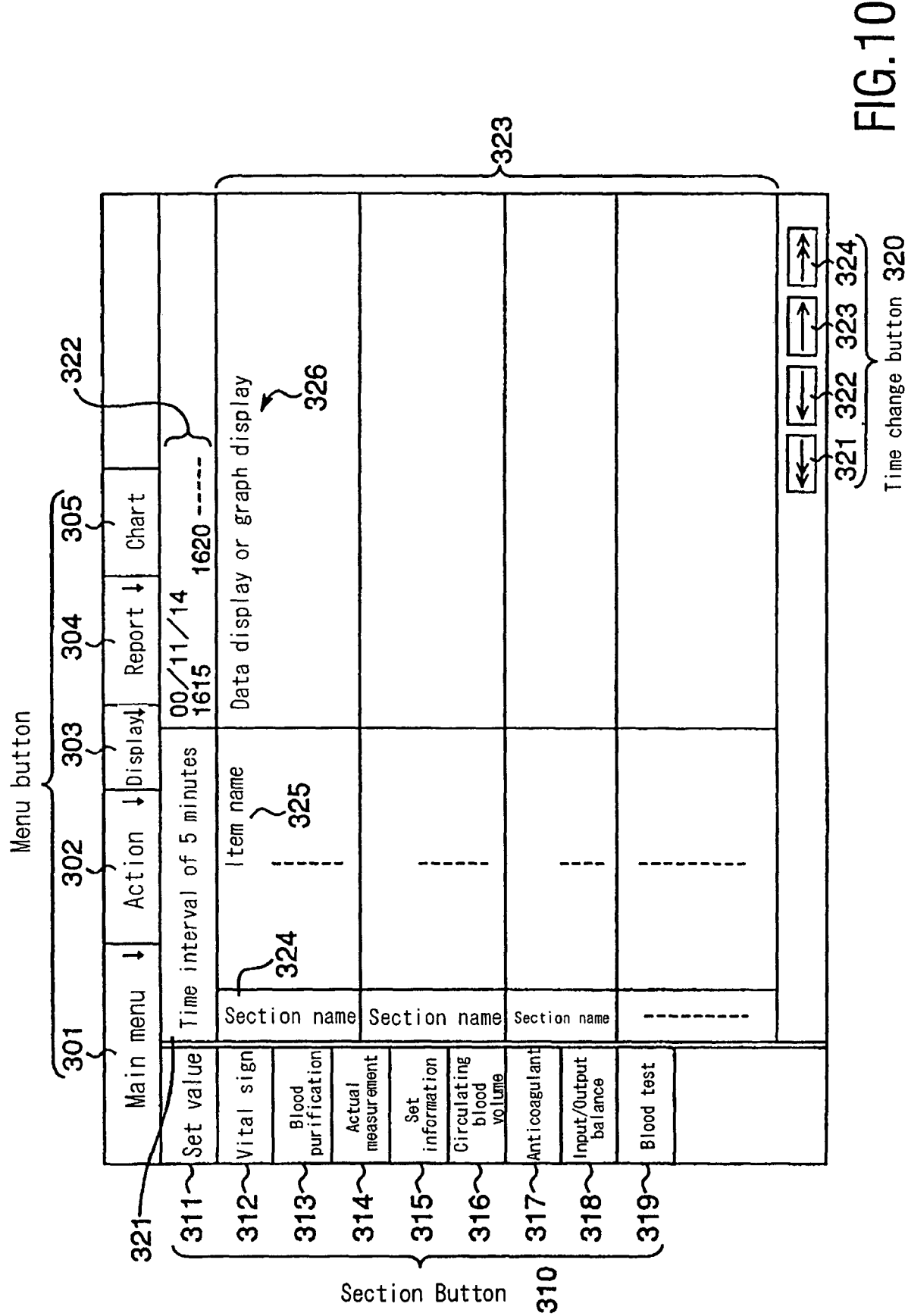
FIG. 10 is a figure showing a display arrangement example of a flow sheet for blood purification to be displayed in the client device 20 of FIG. 1.

FIG. 10 is a display arrangement example of a flow sheet for blood purification of FIG. 10 to be displayed on the display part 204, and has a menu button bar 300 including a main menu 301, action 302, display 303, report 304 and chart 305 displayed and arranged on the left top of a screen. At the left end under the menu button bar 300, nine section buttons 310 for selecting a section being a major item of patient information are arranged and the section buttons 310 include a set value 311, vital sign 312, blood purification 313, actual measurement 314, setting information 315, circulating blood volume 316, anticoagulant 317, intra-/extra-cellular water balance (balance between the intra- and extra-cellular contents of bodily water) 318 and blood test 319. Hereupon, the set value 311 is a section to display numerically the device setting value of the blood purification device 2 or 3, the vital sign 312 is a section to numerically display a measurement value of the bedside monitor device 1, and the blood purification 313 is a section to display a chronological graph called a chart showing the device setting value and measurement value of the blood purification device 2 or 3 and the measurement value of the circulating blood volume measuring device 4. Concrete examples of it are shown in FIGS. 20 to 27. And the actual measurement 314 is a section to numerically display an actual measurement value of the blood purification device 2 or 3, and the setting information 315 means flow rate information and is a section to numerically display flow rate information measured by the blood purification device 2 or 3 and device setting information. Further, the circulating blood volume 316 is a section to numerically display the measurement value of the circulating blood volume measuring device 4, and the anticoagulant 317 is a section to numerically display data manually inputted using the operation part 205 with regard to the amount of anticoagulant administered to the relevant patient. And further, the intra-/extra-cellular water balance 318 is a section to numerically display data of input, output and balance of water in the relevant patient, and the blood test 319 is a section to numerically display test information inputted and stored in the test information server device 5.

Further, a display area 321 to display a time interval for automatic recording is arranged at the left top of the right side of the section buttons 310, and time information 322 is arranged at the right side of it. And a display area 323 to display patient information is arranged at a large area under the right side of it, and this display area 323 includes section names 324, item names 325 being small items, and data displays or graph displays 326. Hereupon, the data displays or graph displays 326 each perform a chronological display corresponding to time information, and while the data display displays the numerical data of patient information, the graph display displays a broken line graph called a chart or a discrete graph using marks corresponding to item names. Further, time display change buttons 320 are arranged at the left bottom of the screen, and these time display change buttons 320 include the following four buttons from the left.

(1) 321: A button used for changing to data of the previous patient information outside the time range of the current display screen.
(2) 322: A button used for changing to data of patient information so as to move to the time being one time interval earlier in the time range of the current display screen.
(3) 323: A button used for changing to data of patient information so as to move to the time being one time interval later in the time range of the current display screen.
(4) 324: A button used for changing to data of the following patient data outside the time range of the current display screen.

Next, an information management system process shown in FIGS. 7 and 8 is described with reference to FIG. 10.

In FIG. 7, it is first judged in step S21 whether or not the system has logged in, and a process of step S1 is repeated until the system logs in, and when YES is obtained it is judged in step S22 whether or not the system has selected a patient, and when YES is obtained it is judged in step S23 whether or not a flow sheet for blood purification has been selected. As described in detail later, a flow sheet for blood purification is selected when a user clicks main menu 301 out of menu buttons 300 and clicks a patient data record and a flow sheet for blood purification on the flow sheet screen of FIG. 10. Next, in step S24 the system transmits a data request signal including patient indicating information for identifying the selected patient to the patient information server device 10. In response to this, in step S25 the system receives and stores a data answer signal including data of a patient information file transmitted from the patient information server device 10 into a patient information file 206a. And it is judged in step S26 whether or not there is an already set screen and when YES is obtained the system displays an already set flow sheet (which means a flow sheet including a section, item and the like already set) screen in step S27 and proceeds to step S29 of FIG. 8. On the other hand, when NO is obtained in step S26 the system displays a default flow sheet (which means a flow sheet including a specific section, item and the like set in default) screen in step S28 and proceeds to step S29 of FIG. 8.

In step S29 of FIG. 8, it is judged whether or not a menu button 300 or a section button has been clicked, and when NO is obtained it is judged in step S30 whether or not an item name 325 has been clicked, and when NO is obtained it is judged in step S31 whether or not a time change button 320 has been clicked. When NO is obtained in step S31 it is judged in step S32 whether or not the system has logged off, and when YES is obtained the system performs a logoff process to the patient information server device 10 in step S39 and ends this information management system process. On the other hand, when NO is obtained in step S32, another process is performed in step S33 and thereafter the system returns to step S29.

When YES is obtained in step S29, a display change process is performed in step S34. Hereupon, when a menu button 300 has been clicked the system displays a process corresponding to it. And when a section button has been clicked a section corresponding to one of buttons 311 to 319 and its patient information data are displayed on the display area 323. When one of buttons 311 to 319 corresponding to an already displayed section has been clicked, the display in the patient information display area 323 regarding the corresponding section and its patient information data is erased. After performing a process of step S34, the system returns to step S29. And when YES is obtained in step S30, it is judged in step S35 whether or not the item name has been already displayed, and when YES is obtained the system performs a non-display process in step S36, displays thinly the clicked item name, makes the corresponding data display or graph display 326 undisplayed and returns to step S29. On the other hand, when NO is obtained in step S35, the system performs a display process in step S37, displays thickly the clicked item name and displays the data display or graph display 326 corresponding to it, and returns to step S29.

Further, when YES is obtained in step S31, the system performs a display change process in step S38, namely, changes the current screen to a screen of a time range corresponding to one of buttons 321 to 324 of the time change buttons 320 and then returns to step S29. When the client device 20 has a small memory capacity in RAM 203 and cannot have every patient information regarding a patient downloaded from the patient information server device 10, the system may download and store only patient information data in a specific time range around the current time of interest into a patient information file 206a, and when some of buttons 321 to 324 of the time change buttons 320 has been clicked, the system may send a data request signal in order to download data which does not exist in the patient information file 206a from the patient information server device 10.

Figure 9:
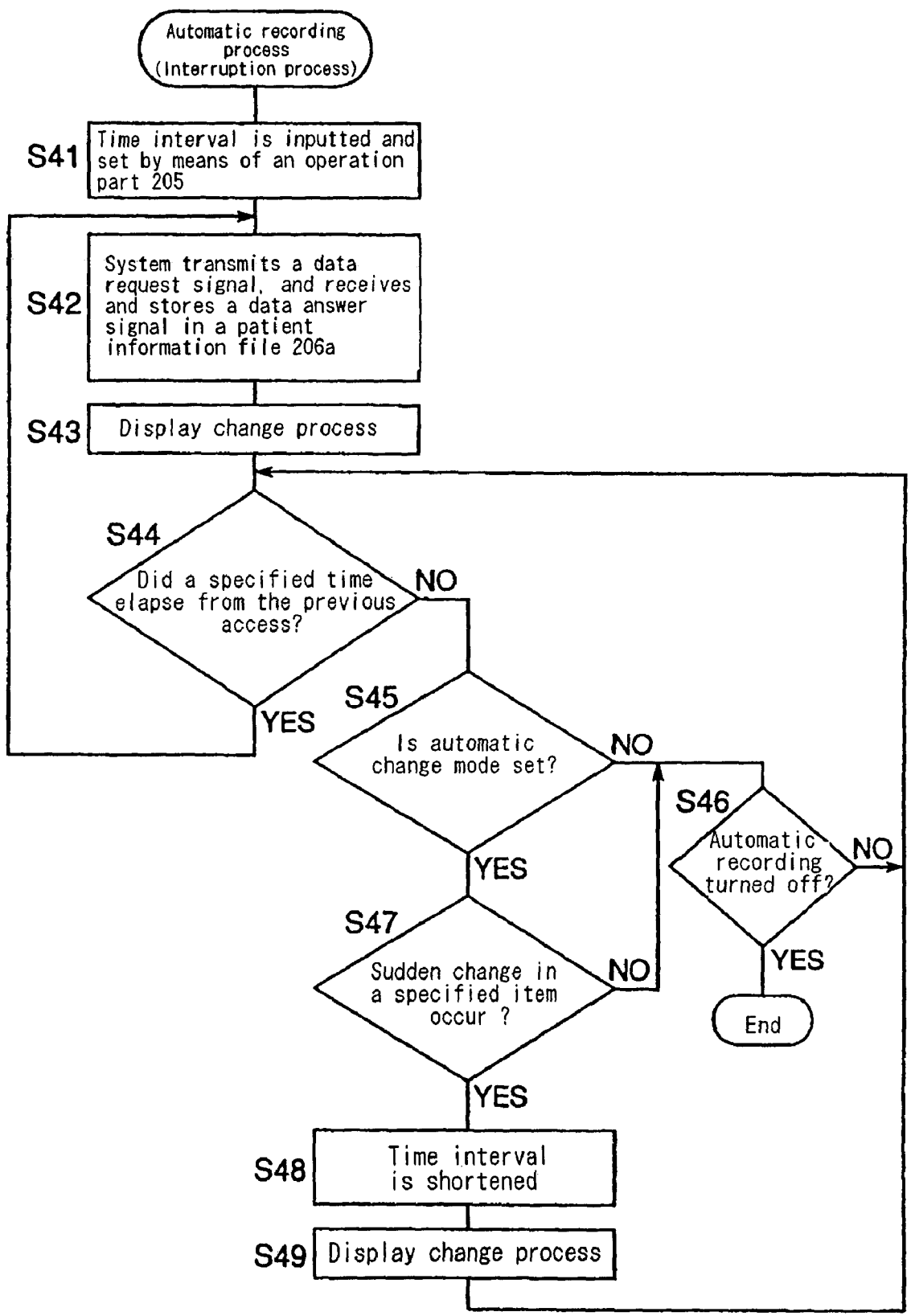
FIG. 9 is a flowchart showing an automatic recording process being an interruption process to be performed by the main controller 201 of the client device 20 of FIG. 1.

FIG. 9 is a flowchart showing an automatic recording process being an interruption process to be performed by the main controller 201 of the client device 20 of FIG. 1, and the automatic recording process is a process for downloading patient data newly recorded by the patient information server device 10 at specific time intervals from the patient information server device 10 into a patient information file 206a of the client device 20 and displaying the downloaded patient data, and the automatic recording process of FIG. 9 is performed when action 302 and automatic recording are clicked. On the other hand, when automatic recording is turned off in this automatic recording process, the system sends a data request signal to the patient information server device 10 and displays or records only patient data included in a data answer signal transmitted from the patient information server device 10 in response to this data request signal in the form of a flow sheet in a specific time range.

Figure 12:
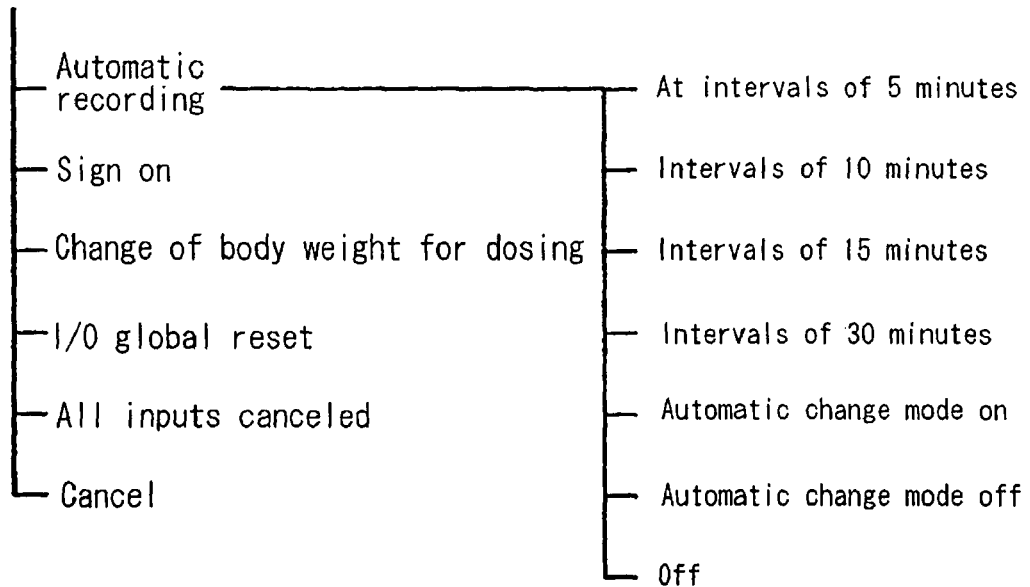
FIG. 12 is a table showing items to be branched by clicking action 302 in the flow sheet for blood purification of FIG. 10 with the mouse.

In the automatic recording process of FIG. 9, first a user inputs and sets a time interval for automatic recording by means of the operation part 105 (this setting can be set after clicking action 302 and automatic recording) in step S41, and the system transmits a data request signal to the patient information server device 10 in step S42, receives a data answer signal from the patient information server device 10 in response to this data request signal and stores patient information data included in the received data answer signal into the patient information file 206a. And in step S43, the system performs a display change process to display the newly stored data. Hereupon, the system shifts the time range to be displayed on the flow sheet screen toward the current time and displays the new patient information data and thus data being older in time comes to disappear from the display. Next, it is judged in step S44 whether or not the set time interval has passed since the previous access and when YES is obtained the system returns to step S42 and performs transmission/reception of new patient data and a display change process. On the other hand, when NO is obtained in step S44, it is judged in step S45 whether or not an automatic change mode has been set (as shown in FIG. 12, after action button 302 and automatic recording are clicked, the automatic change mode is turned on when the automatic change mode on is clicked but it is turned off when the automatic change mode off is clicked), and when NO is obtained it is judged in step S46 whether or not automatic recording has been turned off (this setting can be set after action 302 and automatic recording are clicked), and the system ends this automatic recording process when YES is obtained but the system returns to step S44 when NO is obtained. And when YES is obtained in step S45, it is judged in step S47 whether or not an sudden change has occurred in a specific item, and when YES is obtained the time interval is changed in step S48 so as to be made shorter after the sudden change has occurred, and a display change process is performed in step S49.

That is to say, the system displays patient information data so as to change the time interval of patient information on the flow sheet screen to be shorter. Hereupon, the judgment in step S47 makes the system automatically display the data at time intervals of 1 minute instead of time intervals of 15 minutes, for example, when a TMP value suddenly rises at a change rate of 10% or more.

In steps S47 to S49 in FIG. 9, when a patient is suddenly changed in condition the system changes the time interval to become shorter at which the client device 20 accesses the patient information server device 10, but the present invention is not limited to this but may change the time interval to be shorter at which the client device 20 accesses the patient information server device 10 when a patient comes into a stable stage (for example, it is judged as a stable stage when numerical values of specific items are kept in a specific range for a specific long time).

Although the preferred embodiment described above changes the time interval, the present invention is not limited to this but may perform automatically processes of steps S42 and S43 at plural specified points of time. This concrete example is described in detail later.

In the preferred embodiment described above, the patient information server device 10 accumulates and stores biological information from the devices 1 to 5 and 41 to 48 together with time information at specific time intervals of, for example, one minute into a patient information file 106a, but the system may be composed so that this setting of time interval can be changed by the client device 20. And in steps S47 to S49 of FIG. 9, the time interval at which the client device 20 accesses the patient information server device 10 is changed at a sudden change in condition of a patient or in a stable stage, but similarly to this the time interval at which the patient information server device 10 stores information from the devices 1 to 5 and 41 to 48 may be changed at a sudden change in condition of a patient or in a stable stage.

Figure 28:
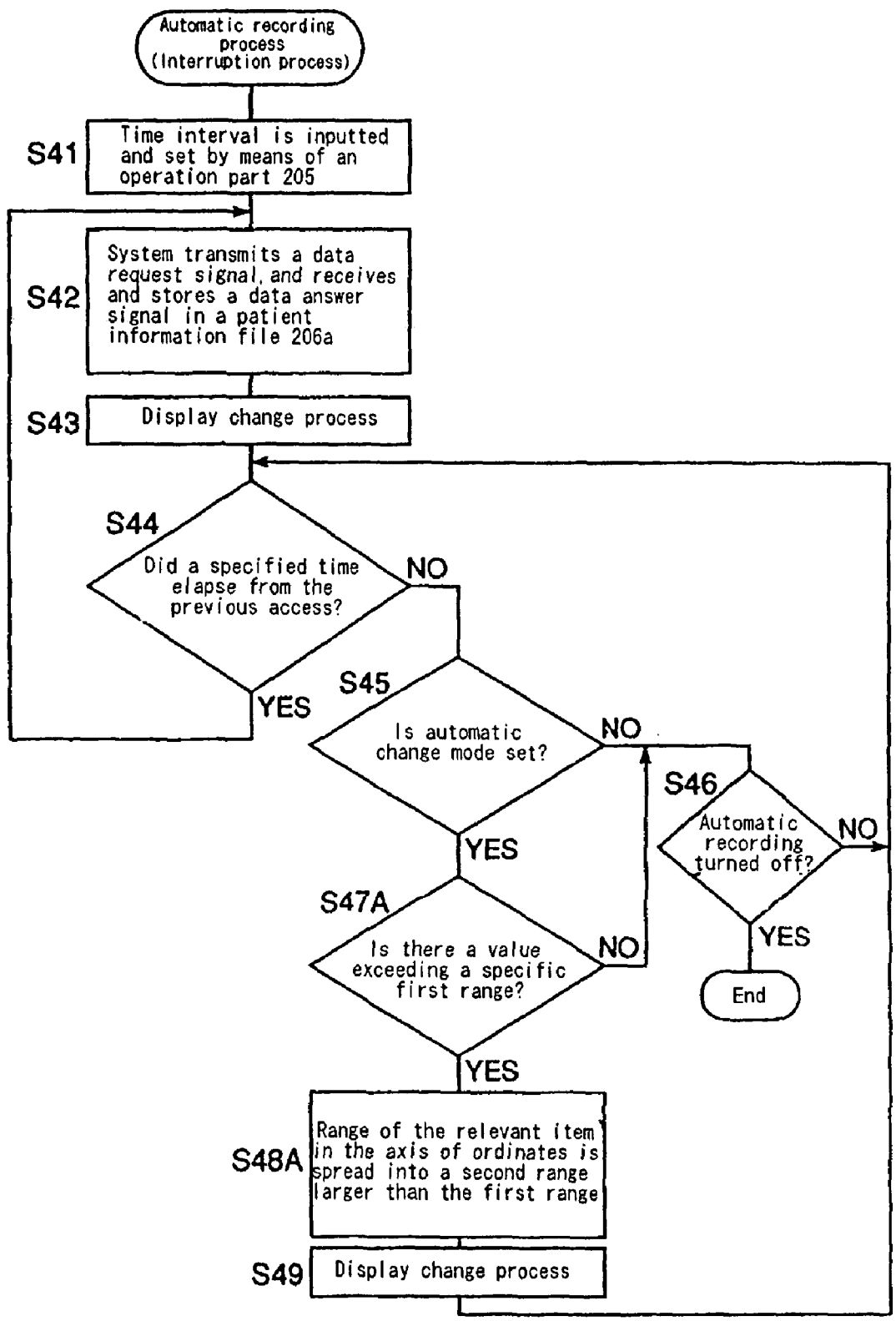
FIG. 28 is a flowchart showing a variation example of an automatic recording process being an interruption process illustrated in FIG. 9.

FIG. 28 is a flowchart showing a variation example of an automatic recording process being an interruption process illustrated in FIG. 9. It is in the following points that a control flow of FIG. 28 is different from the control flow of FIG. 9.

(1) In place of step S47, step S47A "it is judged whether or not there has been a value exceeding a first specific range" is provided.

(2) In place of step S48, step S48A "the range of the relevant item in the axis of ordinates is changed so as to be spread into a second range larger than a first range" is provided.

For example, when the range of displayed values of a hematocrit value in the display part 204 (the axis of ordinates) is ±25, for example in case that a hematocrit value of +27 is observed, the change in display scale is performed so as to automatically spread a range of ±25 of displayed values (the axis of ordinates) to a range of ±50. This change in display scale may not be performed by an automatic change mode but may be set by providing "hematocrit value ±25" and "hematocrit value ±50" in section buttons 310 shown in FIG. 10, clicking these buttons and thereby manually and selectively changing over displaying a measured hematocrit value in a display scale of ±25 or displaying a measured hematocrit value in a display scale of ±50 from one to the other.

An example of FIG. 28 as described above changes a display scale so as to spread to a larger range, but the present invention is not limited to this but may change the display scale so as to come into a smaller range when a hematocrit value becomes smaller. The change in time interval of FIG. 9 and the change in display scale of FIG. 28 may be performed at the same time, and only one of them may be performed.

Figure 11:
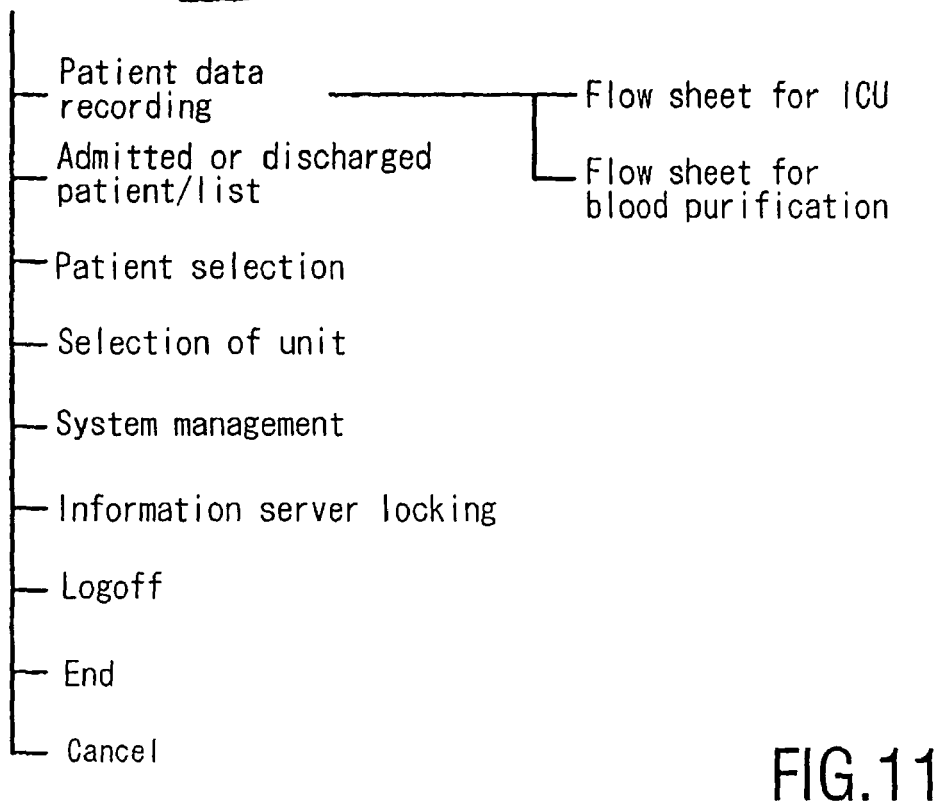
FIG. 11 is a table showing items to be branched by clicking main menu 301 in the flow sheet for blood purification of FIG. 10 with a mouse.

FIG. 11 is a table showing items to be branched when clicking main menu 301 in a flow sheet for blood purification of FIG. 10 with a mouse. In FIG. 11, when main menu 301 is clicked, the following items are displayed and when the following item names are clicked the following processes are performed.

(1) Patient data recording: is a process for displaying and recording various flow sheets.

(2) Patient's admission to or discharge from a ward/list: is a process performed when a patient is admitted to or discharged from a ward and a process for outputting a patient list.

(3) Selecting a patient: is a process for selectively specifying a patient when displaying a flow sheet.

(4) Selecting a unit: is a process for selecting a blood purification device 2 or 3 for example.

(5) Management of a system: is a process for changing the specifications of the relevant system.

(6) Locking an information server: is a process for performing an action to the patient information server device 10.

(7) Logoff: is a process for logging off with regard to the patient information server device 10.

(8) End: is a process for ending an application of the relevant information management system process.

(9) Cancel: is a process for canceling the display of the relevant main menu 301.

Hereupon, when clicking the above patient data recording, the following two items are displayed, and when clicking an item name, the following processes are performed.

(1) Flow sheet for ICU: is a process for displaying or recording a flow sheet for an emergency room.

(2) Flow sheet for blood purification: is a process for displaying or recording a flow sheet for blood purification.

FIG. 12 is a table showing items to be branched when clicking action 302 in a flow sheet for blood purification of FIG. 10 with a mouse. In FIG. 12, when action 302 is clicked, the following items are displayed and when the following item names are clicked the following processes are performed.

(1) Automatic recording: This automatically accesses the patient information server device 10, automatically stores and records patient information data from the patient information server device 10 into a patient information file 206a, and sets whether or not a flow sheet is to be displayed. And when automatic charting is on, it sets its time interval.

(2) Sign on: This sets whether or not the confirmation of a password when saving inputted data is omitted.

(3) Change in body weight at dose: This changes the weight necessary for calculating a dosage.

(4) I/O global reset: This resets an input/output water balance at an optional time.

(5) Cancellation of all inputs: This cancels all operations before pressing a save button.

(6) Cancel: This closes the action menu.

When automatic recording is clicked, the following item names are displayed and the time interval of automatic recording can be changed.

(1) Time interval of 1 minute (2) Time interval of 5 minutes (3) Time interval of 10 minutes (4) Time interval of 15 minutes (5) Time interval of 30 minutes (6) Automatic change mode on: This sets a mode of automatically changing a time interval (corresponds to processes of steps S45 to S49 of FIG. 9).

(7) Automatic change mode off: This cancels a mode of automatically changing a time interval.

(8) Off: This turns off automatic recording.

FIG. 13 is a table showing items to be branched when clicking display 303 in a flow sheet for blood purification of FIG. 10 with a mouse. In FIG. 13, when display 303 is clicked, the following item names are displayed and the following processes are performed by clicking the item names.

(1) Registration time: This displays a flow sheet with the current time at the right end so as to display every patient information data.

(2) Interval of 1 minute: The following time intervals are the time intervals at which a flow sheet is automatically displayed.
(3) Interval of 5 minutes
(4) Interval of 15 minutes
(5) Interval of 30 minutes
(6) Interval of 1 hour
(7) Interval of 2 hours
(8) Interval of 4 hours
(9) Interval of 8 hours
(10) Interval of 12 hours
(11) Interval of 24 hours
(12) Standard characters: These are displayed in a standard font, and thereby the amount of data capable of being displayed at a time is made large.
(13) Magnified characters: These are displayed in a comparatively large font, and thereby the amount of data capable of being displayed at a time is made smaller.
(14) Cancel: This closes the display menu.

FIG. 14 is a table showing items to be branched when clicking report 304 in a flow sheet for blood purification of FIG. 10 with a mouse. In FIG. 14, when report 304 is clicked, the following item names are displayed and the following processes are performed by clicking the item names.
(1) Flow sheet for ICU: This print-records the same flow sheet as a flow sheet for ICU to be displayed using a printer 30.
(2) Flow sheet for blood purification: This print-records the same flow sheet as a flow sheet for blood purification to be displayed using a printer 30.

FIG. 15 is a table showing items to be branched when clicking chart 305 in a flow sheet for blood purification of FIG. 10 with a mouse. In FIG. 15, when chart 305 is clicked, the following item names are displayed and the following processes are performed by clicking the item names.
(1) Addition of item: This adds an item to be displayed in a flow sheet.
(2) Deletion of item: This deletes an item being displayed in the current flow sheet.
(3) Save: This saves patient information data temporarily stored in a patient information file 206a including the currently displayed data as authenticated flow sheet data.

Although this preferred embodiment stores data of a flow sheet into a hard disk storage 206 of the client device 20 in the save described above, the present invention is not limited to this but may store the data into a hard disk storage 106 of the patient information server device 10.

Objects and effects of the above-mentioned displaying or recording of a flow sheet for blood purification are as follows, for example.
(1) It is possible to find in an early stage abnormal conditions (hypotension, convulsion, consciousness disorder and the like) following hypovolemia, which is a complication appears in general, caused by excessive dehydration during blood purification.
(2) It is possible to predict occurrence of symptoms of hypovolemia during a dialyzing operation and grasp the variation in blood circulation by graphing hematocrit values, change in circulating blood volume and vital signs.
(3) It is possible to know the correlation between a change in circulating blood volume and set values, and perform a proper blood purification method.
(4) It is possible to grasp at a glance the correlation among hematocrit values, change in circulating blood volume, transmembrane pressure (TMP), and anticoagulant.
(5) It is possible to know a change in TMP value with the passage of time.
(6) It is possible to grasp the relation among a hematocrit value, a change in blood volume, a vital sign and water balance and perform a humor control.
(7) In case of performing blood purification at several times on the same patient, it is possible to perform an effective treatment by making proper settings through accumulating information of the above items (1) to (6).
(8) It is possible to evaluate a blood circulation behavior and select a proper blood purification method on the basis of pulmonary arterial pressure (PA), central venous pressure (CVP), mean arterial pressure (MAP), cardiac index (CI), heart rate (HR) and the like.
(9) It is possible to utilize flow sheets in education of a medical trainee.
(10) It is possible to perform a proper patient management by setting new index values.

Next, items of biological information and device information to be displayed in a flow sheet are described in detail. In this preferred embodiment, it is possible to input these information not only automatically but also manually using a keyboard or a mouse for example, and input a large amount of information. Examples of manual input are as follows.
(1) Device information of blood treatment: The kind or lot number of a filter, the state of deterioration of a filter at an end and the like.
(2) Information of a device not connected online: Body weight, activated clotting time, cytokine concentration and the like.
(3) Information examined by a person engaged in medical treatment (medical examination information): Consciousness level, psychic condition, state of hemorrhagic stigma and the like.
(4) Therapeutic information: Kind or dosage of transfusion, kind or dosage of medicine, dosage of oxygen of an oxygen mask and the like.
(5) Operation information: Blood-collecting time, safety check during treatment, management of troubles, and the like.

And in this preferred embodiment, inputted information can be modified also by manual input by an administrator (doctor, clinical engineer, nurse and the like). Due to this, it is possible to correct unnecessary information or erroneous information inputted. For example, there is an example of bloody arterial pressure measured during collection of blood through an arterial blood line.

In this preferred embodiment, it is possible to continuously record various information during treatment in hospital for a period of inputting information into the patient information server device 10 and recording it into the patient information file 106a. It is possible to record continuous information for a period of 24 hours for example and the like including a period of performing no blood treatment (a state where the power source of a blood-treating device is off). A conventional example has recorded information only when a blood treatment is intermittently performed. And this preferred embodiment makes it possible to input and store information of blood treatment at plural times. According to a management system of the above preferred embodiment, it is possible to utilize the feedback of information. In a conventional example, when one blood treatment ends and the power is turned off, the information has disappeared.

In this preferred embodiment, it is possible to set and select the time interval of automatic recording, and information is automatically inputted and saved in the patient information server device 10 at intervals of 1 minute at shortest, for example. As shown below, the system may be composed so that clicking a specific period specifying button makes it possible to change the automatic input time during only this period. The length of a period, time of automatic recording, an index or its change rate and the range of setting can be specified in advance and can be changed also halfway.

(1) Starting time recording button: This records information every one minute for 30 minutes after starting the circuit.
(2) Setting change time recording time: This records information every one minute for 10 minutes after an operation condition has been changed.
(3) Change time recording button: This records information every one minute for 10 minutes in case that an index or its change rate specified in advance has changed outside the range of setting.
(4) Trouble time recording button: This records information every one minute for 30 minutes when a trouble has occurred.
(5) Period specification time recording button: This records information every one minute for 10 minutes in a necessary period other than the above-described periods.

The variation examples described above may be applied to displaying or recording information on a flow sheet in the client device 20.

Next, items of information to be recorded in this preferred embodiment are described in detail. This preferred embodiment can record biological information, information of blood treatment and the like at the same time. While automatically recording biological information measured by devices 1 to 5 and 41 to 48, an administrator manually inputs information of items not capable of being automatically recorded, for example using the devices 1 to 5 and 41 to 48 or the operation part 205 of the client device 20 and records the information in the patient information server device 10.

First, items of information to be measured, set or inputted in a bedside monitor device 1 are as follows.

(1) Bloodless Parameters
(1-1) Blood pressure (automatic input): Information measured by a cuff device.
(1-2) Electrocardiogram (automatic input)
(1-3) Pulse (automatic input): Information measured by means of an electrocardiogram.
(1-4) Respiration rate (automatic input):
(1-5) Arterial blood oxygen saturation (automatic input): Information measured by a pulse oximeter.
(1-6) Hematocrit value (automatic input): Information measured by a pulse oximeter.
(1-7) Bodily temperature (automatic or manual input): Information measured by a urinary bladder thermo-sensor, rectum thermo-sensor, thermometer and the like.

(2) Bloody Parameters
(2-1) Bloody arterial pressure (automatic input): Information measured by a pressure sensor of an arterial line.
(2-2) Central venous pressure (automatic input): Information measured by a pressure sensor of a central venous line.
(2-3) Index of circulation behavior (pressure information of a Swan-Ganz catheter; pulmonary arterial pressure and the like) (automatic input).

Next, items of information to be measured, set or inputted in a blood purification device 2 or 3 are as follows.

(1) Items of a ledger (manual input): This is concretely information of a used filter (kind and lot number), a blood circuit (kind and lot number), start time, end time and the like, and makes it possible to calculate a priming volume and is necessary for calculating a water balance. And in case that a side effect is reported, it is necessary to record the lot number of the used means.

(2) Set values (automatic input): These are concretely the kind and serial number of a blood purification device 2 or 3, the kind of blood treatment, the alarm set value of each parameter of the blood purification device 2 or 3, and the like, as shown in embodiments of FIG. 20 and after. These include, for example, transmembrane pressure (TMP value), arterial pressure (also referred to as the inner pressure of an arterial chamber of the circuit or the entrance pressure at the blood side), venous pressure (also referred to as the inner pressure of a venous chamber of the circuit or the exit pressure at the blood side), absorption pressure and the like.

(3) Pressure information (automatic input): This includes, concretely as shown in embodiments of FIG. 20 and after, actually measured pressure data (arterial pressure, venous pressure, filtration pressure, absorption pressure and the like) and pressure data calculated from the actually measured pressure data (transmembrane pressure (TMP value) and the like. Since the system uses a roller pump, the bloodstream and pressure in the circuit are pulsing and a regular information collection does not make clear what part the pulsing bloodstream or pressure is information coming from, but it is possible to input the means value, maximum value and minimum value by synchronizing with the roller pump or weighted-averaging the information.

(4) Flow rate information (automatic input): This includes, concretely as shown in embodiments of FIG. 20 and after, an instantaneous flow rate of blood, instantaneous flow rate of blood plasma, instantaneous flow rate of waste liquid, integrated flow rate of blood, integrated flow rate of blood plasma, integrated flow rate of waste liquid, target value of blood plasma treatment and the like. Here, the integrated flow rate is an integrated value integrated since the blood purification device 2 or 3 has started working for the relevant patient.

(5) Temperature information (automatic input): Set temperature of a calorifier, actual measured temperature of the calorifier, blood temperature of a blood outgoing line and blood temperature of a blood incoming line (these temperature information is necessary for calculating a corrected bodily temperature).

(6) In addition to the kind or dosage of anticoagulant (concentration, dosing rate and the like), the amount used (amount provided for a blood-treating device at a time), and the time of replacement are also manually inputted. Due to inputting the time of replacement, it is possible to predict or advise the next time of replacement.

(7) In addition to the kind or dosage of substituted liquid and dialyzed liquid (dosing rate and the like), the amount used (amount provided for a blood-treating device at a time), and the time of replacement are also manually inputted. Due to inputting the time of replacement, it is possible to predict or advise the next time of replacement.

(8) Alarm information (automatic input): The evaluation of safety and inspection of the device can be made possible by inputting the time when the alarm of a blood purification device 2 or 3 or a circulating blood volume measuring device 4 has sounded, the kind of alarm and the state of recovery.

(9) Trouble managing record (manual input): A matter to be recorded which has occurred in coping with a trouble is manually inputted in the blood purification device 2 or 3.

(10) Event information (manual input): Comment on treatment or the like performed during performance of a blood purification process is manually inputted.

(11) State at the end of a blood treatment (manual input): The state of deterioration of a circuit and a filter (clogging and the like caused by adhesion of protein) is manually inputted.

(12) Safety check items (checklist) (manual input): A person in charge of management of blood treatment confirms items to be regularly safety-checked and then checks these items. The safety check items are specified in advance, and can be changed before start or halfway. It is preferable to input the check items together with a personal password so as to identify the name of a checker when checking. Next, items of information to be measured, set or inputted in a circulating blood volume measuring device 4 are as follows. The following items are bloodless parameters.

(1) Hematocrit value (Ht value) (automatic input)
(2) Venous blood oxygen saturation (vSpO$_2$) (automatic input)
(3) Rate of change in circulating blood volume (ΔBV %) (automatic input): The change rate of circulating blood volume (ΔBV %) [%] can be calculated by the following expression, and the adjustment of water reduction is performed using this index.

$$\Delta BV\% = (\Delta Ht0/\Delta Htu - 1) \times 100 \tag{1}$$

Here, ΔHt0 is a change in hematocrit value Ht at the beginning of blood treatment, and ΔHtu is a change in Ht at the time of measurement. This information is used also for calculating the distribution of bodily water described later.

(4) Plasma refilling rate (PRR) from interstitial tissue into blood vessels (automatic input): A plasma refilling rate (PRR) from interstitial tissue into blood vessels [l/hour] can be calculated by the following expression.

$$PRR = UFR + \Delta BV\% \cdot BW \cdot TBV/(100 \cdot \Delta t) \tag{2}$$

Here, UFR is an ultrafiltration flow rate [liter/hour], A BV % is a change rate of circulating blood volume [%], BW is a body weight [kg], and TBV is the total blood volume to a bodily weight [l/kg]. This information is used also for calculating the distribution of bodily water described later.

Next, items of information to be measured, set or inputted in a test information server device 5 or a device connected to it are as follows.

(1) General blood test (hematometry) information (automatic input): Number of class of white blood cells, number of red blood cells, hemoglobin, hematocrit and number of blood platelets.
(2) Liver function test information (automatic input)
(3) Kidney function test information (automatic input)
(4) Protein test information (automatic input)
(5) Electrolyte test information (automatic input)
(6) Blood sugar test information (automatic input)
(7) Myogenic enzyme test information (automatic input)
(8) Pancreas enzyme test information (automatic input)
(9) Cytokine test information (automatic input): IL-6, TNFα and the like
(10) Coagulation fibrinogenolysis test (automatic input): PT, APTT, HPT, IT, FDP, TAT, PIC, D dimer and the like
(11) Inflammatory reaction test information (automatic input): Erythrocyte sedimentation rate, CRP.
(12) Arterial blood gas analysis test information (automatic input)
(13) Immunity test information (automatic input)
(14) Endocrine function test information (automatic input)
(15) Virus marker test information (automatic input)
(16) Urinalysis information (automatic input): Number of white blood cells, number of red blood cells, protein concentration, sediment and the like
(17) Stool test information (automatic input): Occult blood reaction Next, items of information to be inputted in the client device 20 are as follows. These are bloodless parameters.

(1) Device information of blood treatment (manual input): Kind or lot number of a filter, serial number of a blood-treating device, flow rate information, anticoagulant information (kind, dosage, time of replacement), state of deterioration of a filter at an end, and the like.

(2) Information of a device not connected on-line (manual input): Bodily weight measured by a scale bed or a weight meter, bodily temperature measured by a thermometer, cytokine test information, activated clotting time (ACT) and the like.

(3) Information examined by a medical person (manual input): Consciousness level (necessary for evaluation of a score (APCHEII score) described later), psychic state (during an intensive care, a psychic state may be made temporarily abnormal by mechanical sounds of a monitor or restraint for insertion of a transfusion line or a blood treatment line (ICU syndrome), and it is conceivable that the quality of life (QOL) of a patient receiving a blood treatment comes into question. Therefore, it is conceivable that recording and saving a psychic state comes to be important in evaluating a blood treatment.), bleeding symptoms (spread of hemorrhagic stigma and the like) and the like.

(4) Therapeutic information (manual input): Transfusion information (kind and amount), drug dosing information (kind and amount), oxygen dosage of an oxygen mask, operation information, other special therapeutic information (protease inhibitor (mesyl(methylsulfonyl) acid naphamostat: used also as an anticoagulant for blood treatment) for a serious acute pancreatitis), constant infusion therapy of antibiotic and the like) and the like.

(5) Service information (manual input): Blood-collecting time, safety check information during treatment, trouble managing information and the like.

Next, displaying and recording function of the client device 20 is described in detail. This preferred embodiment makes it possible to select the time intervals at which information is displayed in a flow sheet. And it makes it possible to display biological information and blood treatment information at the same time, and possible to display not only input information but also diagnostic information, evaluation information, alarm information, advice information, feedback information and the like. Further, this preferred embodiment has an advantage that it is possible to select items to be displayed, select an item by clicking it with a mouse and set an additional item.

Next, the action and effect of displaying biological information in the displaying and recording function of the client device 20 are described in detail by the following classified items.

(1) Displaying or Recording the Time or Part which a Specimen has been Taken at or from The condition of a patient may change momentarily, and data of a specimen may be influenced by the time and part which the specimen is taken at and from (arterial blood, venous blood, a part from which the specimen is taken in the circuit, and the like). Particularly in a case of performing a blood treatment, since some index may be made seemingly low by being removed from blood through the blood treatment, it is important to display and record the state of taking a specimen (time, part and the like). And the removal of substances in blood by a blood treatment is performed by removal into waste fluid and absorption to a filter, but the removal efficiency of it is lowered with the passage of time. Due to this, in a case of performing a blood treatment, it is particularly important to display and record the condition (time, part and the like) of taking a specimen in addition to the condition of a patient and the condition of a blood treatment (time, condition and the like of performance) in evaluation of pharmacokinetics, evaluation of the removal efficiency of a filter and evaluation of clearance of a mediator in blood. In this preferred embodiment, the time of taking a specimen is displayed in a progress screen and according to need, its history is displayed as a trend on another basic progress screen or on a small area at a corner of the basic progress screen, and can be also print-recorded.

(2) Displaying or Recording Information Having an Influence on Pharmacokinetics

Various factors such as the dosing conditions (time, amount, process, solution method) of a drug, biological functions (liver function, kidney function and the like) taking part in elimination, factors participating in the manner of existence in blood (protein concentration, albumin concentration, the dosing condition of another drug and the like), the state of taking a specimen (time, part, kind of spit, separation method, saving state, blood collector and the like), the performing conditions of a blood treatment, the state of deterioration of a filter (clogging and the like) and the like take part in the pharmacokinetics of a drug dosed during performance of a blood treatment using a blood purification device 2 or 3. Therefore, these conditions need to be recorded or displayed at the same time in order to examine the pharmacokinetics during performance of a blood treatment.

(3) Displaying or Recording Information Having an Influence on Evaluation of the Efficiency of a Filter of the Blood Purification Device 2 or 3

Various factors such as biological functions (liver function and kidney function) taking part in elimination, factors (protein concentration, albumin concentration, the condition of dosing a drug, and the like) participating in the manner of existence of an objective index in blood, the state of taking a specimen (time, part, kind of spit, separation method, saving state, and a blood collector), the conditions for performing a blood treatment, the state of deterioration of a filter (clogging and the like) and the like take part in evaluation of the efficiency of a filter. Therefore, these conditions need to be recorded or displayed at the same time in order to evaluate the efficiency of a filter during performance of a blood treatment.

(4) Displaying or Recording Information Having an Influence on Evaluation of the Clearance of a Mediator in Blood Various factors such as biological functions (liver function, kidney function) taking part in elimination, factors (protein concentration, albumin concentration, the dosing condition of a drug, and the like) participating in the manner of existence of an objective mediator in blood, the state of taking a specimen (time, part, kind of spit, separation method, saving state, a blood collector and the like), the conditions for performing a blood treatment, the state of coagulation of a filter and the like take part in evaluation of the clearance of a mediator in blood. Therefore, these conditions need to be recorded or displayed at the same time in order to evaluate the clearance of a mediator in blood during performance of a blood treatment.

Next, the action and effect of displaying information of a blood treatment in the displaying and recording function of the client device 20 are described in detail by the following classified items.

(1) Elapsed time: The elapsed time since the beginning of a blood treatment can be displayed.

(2) The amount of blood treated, amount of substituted liquid used and amount of dialyzed liquid used: These information from the beginning of a blood treatment can be displayed.

(3) Estimated amount of anticoagulant used (the amount used per day, the amount used per month and the estimated amount used since admission into a hospital): It is difficult to grasp the amount of anticoagulant used when performing continuously a blood treatment. An anticoagulant is expensive and the dosage of it often comes into question in demand for payment by medical expense insurance. Therefore, it is useful to display or record an estimated amount used. And the client device 20 indicates clearly the scope of application of insurance, and displays an alarm in case that an estimated amount of anticoagulant used is about to exceed this scope. Further, it is possible to confirm details of the scope of application of insurance by utilizing an insurance medical treatment help function.

(4) Estimated amount of substituted liquid and dialyzed liquid used (estimated amount per day): It is difficult to grasp the amount of substituted liquid and dialyzed liquid used when performing continuously a blood treatment. It is useful in preparing insurance bills to display or record an estimated amount used. Hereupon, the client device 20 indicates clearly the scope of application of insurance, and displays an alarm in case that an estimated amount used is about to exceed this scope. And it is possible to confirm details of the scope of application of insurance by utilizing an insurance medical treatment help function.

(5) Time of replacement of anticoagulant: This can be displayed or recorded by setting and inputting it in advance.

(6) Time of replacement of substituted liquid and dialyzed liquid: This can be displayed and recorded by setting and inputting it in advance.

(7) Time of replacement of a waste liquid tank: This can be displayed or recorded by setting and inputting it in advance.

(8) Safety check items (checklist): This can be displayed or recorded by setting and inputting it in advance.

Next, a timer function according to this preferred embodiment is described in the following. In this preferred embodiment, at a specified time, information can be automatically displayed on a basic progress screen and on a small area at a corner of the basic progress screen, and an advice can be given by an alarm. Here, the time can be specified in advance and can be also changed halfway. For example, the display of time is set by the following time settings.

(1) Specimen taking button: Pattern 1 (1, 2, 4, 6, 12, 24, 36 and 48 hours after the beginning of a blood treatment), pattern 2 (1, 6, 12 and 24 hours after the beginning of a blood treatment), and pattern 3 (plural specified hours after the beginning of a blood treatment).

(2) Replacing operation button: Plural specified hours after.

(3) Specified time button: Regularly plural specified hours after.

Next, pickup displaying of information according to this preferred embodiment is described. This is a function of making it possible to automatically display specified data at specified time on a different screen (list- or graph-display), where time data can be specified in advance and can be changed halfway. For example, they are set as follows.

(1) Displaying information 1, 2, 4, 6, 12, 24, 36 and 48 hours after the beginning of a blood treatment.

(2) Displaying information for 30 minutes after the beginning of a blood treatment.

(3) Displaying information for 30 minutes before and for 30 minutes after a sudden rise in TMP value and the like.

Next, concrete examples of a display form according to this preferred embodiment are described in detail.

Figure 16:
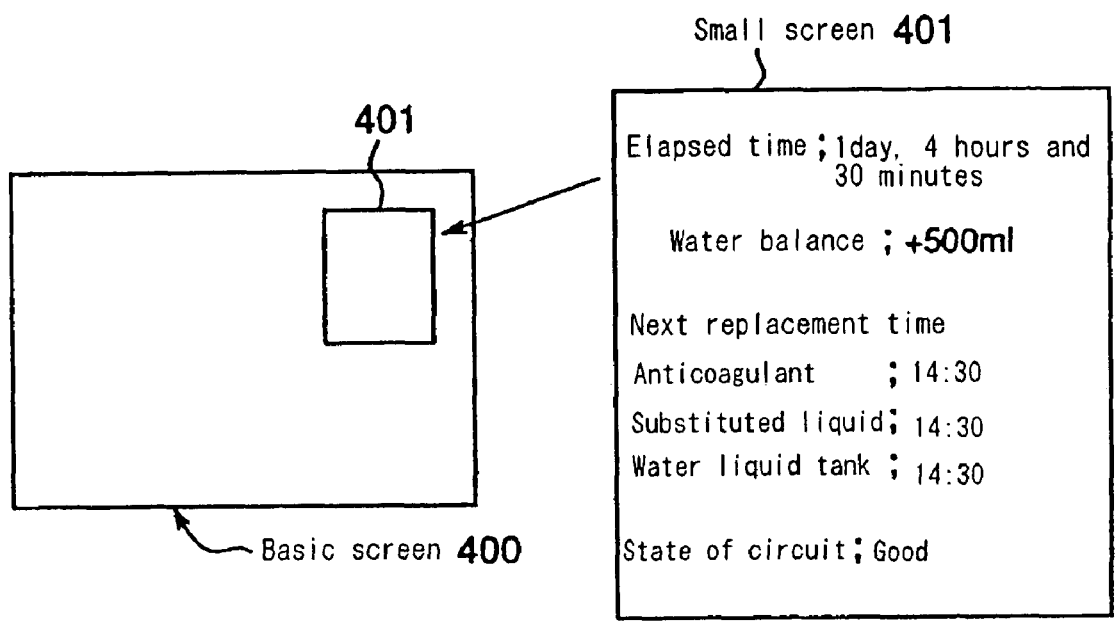
FIG. 16 is a figure showing a display example of a small screen being a variation example of the information management system process to be performed by the main controller 201 of the client device 20 of FIG. 1.

FIG. 16 is a variation example of an information management system process to be performed by the main controller 201 of the client device 20 of FIG. 1, and is a figure showing a display example of a small screen. As shown in FIG. 16, a small screen 401 including important information and useful information being always displayed can be displayed at a corner (its position can be moved) of a basic screen 400. Hereupon, the contents to be displayed, the position of the small screen and the size of it are basically set but can be freely changed and moved.

Figure 17:
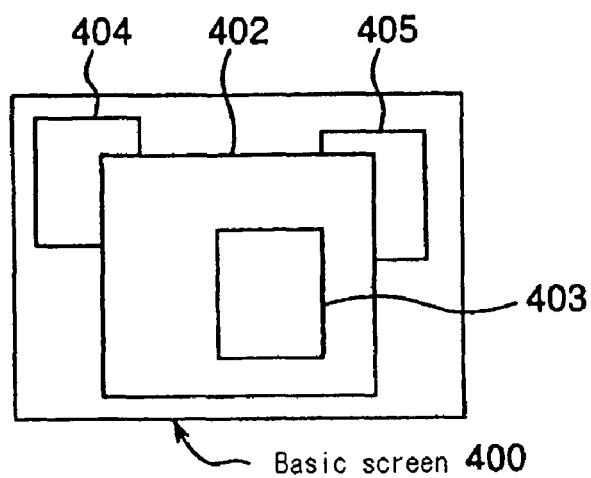
FIG. 17 is a figure showing a display example of multiple screens being a variation example of the information management system process to be performed by the main controller 201 of the client device 20 of FIG. 1.

FIG. 17 is a variation example of an information management system process to be performed by the main controller 201 of the client device 20 of FIG. 1, and is a figure showing a display example of many screens. As shown in FIG. 17, many screens 402 to 405 can be opened at the same time in a basic screen 400. They are basically set in content, position and size but can be freely changed and moved.

Figure 18:
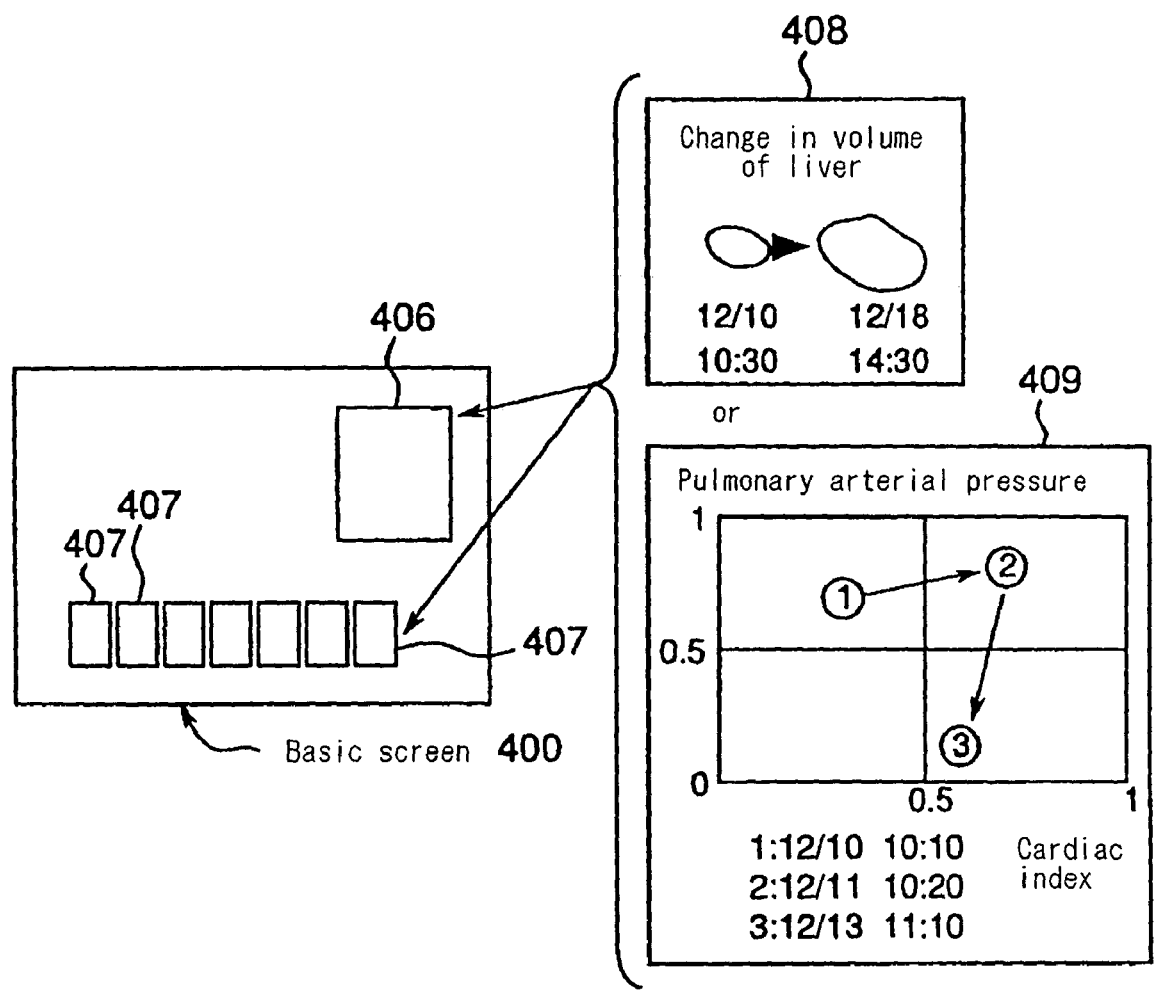
FIG. 18 is a figure showing a display example of illustrations being a variation example of the information management system process to be performed by the main controller 201 of the client device 20 of FIG. 1.

FIG. 18 is a variation example of an information management system process to be performed by the main controller 201 of the client device 20 of FIG. 1, and is a figure showing a display example of illustrations. As shown in FIG. 18, screens 408 and 409 displaying an illustration or a graph may be inserted into a small screen 406 in a basic screen 400 and may be displayed as many small screens 407. By this, a condition (medical observations, the condition of a disease and the like) or its change can be displayed using an illustration so that a person having no expertise can easily understand and does not misunderstand it.

Figure 19:
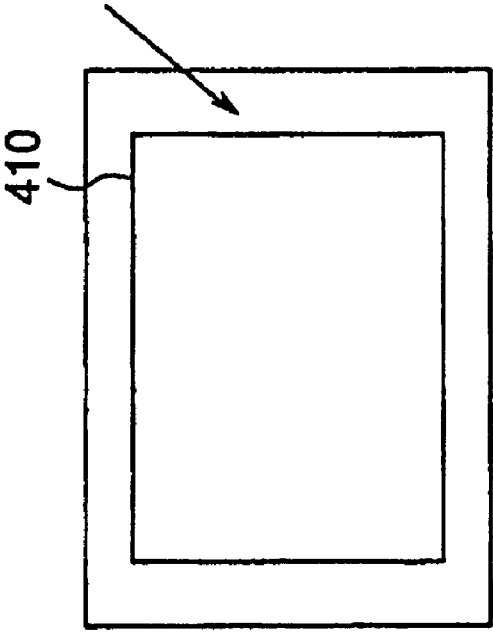
FIG. 19 is a figure showing a display example of a calendar being a variation example of the information management system process to be performed by the main controller 201 of the client device 20 of FIG. 1.

FIG. 19 is a variation example of an information management system process to be performed by the main controller 201 of the client device 20 of FIG. 1, and is a figure showing a display example of a calendar. As shown in FIG. 19, a small screen 410 displaying a blood treatment which has been already performed or a blood treatment which is scheduled to be performed together with the name of a person in charge or a responsible person in a calendar is displayed in a basic screen 400. Thereby, the progress of treatment (the state of performance of blood purification and the like) can be displayed in a monthly calendar. And a treatment plan (including a responsible person) can be displayed in a monthly calendar.

Figure 20:
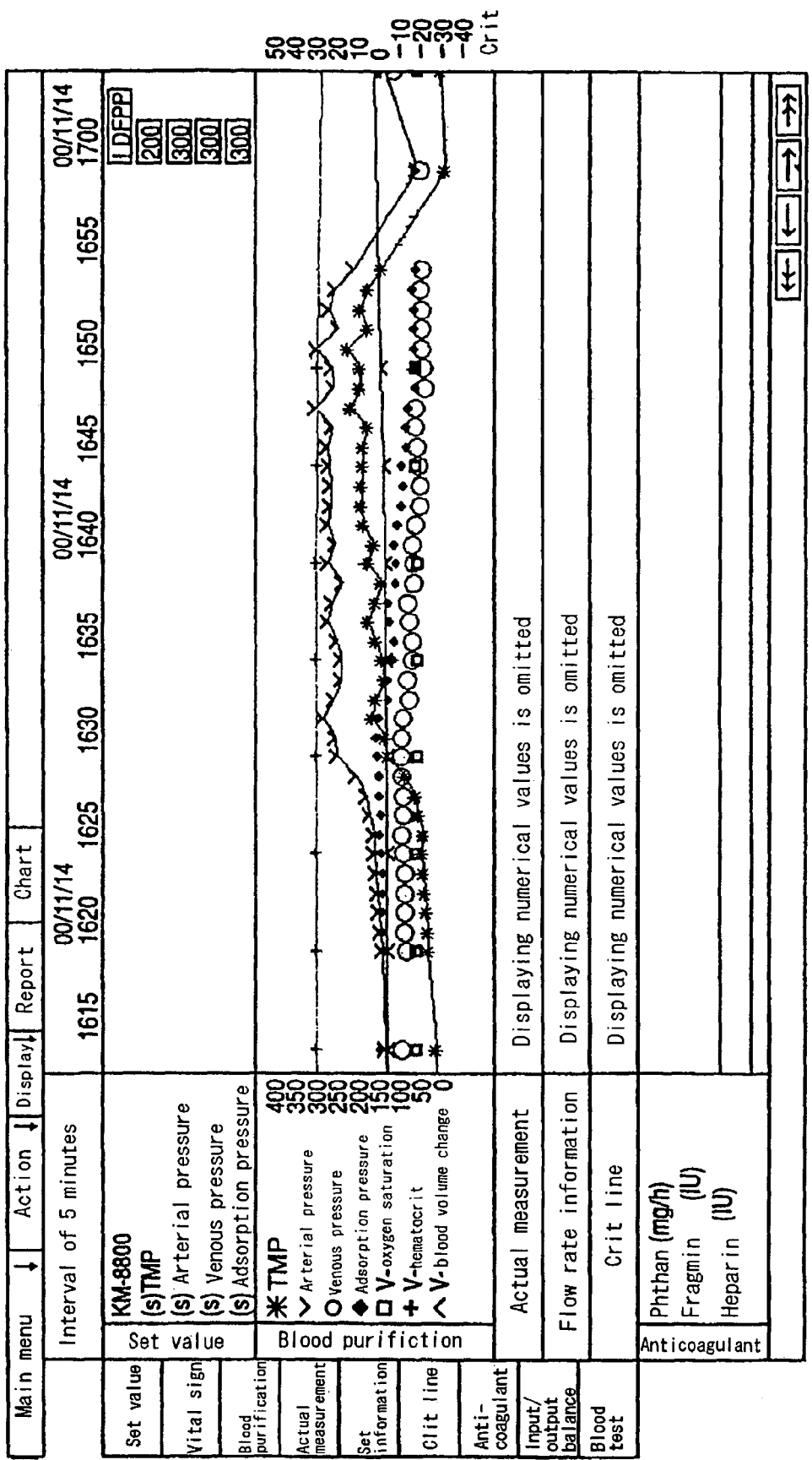
FIG. 20 is a figure showing a first embodiment of the display of a flow sheet to be displayed in a client device 20 according to this preferred embodiment.

Graph displays according to the following variation examples other than the graph displays of embodiments shown in FIG. 20 and after are also possible. Due to this, an item (plural items are also possible) and time to be display can be specified.

(1) Only the progress of TMP value for two days is magnified and displayed in a screen.
(2) The progress of a score (described in detail later) for one month is magnified and displayed in a screen.
(3) Pieces of data of several treatments are displayed one upon another.
(4) Data of another case are displayed upon data of the current case.
(5) A graph having a different numerical axis or a different time axis is made and displayed.
(6) A two-dimensional graph is made and displayed by specifying items of the X- and Y-axes.
(7) A three-dimensional graph is made and displayed by specifying items of the X-, Y- and Z-axes.

In this preferred embodiment, characters and a graph of numerical value data and the like can be displayed in a screen of a flow sheet, and an input screen for entering numerical data may be displayed separately at the same time on a basic screen of a flow sheet.

Next, a diagnostic method on the basis of an index, the change rate of an index and the correlation coefficient of an index using a management system of this preferred embodiment is described in detail. This diagnostic method stores diagnostic data based on information in advance, and displays and records them, if necessary. According to this preferred embodiment, by entering a large amount of information accurately, automatically and in real time and combining biological information with information of blood treatment, it is possible to display or record accurately, automatically, in real time and intelligibly an index regarding biological information, an index regarding information of blood treatment, an index obtained by combining biological information with information of blood treatment, the change rates of the indexes and a correlation coefficient, and evaluate the effects of the blood treatment and give advice on the basis of them. The following items are individually described.

(1) Matters Regarding Biological Information (1-1) Water Balance

On the basis of the amount of transfusion, amount of urine, bodily temperature, amount of removed water, dosage (volume) of drugs including an anticoagulant and the like, it is possible to calculate and display an accurate water balance in the whole body at each time. Since hemodialysis being generally and widely performed ends in a short time (4 to 6 hours) and is often performed on a patient of renal failure having a comparatively small amount of urine, it is enough to calculate a water balance from the amount of removed water. However, since an accute blood purification is performed on various cases such as a case of continuously performing a blood treatment for a long period, a serious case having a large insensible perspiration caused by a high fever and the like, it is difficult to accurately grasp a water balance in real time, and an erroneous adjustment of water balance has a great influence on the treatment and may bring a state of emergency such as a drop of blood pressure. At the time of performing a rapid blood purification it is necessary to comprehensively judge the water balance in consideration of the water balance of every index (amount of transfusion, amount of urine, bodily temperature, amount of removed water, dosage of drugs and the like) not only for a period of performing the blood treatment but also for a period of performing no blood treatment.

(1-2) Corrected Bodily Temperature

An ordinary blood-treating device is provided with a calorifier for dialyzed liquid or substituted liquid, and a bodily temperature drops during performance of a blood treatment. It is conceivable that this is caused by the influence of a dialyzed liquid or substituted liquid having a lower temperature than a bodily temperature or by a fact that blood circulates in the outside of a body being lower in temperature than the body, but the disappearance of fever occurs also by improvement in condition of a disease. Due to this, in order to accurately evaluate a bodily temperature during performance of a blood treatment, it is necessary to measure the temperature of blood at a blood outgoing part and at a blood incoming part and calculate a bodily temperature corrected (a bodily temperature on the assumption that no blood treatment is performed) in consideration of the condition of performance of the blood treatment. By displaying this corrected temperature, it is made possible to accurately grasp the condition of a patient. And by utilizing this function, it is possible to reevaluate the ability of a calorifier provided in a blood-treating device.

(1-3) Distribution of Bodily Water

It is clinically difficult to accurately grasp the distribution of water in a patient (to what degree bodily water is distributed in three regions, namely, inside cells, outside cells (inside blood vessels), outside cells (in interstitial tissue)). However, the reduction of water in blood vessels caused by a fact that the amount of removed water exceeds a plasma refilling rate (PRR) from interstitial tissue into blood vessels is mentioned as one of great causes for the drop of blood pressure during performance of a blood treatment. Therefore, it is important in performing a blood treatment to accurately evaluate the distribution of bodily water. At present the change ($\Delta BV$) in circulating blood volume and a plasma refilling rate (PRR) from interstitial tissue to blood vessels can be measured by continuously and bloodlessly measuring a hematocrit value (Ht value) and venous blood oxygen saturation in real time by means of a chamber attached to the circuit of a blood-treating device, and the adjustment of water removal using this index is performed. Since the amounts of intra- and extra-cellular water in an organism can be estimated separately by making a patient equipped with electrodes and measuring its bioelectric impedance, it is possible to grasp the amount of bodily water and its distribution and utilize them for grasping the condition of a patient and for setting the conditions at the time of performing a blood treatment by adding information of bioelectric impedance to conventional indexes.

(1-4) Score or Index Value

In order to comprehensively judge the condition of a patient, various scores (including criteria for judgement and indexes) derived by comprehensively judging individual indexes are in use. As examples of them, there are APACHEII score, Sepsis-related Organ Failure Assessment (SOFA) score, shock score, multiple organ failure score of Goris et al., multiple organ dysfunction score of Marshall et al., Cellular Injury Score (CIS), seriousness score and stage classification of serious acute pancreatitis (made by the Ministry of Health and Welfare's specific disease, intractable pancreas disease investigation and research team (Ogawa's team)), Revised Trauma Score (RTS), Injury Severity Score (ISS), shock index, renal failure index, estimated hospital case fatality rate, Trauma Score Injury Severity Score (TRISS) estimated survival rate, diagnostic criteria of SIRS, diagnostic criteria of multiple organ failure (MOF) (emergency medical treatment research society), and the like. In order to obtain these scores, it is necessary to accurately grasp various indexes and it is sometimes necessary to perform a complicated computation, and the judgment of scores requires often time and labor, and it is impossible to automatically calculate scores on the basis of information limited in the prior art. Therefore, by automatically calculating, displaying and recording scores by means of a biological information and device information management system according to this preferred embodiment, it is possible to estimate convalescence, improve the efficiency of work (automatization of score calculation), evaluate a therapeutic effect based on accurately grasping the condition of a disease, and share information using common scores.

(2) Matters Regarding Blood Treatment (2-1) Rising Rate of TMP

The state of deterioration (clogging and the like) of a filter is estimated by calculating and displaying the change rate of a pressure index of a blood purification device 2 or 3.

(3) Combination of Biological Information and Blood Treatment Information (3-1) Pharmacokinetic Parameter Dosed drugs are removed by blood purification during performance of a blood treatment. Therefore, it is necessary to consider the amount of a drug to be removed in determining the dosage of the drug. However, in case that the effective range and the poisoning range of a drug are close to each other, a medical person may rack its brains for adjusting the dose of the drug, and it is necessary to adjust the dose as measuring its concentration in blood. By measuring the concentration of a drug for a certain period and manually inputting the data, it is possible to automatically display pharmacokinetic parameters such as a half-life period of the concentration of the drug in blood, a blood clearance after passing through the circuit, clearance into a waste liquid, and the like, and to advise a concrete dose of the drug.

(3-2) Correlation Coefficient

The correlation coefficient between indexes or their index change rates of two pieces of biological information, the correlation coefficient between indexes or their index change rates of two blood treatments and the correlation coefficient between an index or its index change rate of biological information and an index or its index change rate of a blood treatment are calculated.

The result of performing diagnosis at intervals of eight hours (at 0, 8 and 16 o'clock) for example is displayed in a flow sheet and is used for transferring the information in shift of operation. And the result of performing diagnosis at intervals of 24 hours (at 0 o'clock to 0 o'clock) is displayed in a flow sheet, and this is necessary from the viewpoint of a demand for payment of insurance money. Further, the result of performing diagnosis at intervals of 24 hours (at 8 o'clock to 8 o'clock) is displayed in a flow sheet, and this is necessary from the viewpoint of clinic work.

Next, a method of evaluation using a management system of this preferred embodiment is described in detail by the following items. This method of evaluation stores evaluation data based on information in advance and displays or records them, if necessary.

(1) Work Analysis

This is a work efficiency (man power) analysis, and by recording and analyzing the contents of work (preparation, safety check, operation of replacement, management of alarm, recovery and the like) at the time of preparing, beginning, performing and recovering work, a person in charge, a needed time and the like, the work analysis makes it possible to evaluate the man power related to the blood treatment with the passage of time (evaluate when what work requires how much man power) and also take a measure of improvement in work efficiency on the basis of the information and judge the effect of it.

(2) Safety Analysis (2-1) Alarm Analysis

Recording and analyzing the time, kind and recovery state of an alarm of a blood purification device 2 or 3 or a circulating blood volume measuring device 4 make it possible to evaluate a blood-treating device and adjust the organization of operation (adjust the number of persons in charge according to a time zone and the like), and bring the prevention of an accident and also judge the effect of a safety measure.

(2-2) Trouble Analysis

Examining trouble matters leads to the prevention of accidents.

(2-3) Evaluation of a Blood Purification Device 2 or 3 or a Circulating Blood Volume Measuring Device 4

By inputting the serial number of a blood purification device 2 or 3 or a circulating blood volume measuring device 4, and recording and saving alarm analysis information and trouble analysis information regarding every patient who has used the device, it is possible to utilize the information for grasping the state of using the device and for evaluating and improving the device.

(3) Effect Analysis

This is for example the change of a score, and a clinical effect of blood purification is analyzed not as a simple input index but as a change in score.

(4) Economic Efficiency (4-1) It is possible to make a list of items and drugs (anticoagulant, substituted liquid, dialyzed liquid and the like) used with regard to blood treatment and a collection of insurance points per month and per patient.

(4-2) It is possible to assess labor cost per month and per patient.

Next, a method for giving advice to a medical worker using a management system according to this preferred embodiment is described by the following items. This advising method stores advice data based on information in advance, and displays and records the information according to need.

(1) Policy Regarding Blood Treatment (1-1) Performing Conditions at the Beginning and During Performance Priming conditions, performing conditions at the beginning and the like are displayed so as to give advice on the basis of biological information before beginning a blood treatment and information during the previous performance of blood treatment.

(1-2) Time of Replacement or Time of End of a Filter of a Blood Purification Device 2 or 3

The time of end (time of replacement of a filter) is advised on the basis of various indexes and index change rates.

(1-3) Adaptation

The adaptation of blood treatment (the start, end of a process and end of all processes) is advised according to various indexes, index change rates, scores and change in score.

(1-4) Method of Medical Treatment

This advises the optimum method for performing a blood treatment (flow rate setting, dosage of anticoagulant and the like).

(2) Operation of Blood Treatment (2-1) Operation of Replacement

Replacement of anticoagulant, substituted liquid, dialyzed liquid, waste liquid tank and the like is advised.

(2-2) Specimen Taking Operation Button (2-2-1) This displays the time of taking a specimen. Concretely, for example, this displays automatically a specified specimen taking time of 1, 2, 4, 6, 12, 24, 48 hours or the like after the beginning of blood treatment in a basic progress screen and in a small screen at a corner of the basic progress screen according to need. The time of taking a specimen can be specified in advance and can be also changed halfway.

(2-2-2) An alarm may sometimes sound due to a pressure change at the time of taking blood in the circuit. By linking to an alarm function, it is possible to record the alarm as an alarm caused by a blood-collecting operation and prevent misunderstanding in performing a safety evaluation.

(2-2-3) Advice for a collecting method is displayed. A spit to be used for taking a specimen of each item, the amount of specimen to be taken, a method of treatment, a necessary total amount of taken specimen and the like are displayed by specifying a test item.

(2-2-4) Help data are displayed by providing a help function for a specimen taking operation.

(2-3) Safety Check Operation

The data for safety check operation are displayed.

(3) Advice Regarding Economic Efficiency

Advice for the following items for example is displayed or recorded and an alarm (an alarm sound and the like) is outputted using a specific threshold value.

(3-1) Amount of Anticoagulant Used (3-2) Amount of Substituted Liquid or Dialyzed Liquid Used (3-3) Amount of Blood Plasma Drug Used (4) Measure Against Trouble (4-1) Alarm and Trouble Help Function When an alarm sounds or a trouble occurs, its cause and a method for coping with it are automatically displayed intelligibly (using an illustration also) in a small screen at a corner of a basic progress screen. And a question about a cause for it or a measure against it is inputted and an answer to the question can be given.

(4-2) Function of Predicting Occurrence of a Trouble

This predicts in advance an abnormal state being liable to occur in future from various information, arouses attention and displays a method for coping with it.

Thanks to the above advices, it is possible to feed back information to a medical worker. And since plural medical workers can share information, there is an effect of making a proper medical treatment possible.

And the time of recording a report can be set with regard to recording on a recording paper using a printer 30 and, for example, can be set as follows.

(1) Every 8 hours (0, 8 and 16 o'clock): The report is used for transferring the information in shift of operation.

(2) Every 24 hours (from 0 o'clock to 0 o'clock): The report is necessary from the viewpoint of a demand for payment of insurance money.

(3) Every 24 hours (from 8 o'clock to 8 o'clock): The report is necessary from the viewpoint of clinic work.

And the contents of a report are similar to the manner of a flow sheet to be displayed, and items can be set, changed and added.

Further, the patient information server device 10 can record and store every information at the same time, and a summary report can be printed and outputted on a recording paper at intervals of 8 hours or 24 hours (from 0 o'clock or from 8 o'clock) from the patient information server device 10.

Furthermore, environment for a management system according to this preferred embodiment is described. For example, a place where a blood-treating device of a blood purification device 2 or 3 is installed may not be a dialysis room but may be a room having a terminal of a client device 20, which room makes it possible to install a blood purification device 2 or 3 at a bedside and connect it to the relevant management system without moving the bed in a ward. For example, it makes it possible to perform various blood treatments on various patients (in disease or seriousness) such as a patient requiring an intensive care in an ICU, a patient needing a middle-class high care in an HCU (high care unit), a patient receiving a blood treatment in one day, and the like. And since a patient is not moved to a room having a blood dialyzing installation, the patient can receive a blood treatment as continuing a treatment which the patient has been currently receiving as it has been. Further, if there is a piping for hemodialysis at a patient's bedside, the patient can receive hemodialysis also.

And according to this preferred embodiment, it is possible to cope with various blood treatments. Concretely, by changing the kind of a blood treatment device, a filter, a blood circuit and the like to be used, it is possible to cope with various blood treatments. And it is possible to cope with various blood treatments covering a range from an intermittent blood treatment completed in several hours to a continuous blood treatment continuing for several days:

EMBODIMENTS

With reference to an example of a flow sheet for blood purification actually obtained by a management system according to this preferred embodiment, a medical explanation is performed and the action and effect specific to this management system are described in the following.

FIG. 20 is a figure showing a first embodiment of displaying a flow sheet to be displayed in a client device 20 according to this preferred embodiment. In a flow sheet of FIG. 20, items to be displayed can be selected and freely combined with each other. Further, since an index regarding blood treatment is not only represented as a numerical value actually measured but also displayed as a trend graph, the state of variation is easy to understand. Further, the time of displaying can be selected, and the time of registration can be also displayed and recorded. A blood purification device used, the kind of blood treatment (DFPP) and the alarm set value of a blood purification device can be displayed and recorded. Further, information of a circulating blood volume-measuring device (CRIT LINE® monitor) can be also displayed at the same time. The size of a character can be adjusted. In FIG. 20, numerical values of the following items are displayed at intervals of 5 minutes under the date and hour, set values and a trend graph (in the form of a chart) of blood purification.
(1) Actual measurements (TMP, arterial pressure, venous pressure and adsorption pressure)
(2) Flow rate information (instantaneous flow rate of blood, instantaneous flow rate of blood plasma, instantaneous flow rate of waste liquid, accumulated flow rate of blood, accumulated flow rate of blood plasma, accumulated flow rate of waste liquid, target value of blood plasma to be treated)
(3) Measurements of a CRIT LINE® monitor (hematocrit value of venous blood, change in blood volume of venous blood, oxygen saturation of venous blood)
(4) Dosage of anticoagulant (phthan (mg/h), fragmin (IU), heparin (IU), maintenance transfusion: displayed only at dosing)

In embodiments shown in FIGS. 20 to 27, the display of numerical values of actual measurements is omitted for simplifying and clearing the contents of display.

Figure 21:
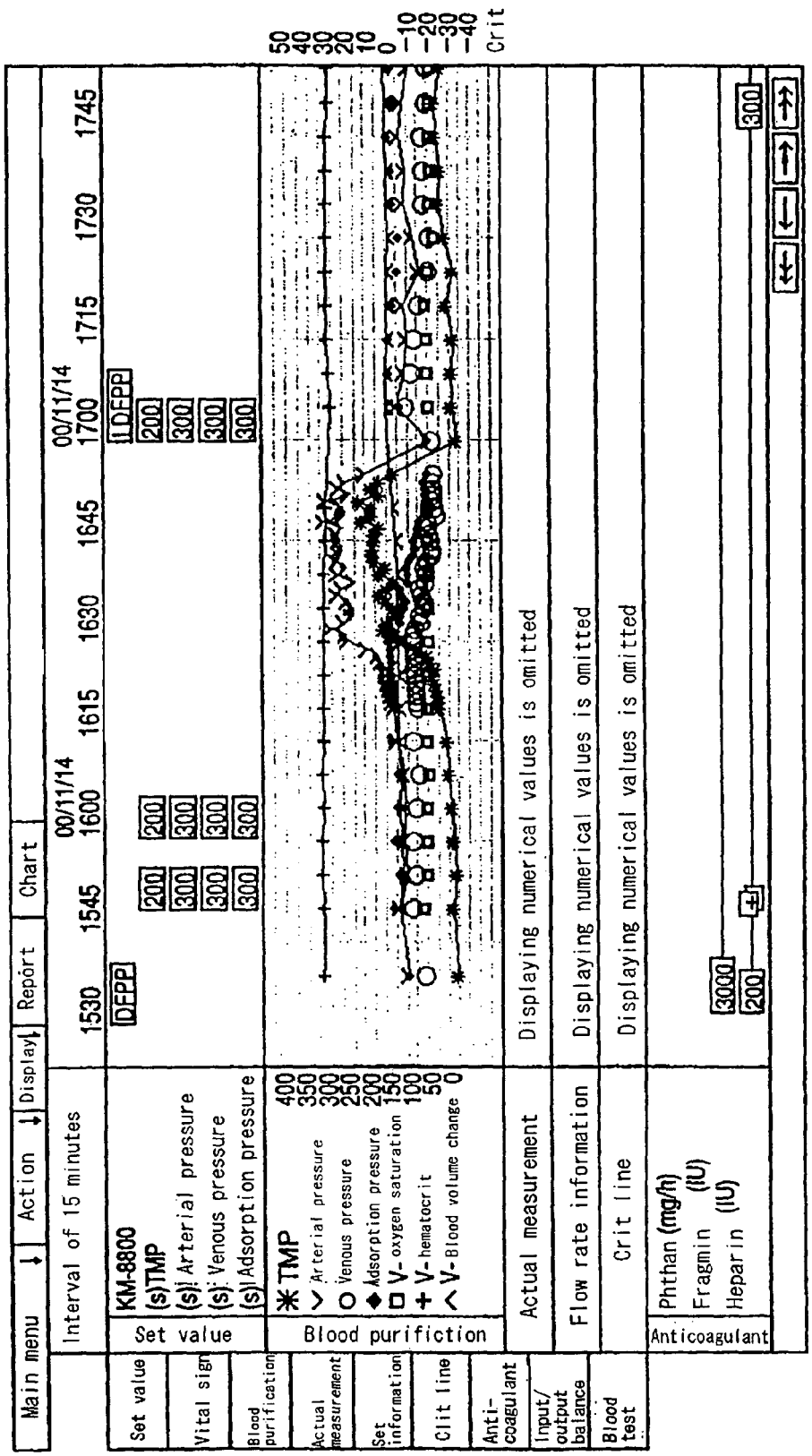
FIG. 21 is a figure showing a second embodiment of the display of a flow sheet to be displayed in the client device 20 according to this preferred embodiment.

FIG. 21 is a figure showing a second embodiment of displaying a flow sheet to be displayed in a client device 20 according to this preferred embodiment. In comparison with a flow sheet of FIG. 20, FIG. 21 makes it possible to display information for 3 hours in one screen by changing the time interval from 5 minutes to 15 minutes (FIG. 21 shows only a main part), and makes it easier to grasp the progress in comparison with the display at intervals of 5 minutes capable of displaying information of 1 hour on one screen. Further, even if the time interval of 15 minutes is used for displaying, a trend graph of indexes regarding blood treatment has information at intervals of 5 minutes automatically displayed in it. Further, the trend graph of indexes regarding blood treatment can additionally display information of intervals of 1 minute later, and can intelligibly display and record more detailed changes. Further, by displaying indexes regarding blood treatment in the form of a trend graph, it is possible to intelligibly display and record the state of change in them and the rate of change in them (the inclination of the graph). In FIG. 21 also, in the same way as FIG. 20, the numerical values of items such as actual measurements, flow rate information, measurements of a CRIT LINE® monitor and dosage of anticoagulant are displayed under the date and hour, set values and a trend graph of blood purification (in the form of a chart).

Figure 22:
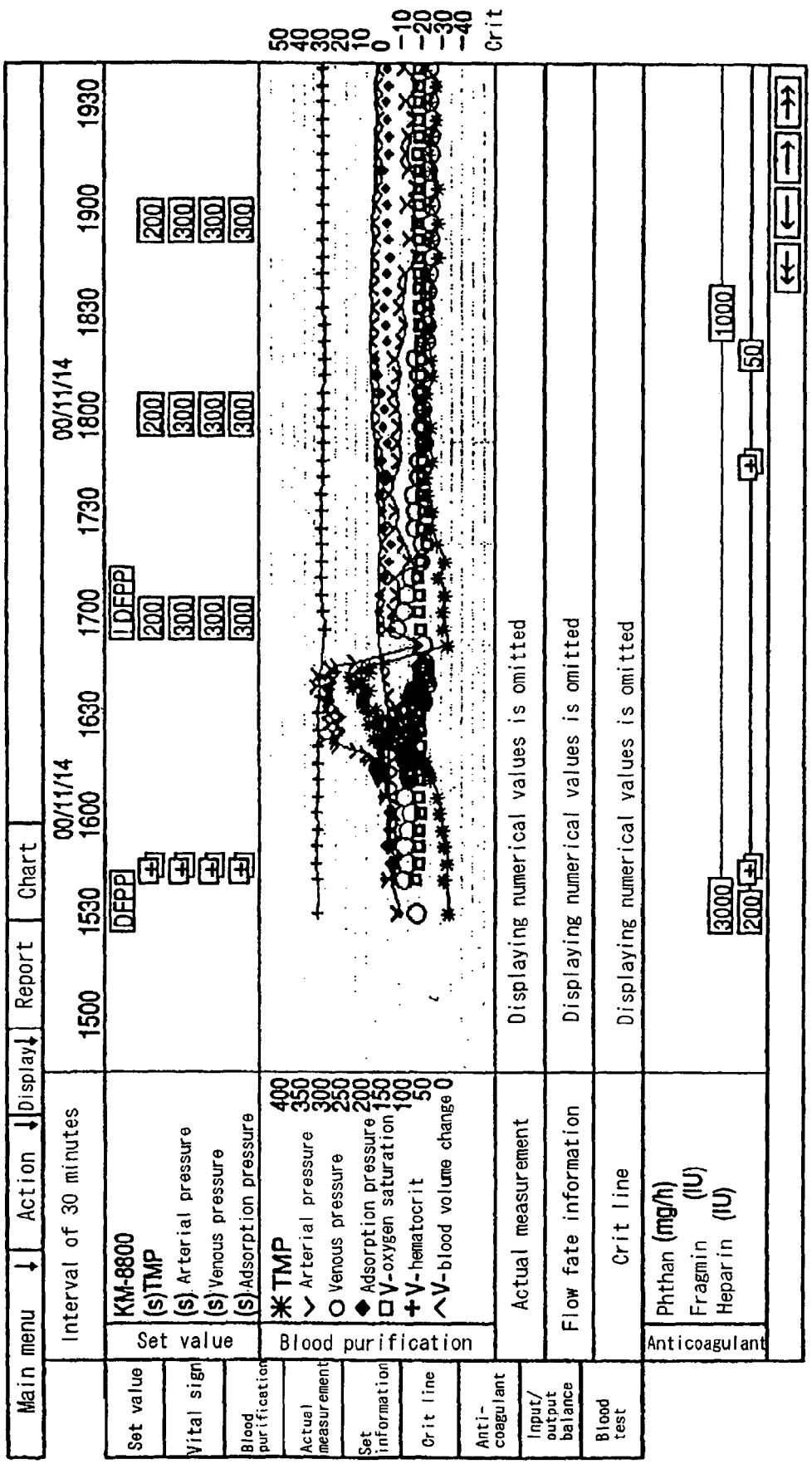
FIG. 22 is a figure showing a third embodiment of the display of a flow sheet to be displayed in the client device 20 according to this preferred embodiment.

FIG. 22 is a figure showing a third embodiment of displaying a flow sheet to be displayed in a client device 20 according to this preferred embodiment. In comparison with a flow sheet of FIG. 21, FIG. 22 makes it possible to display information for 6 hours in one screen by changing the time interval from 15 minutes to 30 minutes (FIG. 22 shows only a main part), and makes it possible to display all progress of DFPP which has ended in 4 hours and 30 minutes. Further, it makes it possible to intelligibly display the state of dosing an anticoagulant during performance of DFPP simultaneously with indexes regarding blood treatment and grasp the information in a moment. It can display and record also the state of performing transfusion at the same time. In FIG. 22 also, in the same way as FIGS. 20 and 21, the numerical values of items such as actual measurements, flow information, measurements of a CRIT LINE® monitor and dosage of anticoagulant are displayed under the date and hour, set values and a trend graph of blood purification (in the form of a chart).

Figure 23:
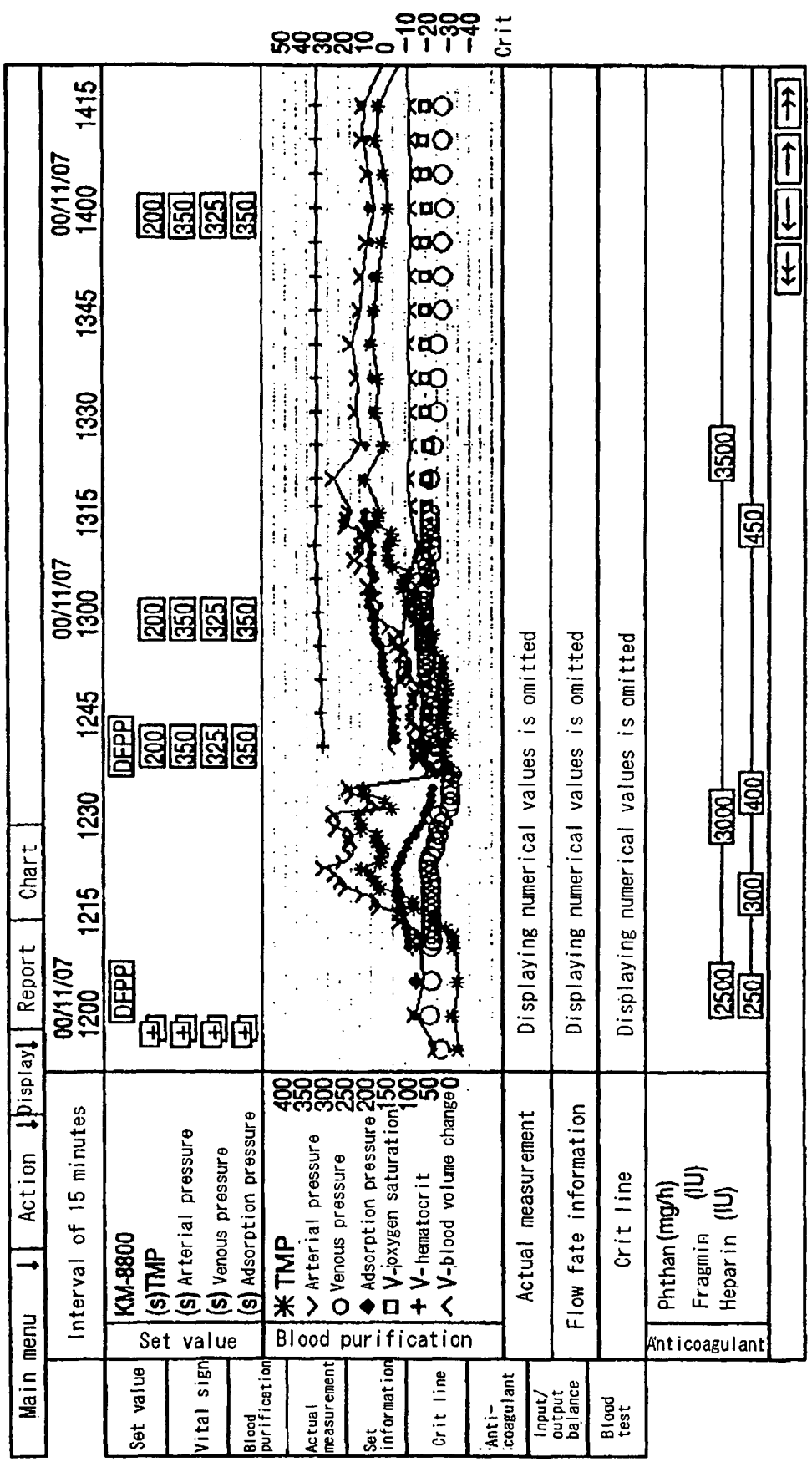
FIG. 23 is a figure showing a fourth embodiment of the display of a flow sheet to be displayed in the client device 20 according to this preferred embodiment.

FIG. 23 is a figure showing a fourth embodiment of displaying a flow sheet to be displayed in a client device 20 according to this preferred embodiment. A flaw sheet of FIG. 23 makes it easy to understand the state of change or the rate of change (inclination of a graph) in indexes regarding blood treatment (particularly the rate of change in TMP) by displaying them with a trend graph, and since the possibility that a filter begins clogging has been considered, it has been possible to adjust the amount of anticoagulant (heparin) or amount of maintenance transfusion on the basis of this information. Further, it has been possible to judge the effect due to adjustment of the amount of anticoagulant or maintenance transfusion from the state of change or the rate of change (inclination of a graph) in indexes regarding blood treatment (particularly the rate of change in TMP). Further since the trend graph of indexes regarding blood treatment can display also information at intervals of 1 minute additionally later, it can display, examine and record in more detail a period in which an index or its change rate regarding blood treatment or biological information has suddenly changed. In FIG. 23 also, in the same way as FIGS. 20 to 22, the numerical values of items such as actual measurements, flow rate information, measurements of a CRIT LINE® monitor and dosage of anticoagulant are displayed under the date and hour, set values and a trend graph of blood purification (in the form of a chart).

Figure 24:
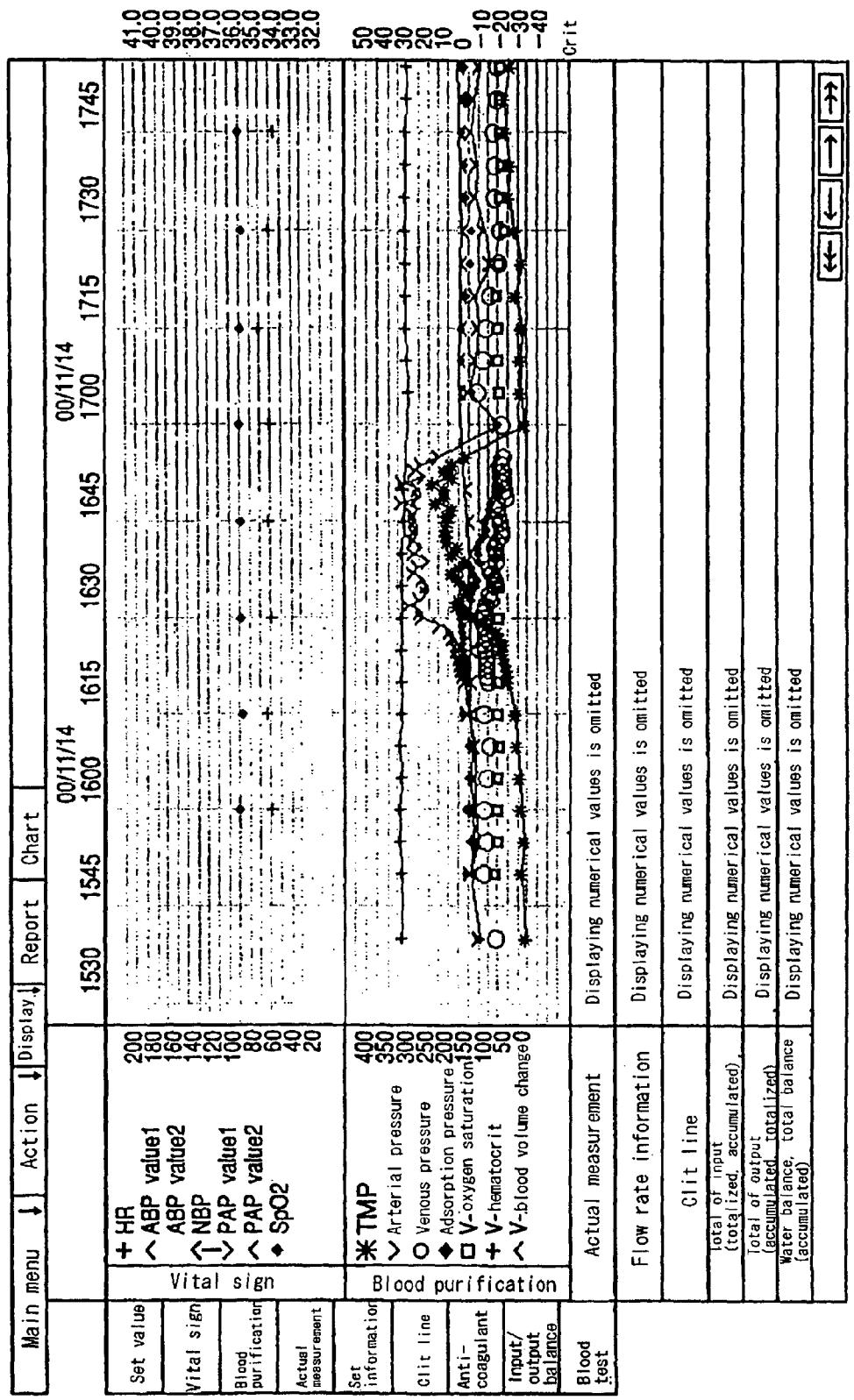
FIG. 24 is a figure showing a fifth embodiment of the display of a flow sheet to be displayed in the client device 20 according to this preferred embodiment.

FIG. 24 is a figure showing a fifth embodiment of displaying a flow sheet to be displayed in a client device 20 according to this preferred embodiment. A flow sheet of FIG. 24 makes it possible to display also vital signs (biological information) measured by a bedside monitor 1 at the same time. Hereupon, as vital signs, there are shown a heart rate (HR), systolic arterial blood pressure (ABP value 1), diastolic arterial blood pressure (ABP value 2), central venous pressure (CVP), systolic pulmonary arterial pressure (PAP value 1), diastolic pulmonary arterial pressure (PAP value 2), arterial blood oxygen saturation ($aSpO_2$). The time of inputting a vital sign can be set separately from the time of inputting information about blood treatment. The collection of excessive biological information (measurement of blood pressure by cuff) may bring pain, and if vital signs are stable, it is possible to collect vital signs at intervals of 15 minutes. Further, water balance can be also displayed at intervals of 1 hour. In FIG. 24, there are displayed the date and hour, a trend graph of vital signs (in the form of a chart), a trend graph of blood purification (in the form of a chart), actual measurements, measurements of a CRIT LINE® monitor, actual measurements of the total amount of input water (total and accumulated), total amount of output water (total and accumulated), actual measurements of water balance (accumulated) and actual measurements (accumulated) of total balance in numerical values.

Figure 25:
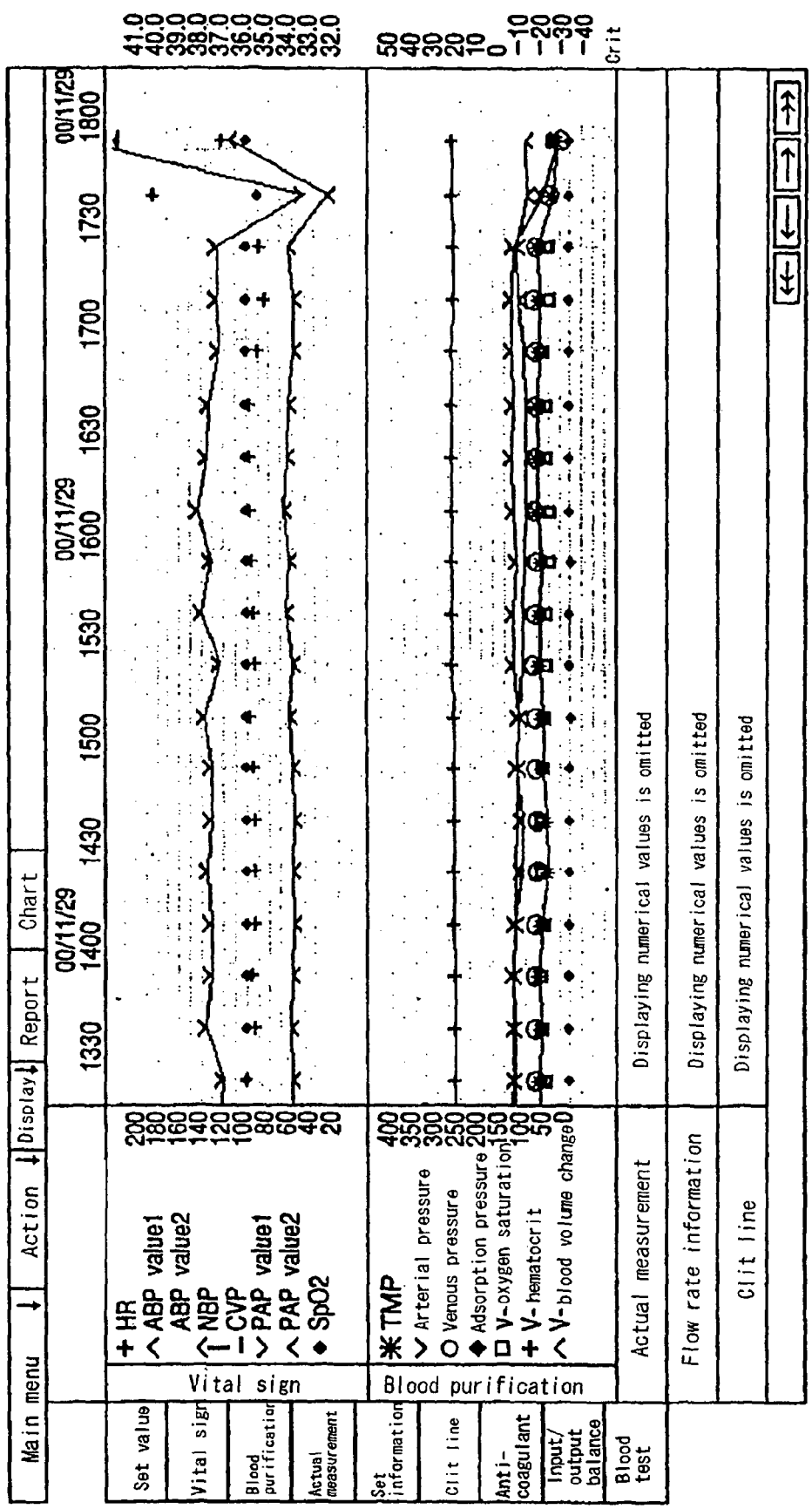
FIG. 25 is a figure showing a sixth embodiment of the display of a flow sheet to be displayed in the client device 20 according to this preferred embodiment.

FIG. 25 is a figure showing a sixth embodiment of displaying a flow sheet to be displayed in a client device 20 according to this preferred embodiment. A flow sheet of FIG. 25 is a record of a patient who changed in general condition during blood treatment, did not react to an emergency medical treatment and could not be saved. In such a way, the condition of a patient may sometimes change suddenly or a trouble may occur during performance of a blood treatment, but in such a case, it is impossible to accurately record the state of blood treatment due to being busy in fast treatment. In a management system according to this preferred embodiment, the present management system capable of automatically displaying and recording biological information and blood treatment information can leave an accurate record even in case that the condition of a patient changes suddenly or a trouble occurs. The possibility that the condition of a patient is changed by the influence of blood treatment is also conceivable. As shown in this FIG. 25, it can be confirmed tat indexes of blood purification were kept stable and the blood treatment was normally performed until the condition of the patient changed suddenly. Further, since after the general condition suddenly changed, the venous blood oxygen saturation of a circulating blood volume measuring device dropped but the hematocrit value did not change, it is thought that a hemorrhage is not the cause of the sudden change. In such a way, this can be utilized also for explication of the condition of a disease. Further, the arterial blood oxygen saturation ($SpO_2$) measured by a pulse oximeter which has not been used in the prior art can be displayed as one of vital signs at the same time. Additionally, central venous pressure (CVP), pulmonary arterial pressures (PAP value 1, PAP value 2), cardiac output (CCO) and axillary temperature can be also displayed. FIG. 25 displays the date and hour, a trend graph of vital signs (in the form of a chart), a trend graph of blood purification (in the form of a chart), actual measurements, actual measurements of flow rate information, and measurements of a CRIT LINE® monitor in numerical values.

Figure 26:
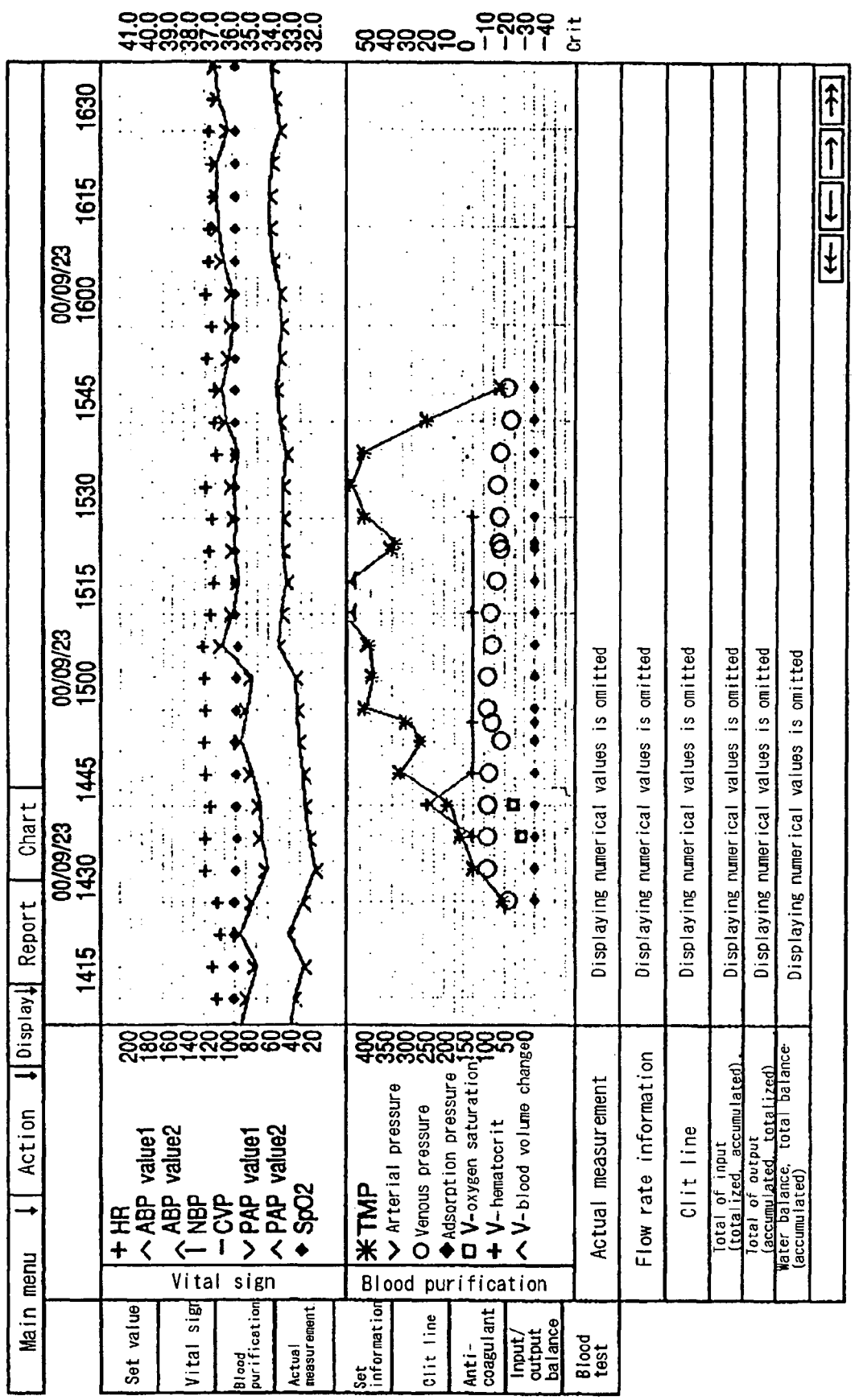
FIG. 26 is a figure showing a seventh embodiment of the display of a flow sheet to be displayed in the client device 20 according to this preferred embodiment.

FIG. 26 is a figure showing a seventh embodiment of displaying a flow sheet to be displayed in a client device 20 according to this preferred embodiment. A flow sheet of FIG. 26 can display the whole progress (for about 90 minutes) of an endotoxin adsorption therapy in one screen. A fact that the blood pressure of a patient who was in a shocked state was gradually raised by performing an endotoxin therapy and its systolic arterial pressure (ABP value) and diastolic arterial pressure (ABP value 2) both rise by about 20 mmHg after the end of the therapy can be easily judged by displaying a trend graph of vital signs about 45 minutes before and 45 minutes after performing the therapy and a trend graph of blood treatment at the same time. And by displaying also transfusion information at the same time, it can be confirmed that the blood pressure rise is not caused by the increase of transfusion. In such a way, since the change in biological information appearing during the progress is influenced by various treatments including transfusion, it is important to display and record other therapies at the same time in judging the effect of a blood treatment. In FIG. 26, there are displayed the date and hour, a trend graph of vital signs (in the form of a chart), a trend graph of blood purification (in the form of a chart), actual measurements, actual measurements of flow rate information, other information (calorifier temperature, elapsed time), actual measurements of the total amount of input water (total and accumulated), total amount of output water (total and accumulated), actual measurements of water balance (accumulated) and actual measurements (accumulated) of total balance in numerical values.

Figure 27:
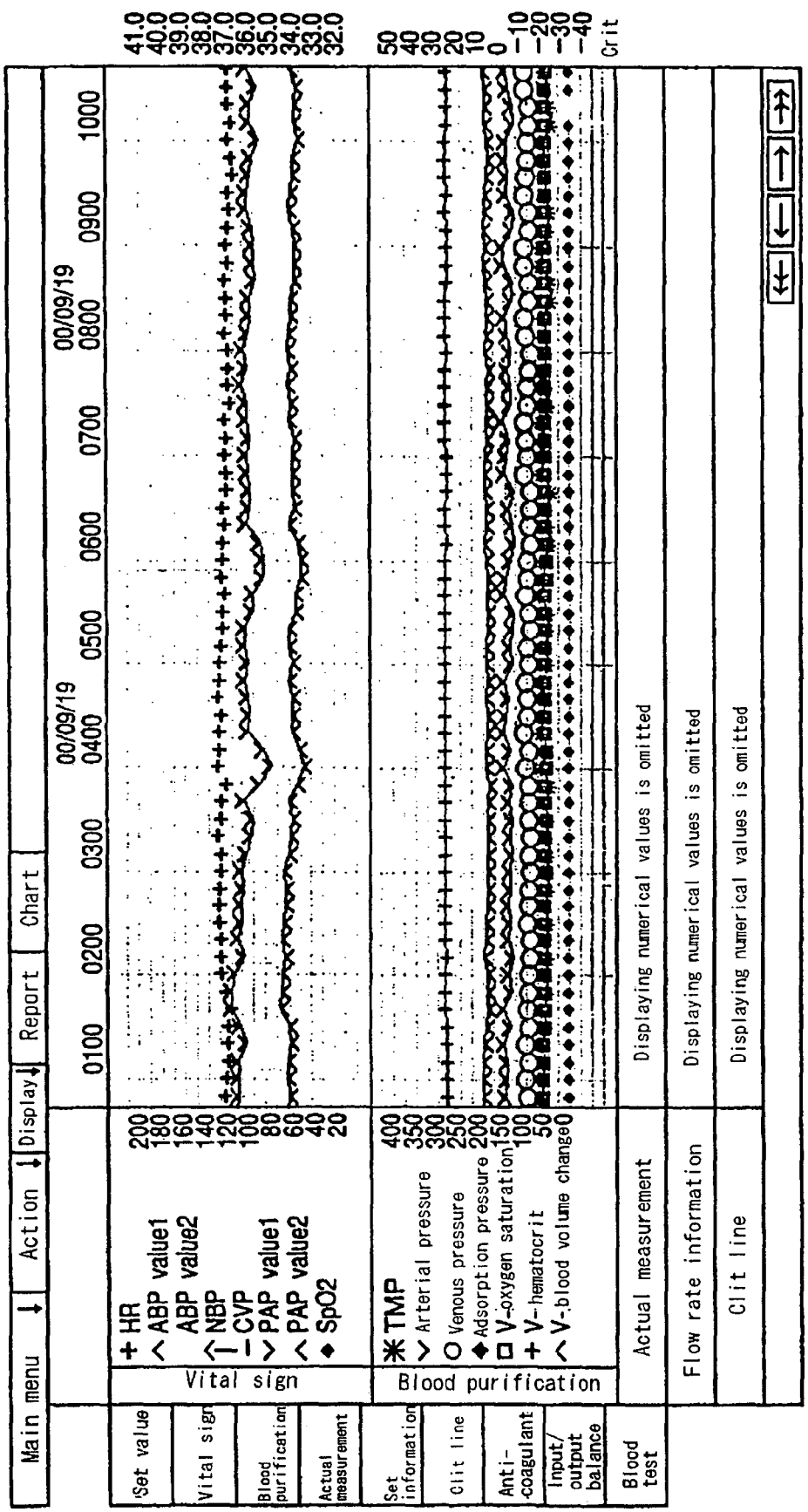
FIG. 27 is a figure showing an eighth embodiment of the display of a flow sheet to be displayed in the client device 20 according to this preferred embodiment.

FIG. 27 is a figure showing an eighth embodiment of displaying a flow sheet to be displayed in a client device 20 according to this preferred embodiment. A flow sheet of FIG. 27 makes it possible to display information of 12 hours in one screen by using a time interval of 1 hour, and makes it easy to grasp the progress when performing continuously a blood treatment. Displaying vital signs and indexes of blood treatment at the same time in a trend graph makes it easy to understand the change in the indexes and the relation among them. The progress is made easier to grasp not only by displaying indexes of blood treatment in a trend graph but also by displaying actual measurements of them at intervals of 1 hour at the same time. FIG. 27 displays the date and hour, a trend graph of vital signs (in the form of a chart), a trend graph of blood purification (in the form of a chart), actual measurements, actual measurements of flow rate information, and measurements of a CRIT LINE® monitor in numerical values.

Next, a ninth embodiment estimating the clogging ratio of a filter of a blood purification device 2 or 3 and controlling the set value of flow rate and the dosage of anticoagulant in the blood purification device 2 or 3 is described in the following.

Replacement of a filter due to clogging of the filter attached to a blood purification device 2 or 3 leads to the loss of blood and comes into question from the viewpoint of safety or economy. However, an excessive dosage of an anticoagulant to be provided into the circuit for preventing clogging of the filter not only has the possibility of causing a serious hemorrhagic complication (cerebral hemorrhage or the like) but also comes into question from the viewpoint of economy since the anticoagulant is expensive. Due to this, it is important to prevent the development of clogging by finding clogging of a filter in an early stage and properly adjusting the dosage of the anticoagulant, but there has not been a method for monitoring the clogging of a filter continuously in real time.

According to a publicly known labyrinth pore theory, in case that a fluid flows through pores of the membrane wall of a filter in laminar flow, the expression of Hagen-Poiseuille's law (expression (3)) is effective as follows.

$$Q = \pi \cdot r_p^4 \cdot \Delta P / 8\eta / 1 \tag{3}$$

$$Q = A^2 \Delta P / 8\pi \eta / 1 \tag{4}$$

$$A = A_k \cdot A_m (1 - K/100) \tag{5}$$

$$1 = \tau \cdot \Delta X \tag{6}$$

$$Q = 6 \times 10^{-5} Q_f \tag{7}$$

$$\Delta P = \Delta P' / 133.3 \tag{8}$$

Here, the symbols of the respective parameters represent the following matters.
Q: Flow rate passing through pores [m³/sec]
$Q_f$: Filtration rate [ml/min]
$r_p$: Radius of a pore [m]
ΔP: Pressure difference between both ends of a pore (corresponding to TMP in this case) [Pa]
ΔP': Pressure difference between both ends of a pore (corresponding to TMP in this case) [mmHg]

η: Viscosity of fluid passing through a pore [Pa·sec]
A: Total sectional area of pores [m$^2$]
$A_k$: Ratio of the sectional area of pores to the unit area of the membrane
$A_m$: Area of the membrane [m$^2$]
K: Clogging ratio [%]
l: Length of a pore [m]
τ: Winding path ratio
ΔX: Membrane thickness [m]

These parameters are the parameters of a filter.

And from the above expressions (4) to (8), the clogging ratio K of a filter can be calculated by the following expression. Here, the clogging ratio K of a filter means the ratio of the total sectional area of pores capable of transmitting fluid to the total sectional area of pores of the filter.

$$K=[1-(3.67\pi \times 10^{-6} \cdot \tau \cdot \eta \cdot Q_f / \Delta P')^{0.5}/(A_k \cdot A_m)] \times 100 \quad (9)$$

Further, the change rate per unit time ΔK[%/min] of a clogging ratio K can be calculated by the following expression.

$$\Delta K = dK/dt \quad (10)$$

Here, t is time [min].

In this ninth embodiment, parameters $A_k$, $A_m$, τ and ΔX are prescribed by the kind of a filter, and parameters Ak, $A_m$, τ, ΔX, $Q_f$ and ΔP (=TMP) are included in biological information and device information collected from a blood purification device 2 or 3 and a circulating blood volume measuring device 4 by a biological information and device information management system according to this preferred embodiment, and these parameters are collected in the following.

(1) Ak, Am, τ, ΔX, (manually inputted):
(2) $Q_f$ (measured by a blood purification device 2 or 3 and inputted automatically and continuously in real time):
(3) ΔP' (TMP) (measured by a blood purification device 2 or 3 and inputted automatically and continuously in real time):

And parameter η is included in biological information collected by this system, and is collected as follows.

(1) η (the viscosity of waste liquid is measured at several times per day by a viscometer, and the test result is automatically inputted for example through a test information server device 5).

On the basis of data of these collected parameters which are collected by a biological information and device information management system according to this preferred embodiment and then stored in the patient information server device 10, by using expressions (9) and (10), therefore, the main controller 201 of the client device 20 estimates and calculates the clogging ratio K and its change rate per 1 minute ΔK of a filter of a blood purification device 2 or 3, and monitors them continuously and quickly in real time and thereby estimates what degree the clogging of the filter has been made to. The change in set values of the blood purification device 2 or 3 for preventing the development of clogging of the filter (the increase in dosage of an anticoagulant or reduction in filtration flow rate) is properly performed. That is to say, the main controller 201 of the client device 20 transmits a control signal representing an instruction to increase the dosage of an anticoagulant and/or to reduce the filtration flow rate in the blood purification device 2 or 3 in response to the degree of increase of the clogging ratio K described above to the blood purification device 2 or 3 through a LAN 50, a device link server device 8, the LAN 50 and a device link concentrator device 7. By this, the main controller 201 of the client device 20 estimates and calculates the clogging ratio K and its change rate per 1 minute ΔK of the filter of the blood purification device 2 or 3, and can control the device so as to change the set values of the blood purification device 2 or 3 on the basis of these estimated and calculated values.

Next, a tenth embodiment estimating a substance removing ability in consideration of the clogging ratio of a filter attached to the blood purification device 2 or 3 is described in the following.

As manners in which substances pass through pores of a filter of the blood purification device 2 or 3 there are filtration and diffusion. According to a labyrinth pore theory, a sieve factor SC prescribing filtration and a substance transmitting factor Pm prescribing diffusion are represented by the following expressions.

$$SC = g \cdot S_f \quad (11)$$

$$P_m = D \cdot f \cdot S_d \cdot A_k / \tau / \Delta X \quad (12)$$

$$g = \{1-(2/3)q^2 - 0.20217q^5\}/(1-0.75857q^5) \quad (13)$$

$$f = (1-2.105q + 2.0865q^3 - 1.7068q^5 + 0.72603q^6)/(1-0.75857q^5) \quad (14)$$

$$S_f = 2(1-q)^2 - (1-q)^4 \quad (15)$$

$$S_d = (1-q)^2 \quad (16)$$

$$q = r_s/r_p \quad (17)$$

$$r_s = 0.306 \times MW^{-0.456} \quad (18)$$

$$D = 3.11 \times 10^{-9} \times r_s^{-0.984} \quad (19)$$

Here, the symbols of the respective parameters represent the following.

SC: Sieve factor
$P_m$: Intramembranous substance transmitting factor [m/sec]
D: Diffusion coefficient by thermal motion of substance [m$^2$/sec]
g: Friction coefficient between substance and a pore wall in filtration
f: Friction coefficient between substance and a pore wall
$S_f$: Solid body obstruction factor when substance enters pores in filtration
$S_d$: Solid body obstruction factor when substance enters pores in dialysis
$r_s$: Substance radius [m]
$r_p$: Pore radius of a filter [m]
q: Ratio of substance radius to pore radius
MW: Molecular weight of substance And the clearance of substance in blood (which means the ability of removing substance in blood and is referred to as blood clearance) after passing through the circuit at the time of performing a continuous hemodialysis filtration (CHDF) is represented by the following expressions.

$$CL_b = CL_w + CL_m \quad (20)$$

$$CLw = CL_f + CL_d \quad (21)$$

$$CL_f = (1 - CL_d/Q_p) SC \cdot Q_f \quad (22)$$

$$CL_d = [1-\exp\{P_m \cdot A_m(1-K/100)/6.0 \times 10^{-5} Q_p(1-Q_p/Q_d)\}] \quad Q_p/[Q_p/Q_d - \exp\{P_m \cdot A_m \cdot (1-K/100)/6.0 \times 10^{-5} Q_p(1-Q_p/Q_d)\}] \quad (23)$$

$$Q_p = Q_b(1 - Ht/100) \quad (24)$$

$$CL_m = CL_{m0} \cdot \exp(-a \cdot t) \quad (25)$$

Here, the symbols of these parameters represent the following.

$CL_b$: Clearance of substance in blood (blood clearance) after passing through the circuit [ml/min]
$CL_w$: Clearance into waste liquid [ml/min]
$CL_m$: Clearance by adsorption to a filter [ml/min]
$CL_f$: Filtration clearance [ml/min]
$CL_d$: Diffusion clearance [ml/min]
$A_m$: Area of membrane of a filter [m²]
K: Clogging ratio of a filter [%] (this is represented by expression (9))
$Q_p$: Flow rate of blood plasma [ml/min]
$Q_b$: Flow rate of blood [ml/min]
$Q_d$: Flow rate of dialyzed liquid [ml/min]
$Q_f$: Flow rate of filtration [ml/min]
SC: Sieve factor
$H_t$: Hematocrit value [%]
$CL_{m0}$: Clearance by adsorption to a filter at the beginning [ml/min]
a: Specific constant
t: Elapsed time (min)

Further, the blood clearance $CL_b$ after passing through the circuit at the time of performing a continuous hemodialysis filtration (CHDF) is represented by the following expression.

$$CL_b = CL_f + CL_d + CL_m \qquad (26)$$

In this tenth embodiment, parameters $A_k$, $A_m$, τ, ΔX and $r_p$ are prescribed by the kind of a filter, and parameters $A_k$, $A_m$, τ, ΔX, $Q_f$, $Q_b$, $Q_f$, $Q_d$, Ht and η are included in biological information and device information collected by a biological information and device information management system according to this preferred embodiment, and these parameters are collected as follows.

(1) $A_k$, $A_m$, τ, ΔX and $r_p$ (manually inputted):
(2) $Q_b$, $Q_f$, $Q_d$ and t (measured by a blood purification device 2 or 3 and inputted automatically and continuously in real time):
(3) ΔP' (TMP) (measured by a blood purification device 2 or 3 and inputted automatically and continuously in real time):
(4) $H_t$ (measured by a circulating blood volume measuring device 4 or a pulse oximeter and inputted automatically and continuously in real time):
(5) η (the viscosity of waste liquid is measured at several times per day by a viscometer, and the test result is automatically inputted through a test information server device 5).

Further, parameter MW is the molecular weight of substance to be removed such as a drug and the like and is data which is included in therapeutic information collected by a biological information and device information management system according to this preferred embodiment and is manually inputted.

After the information has been collected as described above, on the basis of data stored in the patient information server device 10, the main controller 201 of the client device 20 can calculate a filtration clearance $CL_f$ and a diffusion clearance $CL_d$ by means of the expressions (21) and (22). And in many examples, by collecting the above-mentioned information and simultaneously measuring the pharmacokinetics of each drug in blood by means of a biological information and device information management system according to this preferred embodiment, it is possible to estimate the amount of substances such as a drug and the like removed by blood purification in a patient receiving a blood purification by identifying parameters $CL_{m0}$ and a at the time of administering the drug to the patient receiving the blood purification under the same condition and calculating parameter $CL_m$ using expression (25).

Next, an eleventh embodiment estimating the pharmacokinetics of a drug in blood of a human body and controlling the dosage of the drug on the basis of the substance removing ability of a filter estimated as described above of the blood purification device 2 or 3 is described.

Since infection is one of important factors to determine the convalescence of a patient with a serious disease, it is important in performing treatment to keep proper the concentration of an antibiotic being a therapeutic drug for it in blood. And since a vasopressor has an intensive physiological activity even when it is small in amount, in case of performing a blood purification on a patient keeping a proper pressure by administering a vasopressor, there is the possibility that the blood pressure is lowered due to removal of the vasopressor by the blood purification. Further, a large amount of anticoagulant is given into the circuit in order to prevent the clogging of a filter attached to the blood purification device 2 or 3, and when the dosage of anticoagulant is a little, a filter is forcibly replaced due to clogging, and this leads to the loss of blood and comes into question from the viewpoint of safety and economy. However, since an anticoagulant has influence on the whole body, an excessive dosage of it may not only cause a serious hemorrhagic complication (cerebral hemorrhage and the like) but also come into question from the viewpoint of economy since the anticoagulant is expensive.

When a drug is administered to a patient receiving a blood purification, the pharmacokinetics of the drug in blood is influenced by the drug discharging ability of the liver and kidney, the state of administering the drug and the drug removing ability by the blood purification. Therefore, from the point of safety and effectiveness in treatment, when administering an important drug (antibiotic, vasopressor, anticoagulant and the like), the dosage of the drug should be determined as measuring the concentration of it in blood, but it is impossible to quickly measure it except some drugs and additionally the measurement of it needs a large cost.

By the way, the concentration of drug in blood is represented by the following expression.

$$C = (D - CL_h - CL_r - CL_p)/V_d \qquad (27)$$

Here, the symbols of the respective parameters represent the following.

C: Concentration of drug in blood
D: Dosage (manual input)
$CL_h$: Clearance by liver
$CL_r$: Clearance by kidney
$CL_p$: Clearance by a blood purification device 2 or 3
$V_d$: Internal distribution volume Here, the internal distribution volume $V_d$ is a known value corresponding to a drug, dosage D is included in therapeutic information collected by a biological information and device information management system according to this preferred embodiment, and clearances $CL_h$ and $CL_r$ can be estimated and calculated from the following biological information collected by a biological information and device information management system according to this preferred embodiment.

(1) Test values by blood test (blood-tested at several times per day and its test result is automatically inputted through a test information server device 5):
(1-1) Test values of liver function: GOT, GPT, LDH, T-Bil, D-Bil, ALP, LAP, γ-GTP and the like:
(1-2) Test values of kidney function: BUN, Cr, β2-MG and the like:

(2) Amount of urine (the amount of urine discharged through a catheter is measured by a urine amount measuring device and is inputted automatically and continuously in real time.)

Further, the clearance $CL_p$ by the blood purification device 2 or 3 can be obtained as a substance removing ability (inputted automatically and continuously in real time) considering the clogging ratio of a filter by a biological information and device information management system according to this preferred embodiment using a method of the ninth or tenth embodiment.

Therefore, by collecting every information of the respective parameters D, $CL_h$, $CL_r$ and $CL_p$ using a biological information and device information management system according to this preferred embodiment, it is possible to keep the concentration of drug in blood proper by, for example, estimating the rise of concentration of drug in blood C caused by drop of clearances $CL_h$ and $CL_r$ in the liver and kidney due to multiple-organ deficiency, for example reducing the dosage of a drug into the whole body or into the blood purification device 2 or 3 by means of a transfusion pump 41 or a syringe pump 42, or increasing the clearance $CL_p$ by blood purification through increasing the filtration rate of the blood purification device 2 or 3. That is to say, the main controller 201 of the client device 20 estimates and calculates the concentration of drug in blood C using the expression (27) and transmits a control signal to control at least one of the dosage of a drug (therapeutic condition), for example, by a transfusion pump 41 or a syringe pump 42 according to the change of the calculated concentration of drug in blood and the set value in the blood purification device 2 or 3 to the transfusion pump 41, the syringe pump 42 or the blood purification device 2 or 3 through the LAN 50, the device link server device 8, the LAN 50 and the device link concentrator 7. By this, the main controller 201 of the client device 20 can estimate and calculate the concentration of drug in blood on the basis of the collected data, and on the basis of this result, can control at least one of the dosage of a drug and the set value of the blood purification device 2 or 3.

Although the eleventh embodiment described above estimates and calculates the concentration of a drug or medicine in blood, the present invention is not limited to this but may estimate and calculate the concentration of substance (including substances administered to a patient and substances not administered from the outside but produced inside the body) other than drugs or medicines, and on the basis of this, may control so that the dosage of the relevant substance to the patient becomes a specified dosage.

Next, a twelfth embodiment estimating the absolute amount of water in a human body and its distribution, and controlling the input/output balance of water is described.

The reduction in circulating blood volume caused by a sudden change in balance of water and electrolyte during performing a blood purification brings the danger of dropping the blood pressure. Particularly, in case of performing a blood purification, replacement of a large amount of blood or a continuous blood purification on a patient being unstable in circulation, it is necessary for performing a blood purification in safety to accurately grasp the water balance in real time and adjust the amount of transfusion or water removal.

The input/output balance of bodily water W is generally calculated by the following expression.

$$W=(A+P+M)-(U+R+S+D) \tag{28}$$

Here, the input/output balance W being a positive value means that the amount of inputted water is larger than the amount of outputted water, and the input/output balance W being a negative value means that the amount of outputted water is larger than the amount of inputted water. The symbols of the respective parameters mean the following.

A: Amount of transfusion
P: Amount of ingested water (through drinking, dining and the like)
M: Amount of water of metabolism
U: Amount of urine
R: Amount of water removed by a blood purification device 2 or 3
S: Water included in feces
D: Amount of transpiration Here, the amount of water of metabolism M is approximated by a known value (400 ml), and the amount of transpiration D is represented by the following expression.

$$D=15BW\times[1+0.15(BT-37.0)] \tag{29}$$

Here, BW is a body weight [kg], BT is a bodily temperature [° C.], and these parameters BW and BT are included in biological information collected by a biological information and device information management system according to this preferred embodiment, and the former body weight BW is a parameter to be manually inputted and the latter bodily temperature. In addition, BT is a parameter which is measured by a bedside monitor device 1, for example, and is inputted automatically and continuously in real time. And both of the amount of transfusion A and the amount of ingested water P (through drinking, dining and the like) are parameters which are included in therapeutic information collected by a biological information and device information management system according to this preferred embodiment, and which are manually inputted. Further, the amount of urine U and the amount of water included in feces S are included in biological information collected by a biological information and device information management system according to this preferred embodiment, and the amount of urine U is measured by measuring the amount of urine from a catheter inserted into the body of a patient by means of a uroflowmeter and is inputted automatically and continuously in real time, and the amount of water included in feces S is manually inputted. And furthermore, the amount R of water removed by a blood purification device 2 or 3 is included in device information collected by a biological information and device information management system according to this preferred embodiment, and is automatically measured by the blood purification device 2 or 3 and is inputted automatically and continuously in real time.

Therefore, by collecting every information of these all parameters A, P, M, U, R, S and D by means of a biological information and device information management system according to this preferred embodiment, it is possible to grasp biological information about the input/output balance of bodily water quickly and accurately in real time. Further, the movement of water in a human body can be grasped by means of (a) the change rate of circulating blood volume (inputted automatically and continuously in real time) and (b) the amount of movement of humor from interstitial tissue into blood vessels (inputted automatically and continuously in real time) which are biological information measured by a circulating blood volume measuring device 4. By adding (a) the absolute amount of water inside cells (inputted automatically and continuously in real time) and (b) the absolute amount of water outside of cells (inputted automatically and continuously in real time) which are biological information measured by a biological impedance measuring device 44 to those information, it is possible to estimate and calculate the absolute amount and distribution of bodily water. Here, the distribution of bodily water refers to the ratio of distribution related to each amount of water regarding:

(1) the amount of water inside cells,
(2) the amount of water outside cells (inside blood vessels), and
(3) the amount of water outside cells (in interstitial tissue).

Therefore, by quickly and accurately grasp water information (absolute mount, distribution and movement) and the input/output balance of water in the body using a biological information and device information management system according to this preferred embodiment, it is possible to prevent the deterioration in organ deficiency (worsening of respiratory insufficiency and the like) caused by a fact that the osmotic pressure is lowered by an excessive increase in transfusion or an excessive reduction in amount of water removal of a blood purification device in case that the amount of circulating blood is reduced and the blood pressure is lowered due to a sudden dehydration by a blood purification, properly increase the amount of transfusion by a transfusion pump 41, reduce the dehydration of a blood purification device 2 or 3, reduce the dosage of a diuretic (leading to reduction in urine flow rate per unit time) by a syringe pump 42, and thereby increase the amount of circulating blood and raise the blood pressure and keep it stable thereafter. That is to say, the main controller 201 of the client device 20 estimates and calculates the absolute amount of bodily water and its distribution by means of the above expressions (28) and (29) on the basis of the data collected as described above, and on the basis of this, transmits a control signal for instructing the control of the set values of the transfusion pump 41, the syringe pump 42, and the blood purification device 2 or 3 so as to prevent the organ insufficiency in a human body to the transfusion pump 41, the syringe pump 42, and the blood purification device 2 or 3 through the LAN 50, the device link server device 8, the LAN 50 and the device link concentrator 7. By this, the main controller 201 of the client device 20 can estimate and calculate the absolute amount of bodily water and its distribution, and can properly control the input/output balance of bodily water.

Next, a thirteenth embodiment estimating biological information about oxygen and controlling the set values of a respirator 43 and the set values of a blood purification device 2 or 3 is described.

Performing a blood purification (continuous hemofiltration, continuous hemodialysis filtration and the like) on a patient in respiratory insufficiency resorting to artificial respiration using a respirator 43 improves the respiratory function and the oxygen consumption of tissue by removing water of the lungs or removing harmful substances in blood causing organic deficiency. And blood purification is sometimes performed for the purpose of correcting an acid-base balance, but since the acid-base balance is influenced by the state of respiration, the setting of artificial respiration may be adjusted for the purpose of correcting the acid-base balance. In such a way, respiration control and blood purification are medical treatments related closely to each other. When performing artificial respiration on a patient in respiratory insufficiency, in order to grasp the condition of a disease and perform a proper artificial respiration control, the oxygen conveyance per minute $DO_2$ (which is originally represented as D having a dot "•" on its top but the dot is omitted for simplification), the oxygen consumption $VO_2$ (which is originally represented as V having a dot "•" on its top but the dot is omitted for simplification) and the oxygen uptake rate are calculated by means of the following expressions.

$$DO_2 = CaO_2 \times CO \times 10 \quad (30)$$

$$VO_2 = (CaO_2 - CvO_2) \times CO \times 10 \quad (31)$$

$$ER = VO_2/DO_2 = 1 - CvO_2/CaO_2 \quad (32)$$

$$CaO_2 = 1.39 \times Hb \times aSpO_2/100 \quad (33)$$

$$CvO_2 = 1.39 \times Hb \times vSpO_2/100 \quad (34)$$

$$Hb = (Ht - 0.83)/3.009813 \quad (35)$$

Here, the respective parameters mean the following.
$DO_2$: Oxygen conveyance [ml/min]
$VO_2$: Oxygen consumption [ml/min]
ER: Oxygen uptake rate
$CaO_2$: Oxygen concentration in arterial blood [ml/dl]
$CvO_2$: Oxygen concentration in venous blood [ml/dl]
CO: Cardiac output [l/min]
$aSpO_2$: Degree of oxygen saturation of arterial blood [%]
$vSpO_2$: Degree of oxygen saturation of venous blood [%]
Hb: Hemoglobin concentration [g/dl]
Ht: Hematocrit value [%]

Hereupon, the parameters $aSpO_2$, Ht and CO are included in biological information collected by a biological information and device information management system according to this preferred embodiment, and for example they are measured by inserting a Swan-Ganz catheter into a patient and using a cardiac output meter, or they are collected and measured as follows.

(1) $aSpO_2$ (is measured by a pulse oximeter and inputted automatically and continuously in real time):
(2) Ht (is measured by a pulse oximeter and inputted automatically and continuously in real time):
(3) CO (is measured by an ultrasonic cardiograph and inputted automatically and continuously in real time)

And the parameters Ht and $vSpO_2$ are included in biological information collected by a biological information and device information management system according to this preferred embodiment, and both of them are measured by a circulating blood volume measuring device 4 and are inputted automatically and continuously in real time.

Hitherto, measurement of the parameters $aSpO_2$, $vSpO_2$, Ht and CO has needed to insert a Swan-Ganz catheter and perform a blood test, but as described above, those parameters can be bloodlessly inputted automatically and continuously in real time by using a pulse oximeter, an ultrasonic cardiograph and a circulating blood volume measuring device 4.

By using a biological information and device information management system according to this preferred embodiment, therefore, it is possible to noninvasively input the parameters $aSpO_2$, $vSpO_2$, Ht and CO automatically and continuously in real time and on the basis of this, calculate non-invasively in real time and monitor continuously the parameters $DO_2$, $VO_2$ and ER by means of expression (30) to (35). That is to say, by monitoring the parameters $DO_2$, $VO_2$ and ER being biological information about oxygen continuously in real time by means of a biological information and device information management system according to this preferred embodiment, it is possible to properly perform a blood transfusion, increase a drug for increasing an cardiac output, start an artificial respiration and change set values during performance (increase the concentration of oxygen to be administered or increase breath per minute) in case that peripheral tissue falls into insufficiency of oxygen due to insufficiency of oxygen conveyance ($DO_2$). Further, it has been reported that blood purification has a function of improving a tissular oxygen metabolic imbalance by removing a mediator in blood, and in case that the parameters $VO_2$ and ER are low due to a tissular oxygen metabolic imbalance, it is possible to improve (increase) the parameters $VO_2$ and ER by properly improving the substance removing efficiency through increasing the filtration rate of blood purification or by properly lengthening the period of time of performing blood purification as taking the parameters $VO_2$ and ER as indexes.

On the basis of the data collected as described above, therefore, the client device 20 calculates the parameters $DO_2$, $VO_2$ and ER being biological information about oxygen and on the basis of this, transmits a control signal to instruct controlling the set values of a respirator 43 and a blood purification device 2 or 3 so as to increase and improve the parameters $DO_2$, $VO_2$ and ER to the respirator 43 and the blood purification device 2 or 3 through the LAN 50, the device link server device 8, the LAN 50 and the device link concentrator 7. Due to this, the main controller 201 of the client device 20 can calculate the parameters $DO_2$, $VO_2$ and ER being biological information about oxygen, properly control the respirator 43 and the blood purification device 2 or 3, and improve the respiratory function of a patient of respiratory insufficiency.

In the above embodiment, the main controller 201 of the client device 20 calculates various data but may display these calculated data on a display part 204, record and store them in a patient information file 206a in a hard disk storage 206, record them on a plain paper or a thermal paper by means of a printer (not illustrated), or transfer them to another device.

As described above, according to this preferred embodiment, the patient information server device 10 takes in automatically and periodically information outputted from devices 1 to 5 and 41 to 48 at specific intervals and store the information together with time information, and the client device 20 accesses the patient information server device 10 and downloads the above stored information or accesses the patient information server device 10 periodically at other time intervals, downloads the above stored information together with time information, and simultaneously and chronologically displays or records biological information and device information including the downloaded blood amount information and the like. Accordingly, this preferred embodiment has the following particular effects.

(1) This embodiment can grasp in real time biological information about the human body of a patient or the like and device information of a blood-treating device and the like at the time of performing a blood treatment.

(2) Since it makes it possible to display simultaneously and chronologically device information corresponding to the condition of a patient and biological information including blood amount information and not only display one piece of information but also confirm the correlation between the respective pieces of information, it makes it possible to find an abnormal condition in its early stages. And it enables to prevent a medical accident and is very effective to safety management.

(3) By storing data in the patient information server device 10 and displaying them on the client device 20, it is possible to determine proper settings regarding a blood treatment method such as a blood purification method and the like for each case, and it is possible to reduce the danger of medical treatment, shorten the period of treatment and, in its turn, reduce the cost of treatment. And by performing a medical treatment based on the optimum values, it is possible to expect an early improvement of a patient's convalescence.

(4) By storing data in the patient information server device 10 and displaying them on the client device 20, it is possible to confirm the life of a filter of the blood purification device 2 or 3 and the aptitude and the like of the filter under various environments and this becomes effective for developing a filter in the future. Particularly, it is possible to estimate the clogging ratio of a filter of the blood purification device 2 or 3 and properly control the set value of flow rate of the blood purification device 2 or 3 and the dosage of an anticoagulant.

(5) By storing data in the patient information server device 10 and displaying them on the client device 20 this embodiment becomes effective for the evaluation of pharmacokinetics and for the administration of drugs during performance of a blood treatment. Particularly, this enables to estimate a substance removing ability in consideration of the clogging ratio of a filter of the blood purification device 2 or 3 and to estimate pharmacokinetics in a human body. Due to this, it is possible to properly control the dose of a drug.

(6) This embodiment makes it possible to estimate the absolute amount of water in a human body and its distribution during performance of a blood purification by the blood purification device 2 or 3 and properly control the amount of inputted water and the amount of outputted water.

(7) This embodiment makes it possible to estimate biological information about oxygen in a human body during performance of a blood purification by the blood purification device 2 or 3 and properly control the respirator and the blood purification device 2 or 3.

VARIATION EXAMPLE

Although the above-mentioned embodiments use a blood purification device 2 or 3, the present invention is not limited to this but may use a blood-treating device for performing a specific blood treatment. Blood purification (BP) is a general term for therapeutics for correcting an abnormal condition of blood in volume and quality by means of physical principles such as diffusion, osmosis, filtration, exchange, adsorption and the like, and thereby attempting to obtain a therapeutic effect. In spite of means for correcting abnormal conditions of blood in volume and quality, many blood purification methods are therapeutic means attempting to obtain a therapeutic effect by correcting an abnormal condition of blood plasma in volume and quality except a therapeutic means of removing the leukocyte causing a disease in a leukocyte removing treatment. As blood treatments other than blood purification, there are the following treatments.

(1) Separate collection of blood components by centrifugation: This includes separate collection of red blood cells and separate collection of blood platelets, for example.

(2) Method using an automatic blood collecting device instead of a centrifugal separator: This includes, for example, the blood collection by an automatic blood collector (blood collection for blood donation or self-transfusion of blood. This often collects blood naturally into a bag utilizing blood pressure without using a device, but there is also an automatic blood collector for exclusive use.) and the phlebotomy by an automatic blood collector (which discards the collected blood for the purpose of reducing blood against chronic hepatitis C, hemosiderosis or the like. This often discards naturally blood utilizing blood pressure without using a device.).

(3) Cardiopulmonary assist using extracorporeal circulation (3-1) Extracorporeal lung assist (ECLA)

(3-2) Extracorporeal membrane oxygenation (ECMO)

(3-3) Extracorporeal carbon dioxide removal ($ECCO_2R$)

(3-4) Extracorporeal lung and heart assist (ECLHA)

(3-5) Extracorporeal life support (ECLS)

(3-6) Percutaneous cardiopulmonary support system (PCPS)

(3-7) Intravascular blood gas exchanger (IVBGE)

(3-8) Intravenous oxygenator (IVOX) and the like (4) Cardiopulmonary assist using no extracorporeal circulation
(4-1) Respirator
(4-2) Intra-aortic balloon pumping (IABP)
(5) Artificial organ (which is made by cultivated cells, cloning technologies and the like and provided in a patient): This includes, for example, an artificial liver, artificial kidney, artificial cor, artificial lung and the like.

A management system according to this preferred embodiment can be used in performing various blood treatments (blood purification (chronic dialysis and acute blood purification) and others) on various patients for various purposes (auxiliary artificial kidney, auxiliary artificial liver, auxiliary artificial lung, auxiliary artificial cor, and removal of mediator).

Although the above-mentioned embodiments store and display or record data of patient information, the present invention is not limited to this but may store and display or record data about a human body being not a patient or a human body equipped with an artificial organ. And it may record or store data of a flow sheet in a specific storage device.

Although the above-mentioned embodiments calculate and display or record specific indexes or scores on the basis of data of patient information, the present invention is not limited to this but may simultaneously and chronologically display or record, together with the above information to be displayed or recorded, index values calculated by means of specific arithmetic expressions on the basis of at least one of biological information measured about a human body by a biological measuring device, information about at least one of biological information and device information measured by a blood-treating device for treating blood taken from the human body, and blood information measured by a circulating blood volume measuring device for measuring blood information of circulating blood taken from the human body. And the present invention may simultaneously and chronologically display or record, together with the above information to be displayed or recorded, index values calculated by means of specific arithmetic expressions on the basis of at least one of biological information measured about a human body by a biological measuring device, information about at least one of biological information and device information measured by a blood treatment device for treating blood taken from the human body, blood information measured by a circulating blood volume measuring device for measuring blood information of circulating blood taken from the human body, and other biological information manually inputted.

A management system for biological information and information about a blood-treating device of an embodiment according to the present invention is a system which grasps transversely three of cellular medical care, blood and vessel function medical care and neurological medical care, utilizes comprehensively medical information in all cases of therapeutic treatment and improves the quality and safety of medical care, and can be said to be a safety medical care supporting system. That is to say, this system is a system contributing to the enhancement in quality of medical care and the improvement in safety of medical care from the viewpoint of how early a disease is diagnosed and how painlessly and how early a medical treatment is performed, by using a medical treatment supporting technology using advanced information processing technologies, more concretely, by using technologies of providing an operative feeling of no physical disorder and a fail-safe working environment in low-invasive techniques or techniques which lighten physical and mental burdens of a patient and simplify and reduce in labor therapeutic actions demanded from medical people by making plural medical appliances systematized and multi-functional. For example, it provides a therapeutic navigation by presenting information to medical people as following transformation of an organ.

INDUSTRIAL APPLICABILITY

As described above in detail, the present invention automatically accumulates and stores biological information measured about a human body by a biological measuring device, information about at least one of biological information and device information measured by a blood-treating device for treating blood taken from the human body, and blood information measured by a circulating blood volume measuring device for measuring blood information of circulating blood taken from the human body in a server device together with time information, and simultaneously and chronologically displays or records the information stored in the server device.

Accordingly, the present invention has the following particular effects.
(1) The invention can grasp biological information about the human body of a patient or the like and device information of a blood-treating device and the like in real time at the time of performing a blood treatment.
(2) Since it makes it possible to display simultaneously and chronologically device information corresponding to the condition of a patient and biological information including blood amount information and not only display one piece of information but also confirm the correlation between the respective pieces of information, it makes it possible to find an abnormal condition in its early stages. And it enables to prevent a medical accident and is very effective for safety management.
(3) By storing and displaying or recording biological information and device information about a blood-treating device and the like in a server device, it is possible to determine proper settings regarding a blood treatment method for each patient, and it is possible to reduce the danger of medical treatment, shorten the period of treatment and, in its turn, reduce the cost of treatment. And by performing a medical treatment on the basis of the optimum values, it is possible to expect an early improvement of a patient's convalescence.
(4) By storing and displaying or recording biological information and device information about a blood-treating device and the like in a server device, it is possible to confirm the life of a filter of a blood-treating device and the aptitude and the like of the filter under various environments, and this becomes effective for developing a filter in the future. Particularly, it is possible to estimate the clogging ratio of a filter of a blood-treating device and properly control the set value of flow rate of the blood purification device and the dose of an anticoagulant.
(5) By storing and displaying or recording biological information and device information about a blood-treating device and the like in a server device, the present invention is effective for evaluation of pharmacokinetics and proper administration of drugs during performance of a blood treatment. Particularly, this enables to estimate a substance removing ability in consideration of the clogging ratio of a filter of a blood-treating device and estimate the pharmacokinetics of a drug in a human body. Due to this, it is possible to properly control the dose of the drug.
(6) The invention makes it possible to estimate the absolute amount of water in a human body and its distribution during performance of a blood purification by a blood-treating device such as a blood purification device and the like and properly control the amount of inputted water and the amount of outputted water.

(7) The invention makes it possible to estimate biological information about oxygen in a human body during performance of a blood purification by a blood-treating device such as a blood purification device and the like and properly control the respirator and the blood-treating device.

The invention claimed is:

1. The management system for biological information and information about a blood-treating device comprising:
    a blood purifying device which takes blood from a human body, purifies the blood, and returns the purified blood to the human body;
    a server device which automatically accumulates and stores time information and
        (a) biological information about a human body measured by a biological-measuring device,
        (b) information about at least one of device information and biological information measured by the blood purification device, and
        (c) blood information measured by a circulating blood volume measuring device that measures blood information about the blood taken from the human body; and
    a control device which calculates an index value using a predetermined arithmetic expression based on at least one of the stored information or downloaded information, controls the blood purifying device in accordance with the calculated index value, and simultaneously and chronologically displays or records the calculated index value together with the information to be displayed or recorded,
    wherein the index value is indicative of effects of the blood purification on the human body,
    a client device which controls the control device to simultaneously and chronologically display or record the information stored in the server device and the calculated index value; and
    an input means for entering additional biological information which is different from initial biological information, wherein
    the control device simultaneously and chronologically displays or records the downloaded information and the additional biological information, wherein
    the control device changes at least one additional time interval and a display scale in response to a predetermined variation in at least one of the downloaded information, the calculated index value, and the additional biological information.

2. A management system for biological information and information about a circulating blood purifying device that purifies blood from a human body comprising:
    a server device which automatically accumulates and stores time information together with:
        (a) biological information about the human body measured by a biological-measuring device,
        (b) device information measured by the blood purifying device, and
        (c) blood information measured by a circulating blood volume measuring device that measures blood information about the blood taken from the human body for purification;
    the blood purification device taking blood from the human body, submitting the blood to filtration, dialysis or adsorption by the use of a filter, and returning the blood to the human body;
    a control processor which simultaneously and chronologically displays or records the information stored in the server device, the control processor being programmed to:
        calculate an estimate of a percent clogging of the filter attached to the blood purification device, based on the information stored in the server device,
        control a predetermined value of the blood purification device based on the calculated percent clogging of the filter,
        calculate an estimate of the amount of substances in blood removed by the blood purification device based on the information stored in the sever device and the calculated percent clogging of the filter,
        calculate an estimate of the concentration of a specific substance in blood based on the information stored in the server device, the calculated percent clogging of the filter and the calculated amount of substances in blood removed by the blood purification device,
        control, based on the calculated concentration of the specific substance, a dose of an administered substance administered to the human body; and
    a client device for supplying the control processor with the information stored in the server device; and
    wherein the device information includes at least one selected from the group consisting of: items of a ledger, set values, pressure information, flow rate information, temperature information, anticoagulant dosage information (concentration, dosing rate), the amount of anticoagulant used, type, dosing rate, amount used and time of replacement of substituted liquid and dialyzed liquid, alarm information, trouble managing records, event information and safety check items; and
    wherein the time information includes at least one selected from the group consisting of: test time, current date and hour, registration time, current time, start time, end time, time of a condition, time of taking a specimen, time of a dosing, elapsed time, time of replacement of anticoagulant, time of replacement of substituted liquid and dialyzed liquid, time of replacement of a waste liquid tank, specified times, time zone, time of recording a report, time of displaying, time of inputting a vital sign, time of inputting information about a blood treatment, and time of end of a filter.

3. The management system for biological information and information about the blood purifying device as claimed in claim 2, wherein
    the control processor further calculates an estimate of biological information regarding a balance between intra- and extra-cellular contents of bodily water in the human body based on the information stored in the server device.

4. The management system for biological information and information about the blood purification device as claimed in claim 3, wherein
    the control processor further controls a predetermined value of the blood-purification device based on the calculated biological information estimate regarding the balance between the intra- and extra-cellular contents of bodily water in the human body.

5. The management system for biological information and information about the blood purification device as claimed in claim 2, wherein
    the control processor further calculates an estimate of biological information regarding oxygen in the human body based on the information stored in the server device.

6. The management system for biological information and information about the blood purifying device as claimed in claim 5, wherein
the control processor further controls the blood-purification device and an artificial respirator attached to the human body, based on the calculated biological information regarding oxygen in the human body.

7. A management apparatus for biological information and information about a blood-treating device comprising:
a server device for automatically accumulating and storing time information together with:
(a) biological information measured by a biological-measuring device about a patient whose blood is to be treated,
(b) device information measured by a blood-treating device that treats the blood from the patient and returns the treated blood to the patient, and
(c) blood information measured by a circulating blood volume measuring device that measures blood information about the blood in the blood treating device;
a client device for simultaneously and chronologically displaying or recording the information stored in the server device,
a local area network, the server device and the client device communicating using the local area network; and
a control device which calculates an index value using a predetermined arithmetic expression based on at least the stored information and controls the client device to simultaneously and chronologically display or record the calculated index value together with the information stored in the server device,
wherein the index value is indicative of a current medical state of the patient,
wherein the control device calculates an estimate of a balance between intra- and extra-cellular contents of bodily water in the patient based on the information stored in the server device.

8. The management apparatus for biological information and information about a blood-treating device as claimed in claim 7, wherein
the control device controls a predetermined value of the blood purification device based on the calculated estimate of the balance between the intra- and extra-cellular contents of bodily water in the patient.

9. A management method for biological information and information about a blood-treating device, comprising:
automatically accumulating
(a) biological information about a human body when blood from the human body is being treated, the biological information being measured by a biological-measuring device and/or a blood-treating device,
(b) device information about the blood-treating device that treats blood taken from the human body, and
(c) blood information measured by a circulating blood volume measuring device in the blood taken from the human body, and
storing the information, the device information, the blood information, and time information;
calculating an index value using a predetermined arithmetic expression based on at least the biological information, the device information, the blood information, and the time information;
wherein the index value is indicative of a condition of the human body whose blood is being treated;
simultaneously and chronologically displaying or recording the biological information, the device information, the blood information, and the calculated index,
the device information including at least: a blood pressure, a blood pressure in the device, a blood flow rate in the device, a blood temperature in the device, an amount of anticoagulant used, a type of anticoagulant used, and an anticoagulant dosing rate; and
a local area network over which local area network the server device and the client device communicate.

10. The management method for biological information and information about a blood-treating device as claimed in claim 9 further comprising:
measuring the biological information about the human body and outputting the measured biological information;
treating the blood sample taken from the human body and measuring at least one of the biological information and the blood information, followed by outputting the measured biological information;
measuring and outputting the blood information using a circulating blood volume measuring device;
automatically and periodically incorporating the output information at predetermined intervals and storing the output information together with the time information into a server device; and
downloading the stored information together with the stored time information by periodically accessing the server device at predetermined time intervals, and simultaneously and chronologically displaying or recording the downloaded information.

11. The management method for biological information and information about a blood-treating device as claimed in claim 9, further comprising the steps of:
storing diagnostic information, therapeutic information and test information into the server device; and
simultaneously and chronologically displaying or recording at least one of the diagnostic information, the therapeutic information and the test information.

12. The management method for biological information and information about a blood-treating device as claimed in claim 9 further including:
from the index, calculating one or more scores for comprehensively judging the condition of the human body; and
at least one of displaying and recording the scores.

13. A management system for biological information and information about a blood-treating device including:
a server device which automatically accumulates and stores time information and:
(a) biological information about a human body measured by a biological-measuring device,
(b) device information about a blood-treating device that treats a blood from the human body, and
(c) blood information measured by a circulating blood volume measuring device that measures blood information about a circulating blood sample taken from the human body; and
a control device which calculates an index value and a rate of change of the index;
using a predetermined arithmetic expression based on at least one of the stored information or downloaded information and then simultaneously and chronologically displays or records the calculated index value together with the information to be displayed or recorded, wherein the index value is indicative of hypovolemia;
a client device which controls the control device to simultaneously and chronologically display or record the information stored in the server device and the calculated index rate of change; and wherein the server device and the client device communicate using a local area network.

14. A management system for biological information and information about a blood-treating device as claimed in claim 13,
wherein the device information includes: blood pressure information, blood flow rate information, blood temperature information, an amount of anticoagulant used, a type of anticoagulant used, an anticoagulant dosing rate, amount of substituted liquid used, an amount of used dialyzed liquid, alarm information, event information and safety check items; and
wherein the time information includes: test time, current date and hour, registration time, current time, start time, end time, time of a condition, time of taking a specimen, time of a dosing, elapsed time, time of replacement of anticoagulant, time of replacement of substituted liquid and dialyzed liquid, time of replacement of a waste liquid tank, time of recording a report, time of inputting a vital sign, and time of end of a filter.

15. The management system for biological information and information about a blood-treating device, as claimed in claim 13 further comprising:
a biological-measuring device for measuring the biological information about the human body and outputting the measured biological information;
a blood purification device for purifying the blood sample taken from the human body and for measuring and outputting at least the device information;
a circulating blood volume measuring device for measuring the blood information about the circulating blood sample taken from the human body and outputting the measured blood information.

16. A management apparatus for biological information and information about a blood-treating device, comprising:
a server device for automatically accumulating and storing time information together with:
 (a) biological information measured by a biological-measuring device about a patient whose blood is to be treated,
 (b) device information measured by a blood-treating device that treats the blood from the patient and returns the treated blood to the patient, and
 (c) blood information measured by a circulating blood volume measuring device that measures blood information about the blood in the blood treating device;
a client device for simultaneously and chronologically displaying or recording the information stored in the server device;
a local area network, the server device and the client device communicating using the local area network; and
a control device which calculates an index value using a predetermined arithmetic expression based on at least the stored information and controls the client device to simultaneously and chronologically display or record the calculated index value together with the information stored in the server device,
wherein the index value is indicative of a current medical state of the patient,
wherein the control device further calculates and at least one of displays or records a correlation coefficient between at least one of a pair of the index values or a rate of change of the index values.

* * * * *